(12) United States Patent
Bank

(10) Patent No.: US 11,511,120 B2
(45) Date of Patent: Nov. 29, 2022

(54) SYSTEMS AND METHODS FOR OPTIMIZING IMPLANTABLE MEDICAL DEVICE CHARACTERISTICS USING DATA STRUCTURES AND GRAPHICAL REPRESENTATIONS

(71) Applicant: Allina Health System, Minneapolis, MN (US)

(72) Inventor: Alan J. Bank, St. Paul, MN (US)

(73) Assignee: ALUNA HEALTH SYSTEM, Minneapolis, MN (US)

( * ) Notice: Subject to any disclaimer, the term of this patent is extended or adjusted under 35 U.S.C. 154(b) by 0 days.

(21) Appl. No.: 17/596,563

(22) PCT Filed: Jun. 18, 2020

(86) PCT No.: PCT/US2020/038333
§ 371 (c)(1),
(2) Date: Dec. 13, 2021

(87) PCT Pub. No.: WO2020/257388
PCT Pub. Date: Dec. 24, 2020

(65) Prior Publication Data
US 2022/0176125 A1 Jun. 9, 2022

Related U.S. Application Data

(60) Provisional application No. 62/863,453, filed on Jun. 19, 2019, provisional application No. 62/863,452, filed on Jun. 19, 2019.

(51) Int. Cl.
*A61N 1/368* (2006.01)
*A61N 1/05* (2006.01)
*A61N 1/372* (2006.01)

(52) U.S. Cl.
CPC .......... *A61N 1/3682* (2013.01); *A61N 1/056* (2013.01); *A61N 1/36843* (2017.08); *A61N 1/37247* (2013.01)

(58) Field of Classification Search
CPC ..... A61B 5/6869; A61B 5/6867; A61B 5/743; A61B 5/7435; A61B 5/742
See application file for complete search history.

(56) References Cited

U.S. PATENT DOCUMENTS

| 4,428,378 A | 1/1984 | Anderson et al. |
| 5,052,388 A | 10/1991 | Sivula et al. |

(Continued)

FOREIGN PATENT DOCUMENTS

WO WO-2020257388 A1 * 12/2020 ............. A61B 5/282

OTHER PUBLICATIONS

International Search Report and Written Opinion of International Application No. PCT /US2020/038333, dated Oct. 30, 2020, 11 pp.

(Continued)

*Primary Examiner* — Jon Eric C Morales
(74) *Attorney, Agent, or Firm* — Shumaker & Sieffert, P.A.

(57) ABSTRACT

In some examples, a computing apparatus may determine information corresponding to a data structure and indicating delays associated with an atrium lead, a left ventricle (LV) lead, and a right ventricle (RV) lead based on one or more input variables. The computing apparatus may determine a plurality of individualized characteristics based on the information corresponding to the data structure. The computing apparatus may receive, from the plurality of measurement electrodes, a plurality of second sets of electrical measurements indicating second electrical signals applied to the patient's heart based on the plurality of individualized characteristics. The computing apparatus may determine (Continued)

cardiac resynchronization index (CRI) values using a first set of electrical measurements (e.g., native measurements) and the plurality of second sets of electrical measurements. The computing apparatus may generate a graphical representation based on a populated data structure and cause display of the graphical representation.

22 Claims, 51 Drawing Sheets

(56) References Cited

U.S. PATENT DOCUMENTS

| | | | |
|---|---|---|---|
| 7,684,863 B2 | 3/2010 | Parikh et al. |
| 8,972,228 B2 | 3/2015 | Ghosh et al. |
| 9,510,763 B2 | 12/2016 | Ghosh et al. |
| 9,962,097 B2 | 5/2018 | Ghosh et al. |
| 9,974,457 B2 | 5/2018 | Ghosh et al. |
| 10,492,705 B2 | 12/2019 | Bank et al. |
| 11,027,135 B2 | 6/2021 | Ghosh et al. |
| 2009/0306732 A1 | 12/2009 | Rosenberg et al. |
| 2011/0092809 A1 | 4/2011 | Nguyen et al. |
| 2011/0257547 A1 | 10/2011 | Zhang et al. |
| 2011/0264159 A1 | 10/2011 | Spotnitz et al. |
| 2014/0222099 A1 | 8/2014 | Sweeney et al. |
| 2016/0166834 A1 | 6/2016 | Ghosh et al. |
| 2019/0192034 A1 | 6/2019 | Ghosh et al. |
| 2021/0290960 A1 | 9/2021 | Ghosh et al. |

OTHER PUBLICATIONS

Willemen et al. "The Left and Right Ventricles Respond Differently to Variation of Pacing Delays in Cardiac Resynchronization Therapy: A Combined Experimental—Computational Approach," Frontiers in Physiology, vol. 10, No. 17, Feb. 1, 2019, 13 pp.

\* cited by examiner

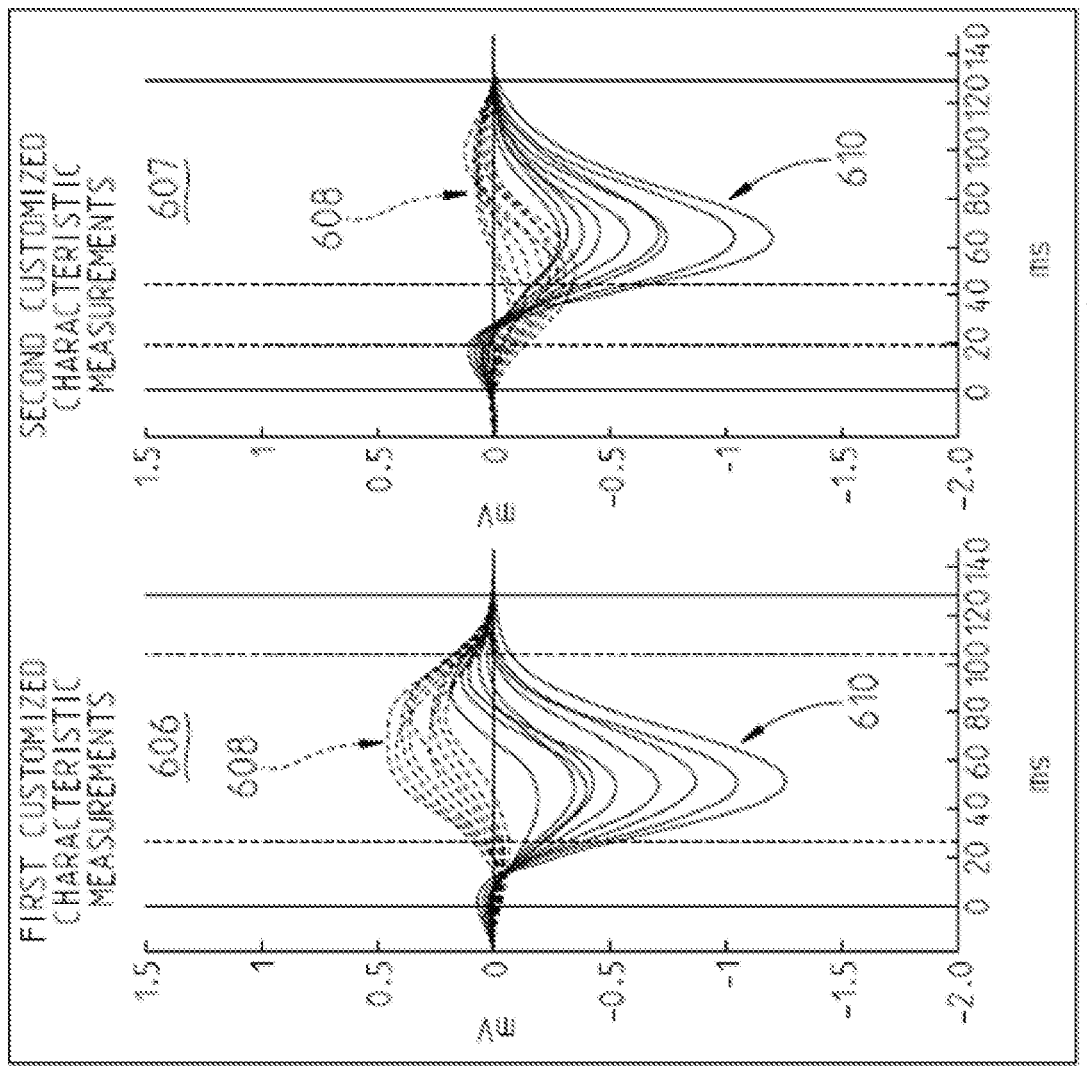
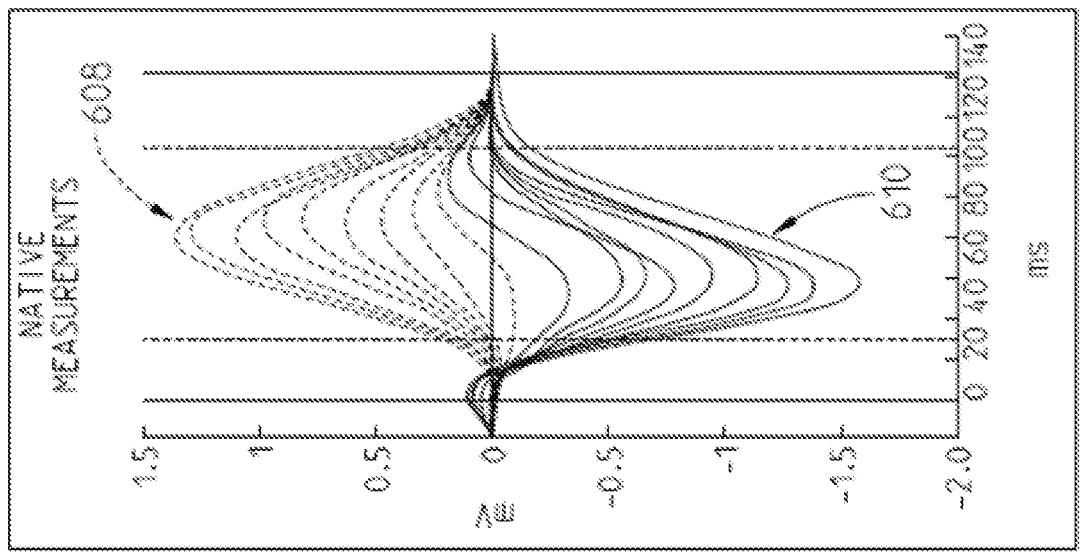
FIG. 12

V-V DELAY METHODS: FIRST DEVICE VS SECOND DEVICE
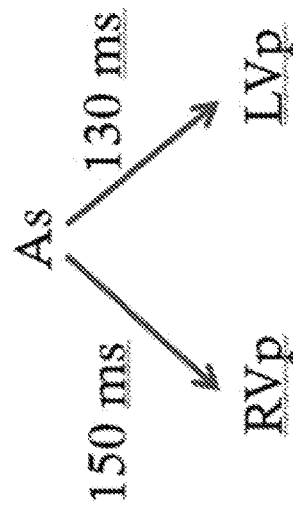
Second Device
830
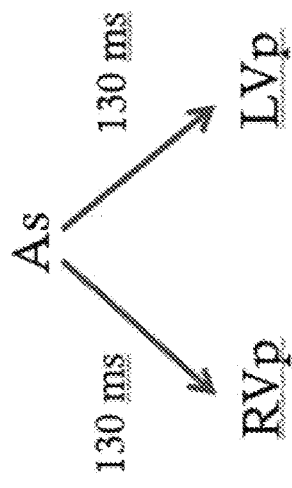
810
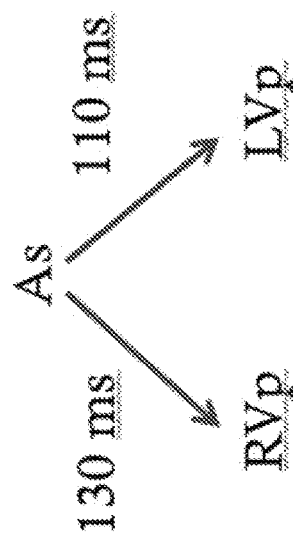
First Device
820
FIG. 21

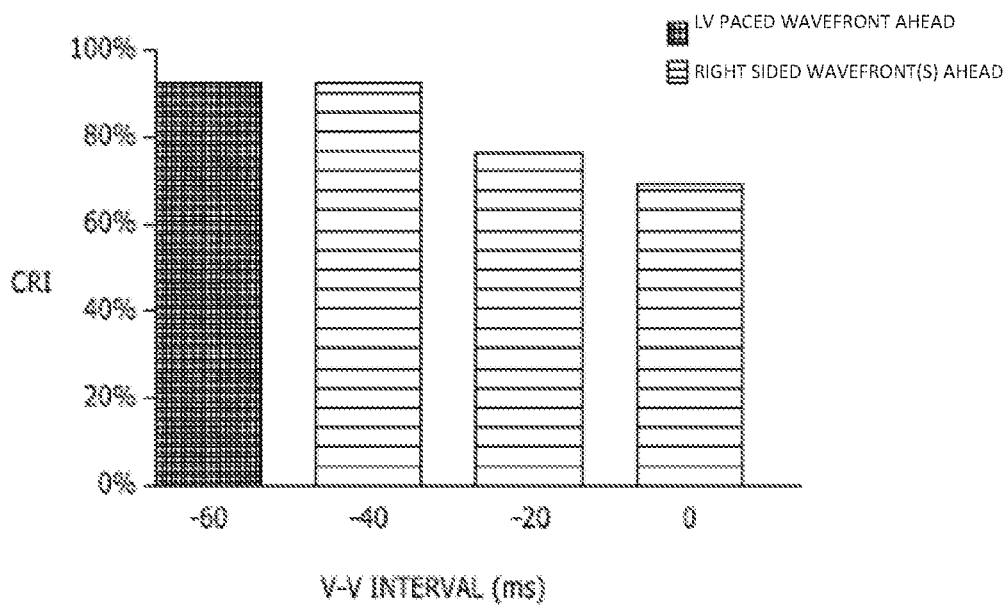
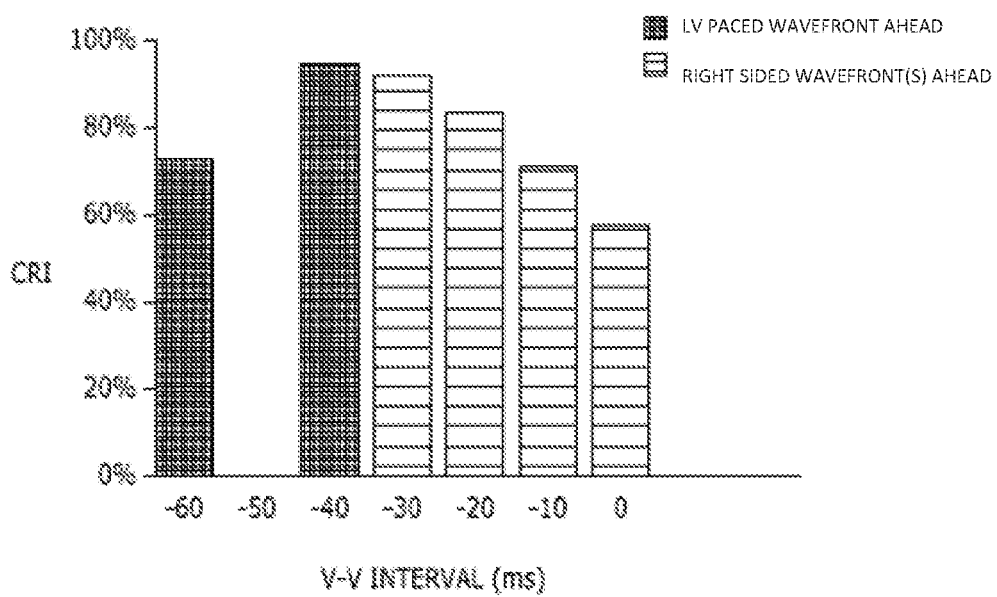
FIG. 23D

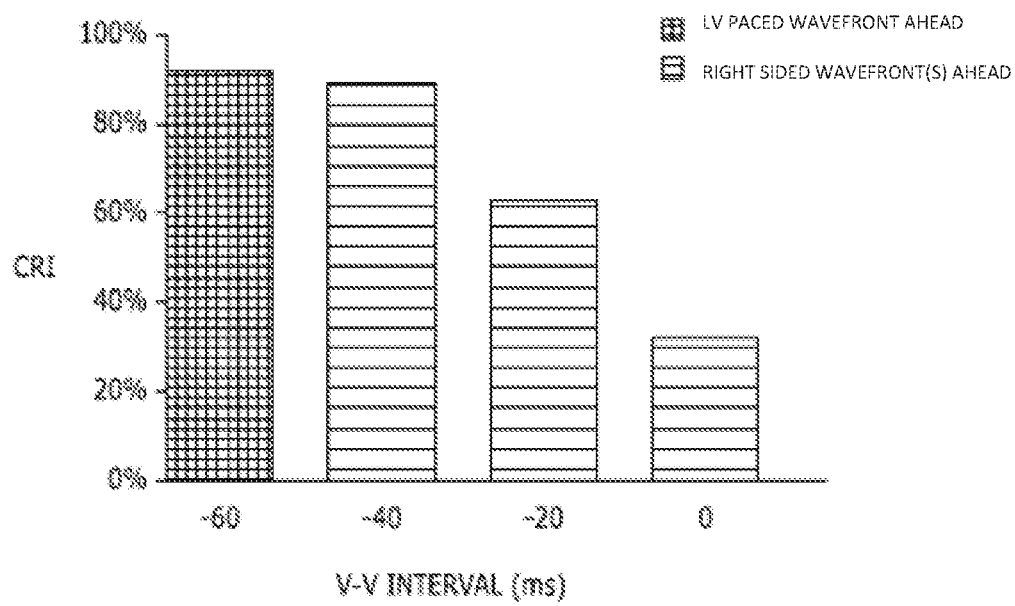
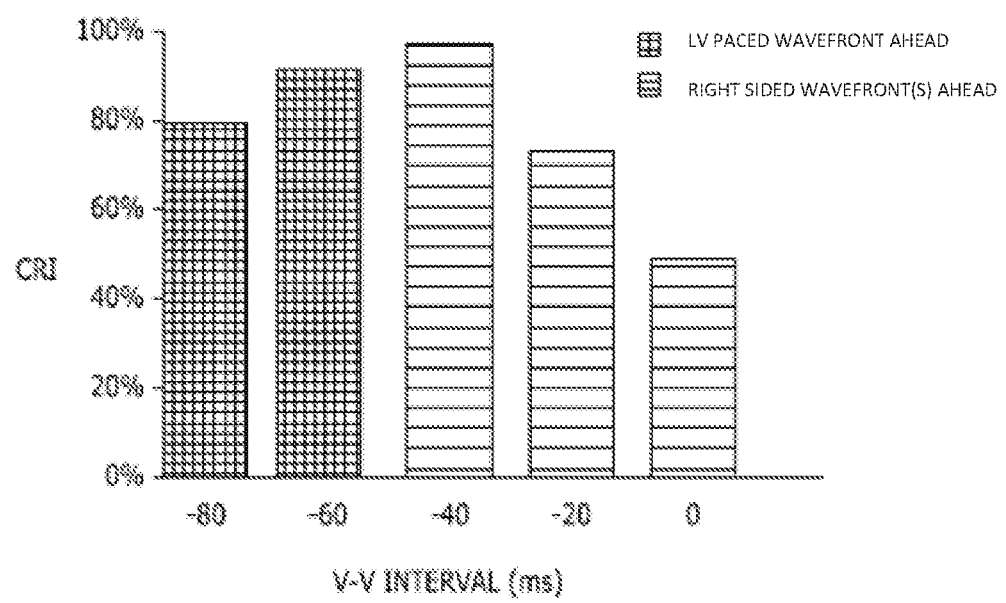
FIG. 23E

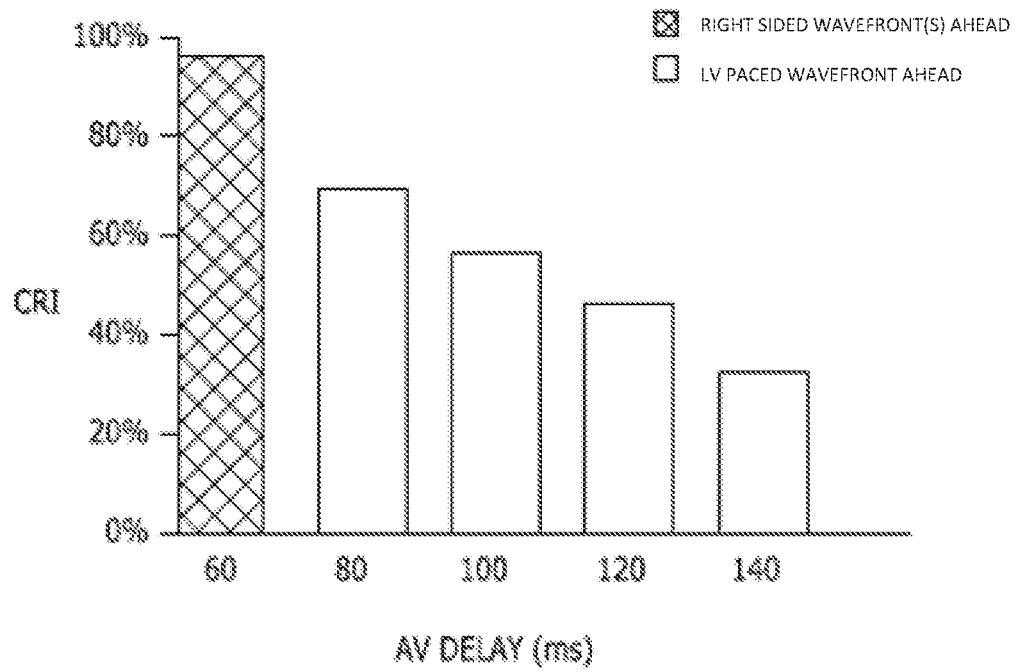
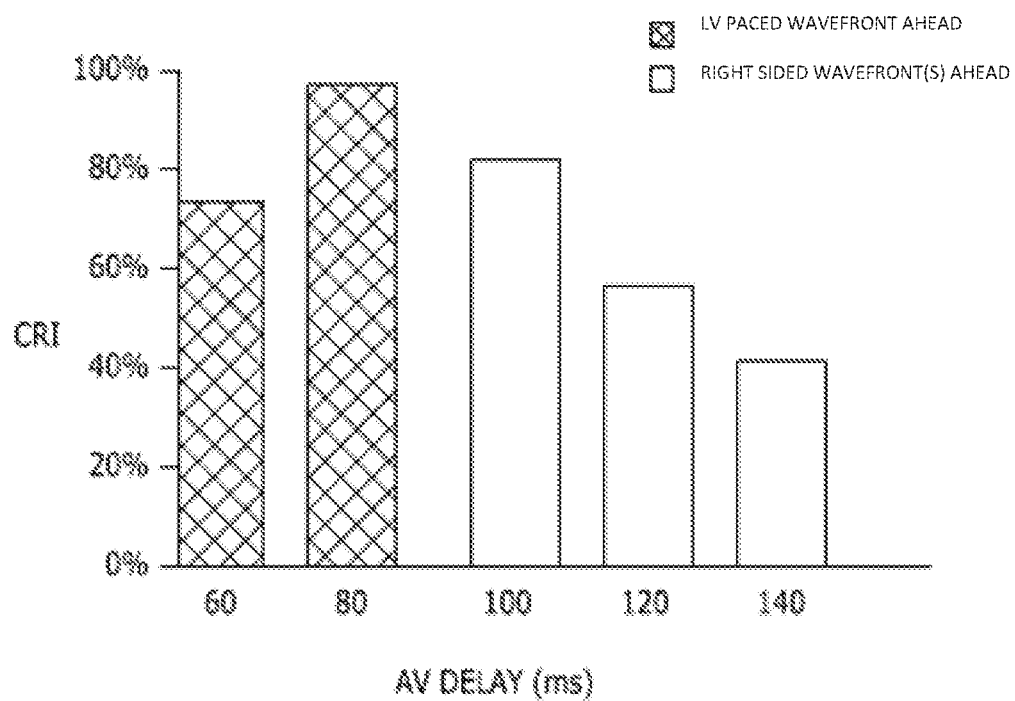
FIG. 24D

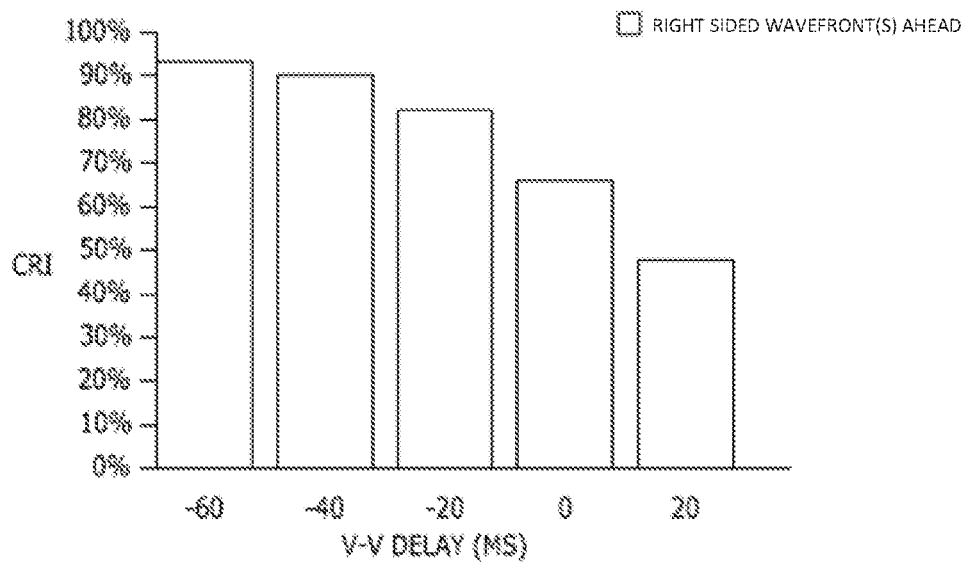
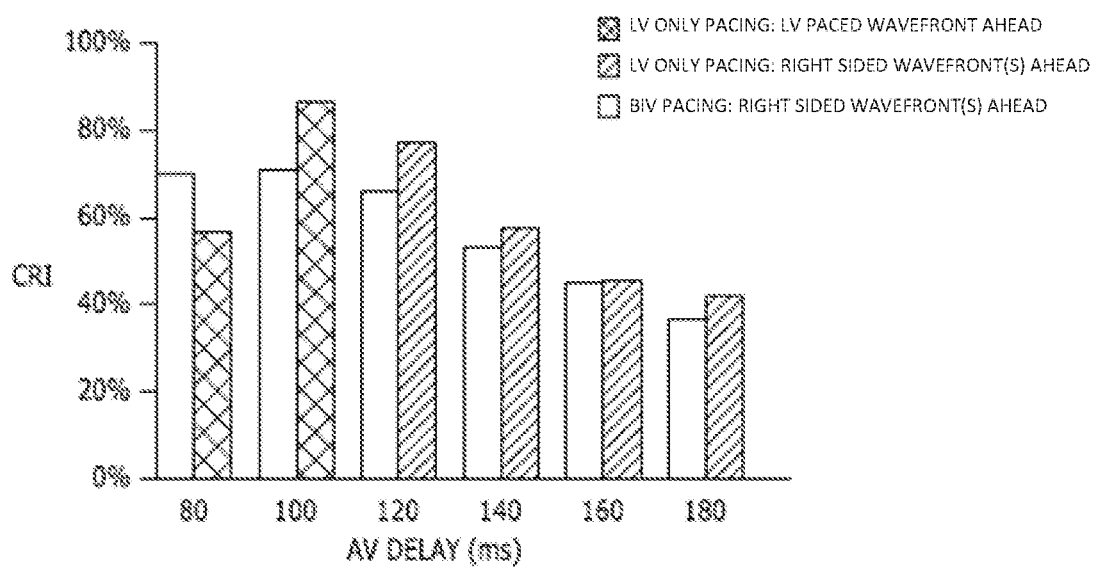
FIG. 26A

FIG. 29

SYSTEMS AND METHODS FOR OPTIMIZING IMPLANTABLE MEDICAL DEVICE CHARACTERISTICS USING DATA STRUCTURES AND GRAPHICAL REPRESENTATIONS

TECHNICAL FIELD

Embodiments of the present disclosure generally relate to systems and methods for improving and/or optimizing implantable medical device performance. For example, some embodiments of the present disclosure relate to systems and methods for determining implantable medical device parameters and administering cardiac resynchronization therapy using the parameters.

BACKGROUND OF THE DISCLOSURE

A heart failure may occur when a native signal (e.g., a signal indicating the heart muscles to beat or contract) does not propagate around a patient's heart properly. For example, a blockage, such as a right bundle branch block (RBBB) or a left bundle branch block (LBBB), may cause the native signal to be delayed and/or blocked when traversing through the heart. This may cause the heart to beat out of synch (e.g., electrical dyssynchrony). For example, in LBBB occurrences, the left ventricle may receive the native signal later than the right ventricle, which may cause the muscles of the left ventricle to beat after the muscles of the right ventricle.

An implantable medical device (IMD), such as a pacemaker, may be used to correct electrical dyssynchrony of the patient's heart. For example, the pacemaker may include multiple different leads, such as a left ventricle lead, a right ventricle lead, and/or a right atrium lead. The leads may include one or more electrodes that provide electrical signals to cause different portions of the heart to beat. By using these leads, the pacemaker may simulate the native signal to correct the electrical dyssynchrony.

However, electrical dyssynchrony may be different for each patient. Traditionally, due to the difficulty of measuring electrical dyssynchrony of the patient, the IMD is implanted with baseline or standard device settings (e.g., cardiac resynchronization therapy (CRT) settings). In some examples, these baseline settings might not be optimal for the patient and might not substantially improve the electrical dyssynchrony of the patient's heart.

For instance, CRT works by improving electrical and then mechanical dyssynchrony. A number of studies in animals and humans with LBBB have shown that this improvement in electrical dyssynchrony is a result of fusing a left-ventricle-paced (LV-paced) electrical wavefront moving anteriorly and rightward with right ventricle-paced (RV-paced) and/or native wavefronts moving posteriorly and leftward. This fusion can be identified by changes in QRS duration, amplitude and morphology that are a result of destructive interference from opposing wavefronts cancelling each other. Changes in atrial-ventricular (AV) delay, ventricular-ventricular (VV) delay, and pacing mode (biventricular (BiV) vs left ventricular (LV) only) impact the contribution of different wavefronts to fusion and cancellation. Although 12-lead ECG has been used to detect wavefront fusion and cancellation and assist in programming CRT settings, no methodology to determine the individualized CRT settings has been accepted and widely used in routine clinical care. In fact, the vast majority of CRT patients do not even undergo an optimization procedure and are kept at device settings programmed at implant. Accordingly, there exists a need for one or more improved methods and/or systems in order to address one or more of the above-noted drawbacks.

SUMMARY

The exemplary systems, methods, and interfaces described herein may be configured to assist a user (e.g., a physician) in evaluating a patient and/or evaluating cardiac therapy (e.g., cardiac therapy being performed on a patient during and/or after implantation of cardiac therapy apparatus). In one or more embodiments, the systems, methods, and interfaces may be used to determine a new way of measuring wavefront fusion and cancellation, which is called cardiac resynchronization index (CRI). CRI values indicate wavefront fusion and cancellation by using measurement electrodes to measure a single variable that reflects changes in the morphology, width, and dominant wavefront direction of the anterior and posterior electrode measurements at any IMD characteristic/setting as compared to native conduction. Comparison of electrogram morphology and CRI at different device settings allows for assessment of the relative contributions of native, RV and LV wavefronts to electrical fusion during CRT. By using this, the systems and methods may provide a non-invasive, practical, and physiologic approach that may be used to individualize (e.g., for a particular patient) and optimize CRT device programming.

In Example 1, a system for cardiac resynchronization of a patient is provided. The system comprises one or more processors in communication with a plurality of measurement electrodes operatively coupled to the patient and a tangible, non-transitory storage medium. The tangible, non-transitory storage medium comprising instructions that, when executed by the one or more processors, cause the one or more processors to receive, from the plurality of measurement electrodes, a first set of electrical measurements indicating first electrical signals applied to the patient's heart, receive one or more input variables, based on the one or more input variables, determine information corresponding to a data structure and indicating delays associated with an atrium lead, a left ventricle (LV) lead, and a right ventricle (RV) lead, determine a plurality of individualized characteristics based on the information corresponding to the data structure, based on the plurality of individualized characteristics, receive, from the plurality of measurement electrodes, a plurality of second sets of electrical measurements indicating second electrical signals applied to the patient's heart, determine cardiac resynchronization index (CRI) values using the first set of electrical measurements and the plurality of second sets of electrical measurements, populate the data structure based on the CRI values and the information indicating the delays, generate a graphical representation based on the populated data structure, and cause display of the graphical representation corresponding to the populated data structure on a display device.

In Example 2, the system of Example 1, wherein the information corresponding to the data structure indicates a plurality of entries, wherein each entry of the plurality of entries is associated with a first delay characteristic of a right atrium (RA) lead of the 1 MB to a left ventricle (LV) lead of the IMD and a second delay characteristic of the RA lead of the IMD to a right ventricle (RV) lead of the 1 MB.

In Example 3, the system of Example 2, wherein a first subset of the plurality of entries is associated with a plurality of LV lead only delay characteristics, and wherein a second subset of the plurality of entries is associated with a plurality of bi-ventricular (BiV) lead characteristics without ventricular-ventricular (VV) delay characteristic.

In Example 4, the system of Example 2, wherein a first subset of the plurality of entries is associated with a first priority, and wherein the determining the plurality of individualized characteristics comprises filtering the plurality of entries based on the first priority.

In Example 5, the system of Example 4, wherein a second subset of the plurality of entries is associated with a second priority, and wherein the determining the plurality of individualized characteristics further comprises, receiving user input indicating the second priority, and including the second subset of the plurality of entries corresponding to the second priority to the plurality of individualized characteristics.

In Example 6, the system of Example 4, wherein the determining the plurality of individualized characteristics further comprises receiving user input indicating one or more entries from the plurality of entries, and including the one or more entries from the plurality of entries to the plurality of individualized characteristics.

In Example 7, the system of Example 2, wherein the generating the graphical representation based on the populated data structure comprises generating a heat map based on the determined CRI values, the first delay characteristic, and the second delay characteristic.

In Example 8, the system of Example 7, wherein the causing display of the graphical representation comprises causing display of the heat map and one or more visual indicia, wherein the one or more visual indicia indicates at least one optimal cardiac resynchronization therapy (CRT) treatment corresponding to an individualized characteristic from the plurality of individualized characteristics.

In Example 9, the system of Example 1, wherein the one or more input variables indicate a patient category corresponding to a condition of the patient's heart, and wherein the determining the information corresponding to the data structure and indicating the delays is based on the patient category.

In Example 10, the system of Example 1, wherein the one or more input variables indicate a device type of the 1 MB, and wherein the determining the information corresponding to the data structure and indicating the delays is based on the device type of the IMD.

In Example 11, the system of Example 1, wherein the tangible, non-transitory storage medium further comprises instructions that, when executed by the one or more processors, cause the one or more processors to determine new information corresponding to the data structure and indicating the delays, wherein the new information indicates to operate the 1 MB in a different mode, receive, from the plurality of measurement electrodes and based on the new information indicating to operate the IMD in the different mode, a plurality of third sets of electrical measurements indicating third electrical signals applied to the patient's heart, determine new CRI values using the first set of electrical measurements and the plurality of third sets of electrical measurements, populate the data structure based on the new CRI values and the new information, generate a new graphical representation based on the populated data structure, and cause display of the new graphical representation on the display device.

In Example 12, the system of Example 11, wherein new information indicates new delays corresponding to the atrium lead, the LV lead, and the RV lead.

In Example 13, the system of Example 11, wherein the new information indicating to operate the IMD in the different mode comprises switching the 1 MB from an atrial sensing mode to an atrial pacing mode.

In Example 14, the system of Example 11, wherein the new information indicating to operate the IMD in the different mode comprises switching the 1 MB from an atrial pacing mode to an atrial sensing mode.

In Example 15, the system of Example 11, wherein the new information indicating to operate the 1 MB in the different mode comprises switching the IMD from a first electrode vector corresponding to a first electrode of a left ventricle (LV) lead to a second electrode vector corresponding to a second electrode of the LV lead.

In Example 16, the system of Example 11, wherein the tangible, non-transitory storage medium further comprises instructions that, when executed by the one or more processors, cause the one or more processors to determine the CRI values and the new CRI values are below a threshold, and based on the CRI values and the new CRI values being below the threshold, cause display of a prompt indicating the LV lead is in a sub-optimal position.

In Example 17, a method for cardiac resynchronization of a patient is provided. The method comprises receiving, from a plurality of measurement electrodes, a first set of electrical measurements indicating first electrical signals applied to the patient's heart, receiving one or more input variables, based on the one or more input variables, determining information corresponding to a data structure and indicating delays associated with an atrium lead, a left ventricle (LV) lead, and a right ventricle (RV) lead, determining a plurality of individualized characteristics based on the information corresponding to the data structure, based on the plurality of individualized characteristics, receiving, from the plurality of measurement electrodes, a plurality of second sets of electrical measurements indicating second electrical signals applied to the patient's heart, determining cardiac resynchronization index (CRI) values using the first set of electrical measurements and the plurality of second sets of electrical measurements, populating the data structure based on the CRI values and the information indicating the delays, generating a graphical representation based on the populated data structure, causing display of the graphical representation corresponding to the populated data structure on a display device.

In Example 18, the method of Example 17, wherein the information corresponding to the data structure indicates a plurality of entries, wherein each entry of the plurality of entries is associated with a first delay characteristic of a right atrium (RA) lead of the 1 MB to a left ventricle (LV) lead of the IMD and a second delay characteristic of the RA lead of the IMD to a right ventricle (RV) lead of the 1 MB.

In Example 19, a non-transitory computer readable medium is provided. The non-transitory computer readable medium stores instructions for execution by one or more processors incorporated into a system, wherein execution of the instructions by the one or more processors cause the one or more processors to receive, from a plurality of measurement electrodes, a first set of electrical measurements indicating first electrical signals applied to the patient's heart, receive one or more input variables, based on the one or more input variables, determine information corresponding to a data structure and indicating delays associated with an atrium lead, a left ventricle (LV) lead, and a right ventricle (RV) lead, determine a plurality of individualized characteristics based on the information corresponding to the data structure, based on the plurality of individualized characteristics, receive, from the plurality of measurement electrodes, a plurality of second sets of electrical measurements indicating second electrical signals applied to the patient's heart, determine cardiac resynchronization index (CRI) values using the first set of electrical measurements and the plurality of second sets of electrical measurements, populate the data structure based on the CRI values and the information indicating the delays, generate a graphical representation based on the populated data structure, and cause display of the graphical representation corresponding to the populated data structure on a display device.

In Example 20, the non-transitory computer readable medium of Example 19, wherein the information corresponding to the data structure indicates a plurality of entries, wherein each entry of the plurality of entries is associated with a first delay characteristic of a right atrium (RA) lead of the IMD to a left ventricle (LV) lead of the IMD and a second delay characteristic of the RA lead of the IMD to a right ventricle (RV) lead of the IMD.

The exemplary systems, methods, and interfaces described herein may be configured to assist a user (e.g., a physician) in evaluating a patient and/or evaluating cardiac therapy (e.g., cardiac therapy being performed on a patient during and/or after implantation of cardiac therapy apparatus). In one or more embodiments, the systems, methods, and interfaces may be used to determine a new way of measuring wavefront fusion and cancellation, which is called cardiac resynchronization index (CRI). CRI values indicate wavefront fusion and cancellation by using measurement electrodes to measure a single variable that reflects changes in the morphology, width, and dominant wavefront direction of the anterior and posterior electrode measurements at any IMD characteristic/setting as compared to native conduction. Comparison of electrogram morphology and CRI at different device settings allows for assessment of the relative contributions of native, RV and LV wavefronts to electrical fusion during CRT. By using this, the systems and methods may provide a non-invasive, practical, and physiologic approach that may be used to individualize (e.g., for a particular patient) and optimize CRT device programming.

In Example 21, a system for cardiac resynchronization of a patient is provided. The system comprises one or more processors in communication with a plurality of measurement electrodes operatively coupled to the patient and a tangible, non-transitory storage medium. The tangible, non-transitory storage medium comprising instructions that, when executed by the one or more processors, cause the one or more processors to receive, from the plurality of measurement electrodes, a first set of electrical measurements indicating native electrical energy applied to the patient's heart, receive, from the plurality of measurement electrodes, a plurality of second sets of electrical measurements indicating the native electrical energy applied to the patient's heart and electrical energy applied by at least one lead to the patient's heart, each of the plurality of second sets of electrical measurements corresponding to a different characteristic, determine a first electrical dyssynchrony value based on the first set of electrical measurements, determine a plurality of second electrical dyssynchrony values based on the plurality of second sets of electrical measurements, determine a plurality of cardiac resynchronization index values based on comparisons of the first set of electrical measurements and the plurality of second sets of electrical measurements, and provide information for administering cardiac resynchronization therapy (CRT) based on the plurality of cardiac resynchronization index values.

In Example 22, the system of Example 21, the system further comprising a display device, and wherein the providing the information comprises providing one or more instructions to cause display of at least one of the plurality of cardiac resynchronization index values on the display device.

In Example 23, the system of Example 21, wherein the at least one lead comprises a left lead operatively coupled to a left portion of the patient's heart, and wherein receiving the first set of electrical measurements comprises receiving the first set of electrical measurements indicating electrical characteristics of the patient's heart without the left lead providing electrical energy to the patient's heart.

In Example 24, the system of Example 23, wherein receiving the plurality of second sets of electrical measurements comprises receiving the plurality of second sets of electrical measurements indicating the electrical characteristics of the patient's heart with the left lead providing electrical energy to the patient's heart.

In Example 25, the system of Example 21, wherein the at least one lead comprises a left lead operatively coupled to a left portion of the patient's heart and a right lead operatively coupled to a right portion of the patient's heart, and wherein receiving the plurality of second sets of electrical measurements comprises receiving the plurality of second sets of electrical measurements indicating electrical characteristics of the patient's heart with the left lead and the right lead providing electrical energy to the patient's heart.

In Example 26, the system of Example 21, wherein the tangible, non-transitory storage medium further comprises instructions that, when executed by the one or more processors, cause the one or more processors to determine, based on the first set of electrical measurements, a plurality of characteristics to apply to the at least one lead based on the first set of electrical measurements, wherein the plurality of characteristics comprises each of the different characteristics, and wherein receiving the plurality of second sets of electrical measurements is based on the plurality of characteristics.

In Example 27, the system of Example 26, wherein the at least one lead comprises a left lead operatively coupled to a left portion of the patient's heart and a right lead operatively coupled to a right portion of the patient's heart, and wherein the plurality of characteristics comprises a plurality of atrial-ventricular (AV) delays.

In Example 28, the system of Example 27, wherein the plurality of AV delays corresponds to a plurality of left ventricle (LV) delays for the left lead to apply the electrical energy to the patient's heart.

In Example 29, the system of Example 27, wherein the plurality of AV delays corresponds to a plurality of biventricular (BiV) delays for the left lead and the right lead to apply the electrical energy to the patient's heart.

In Example 30, the system of Example 26, wherein the at least one lead comprises a left lead operatively coupled to a left portion of the patient's heart and a right lead operatively coupled to a right portion of the patient's heart, and wherein the plurality of characteristics comprises a plurality of ventricular-ventricular (VV) delays.

In Example 31, the system of Example 21, wherein the plurality of measurement electrodes is less than 40 electrodes.

In Example 32, the system of Example 31, wherein the plurality of measurement electrodes is less than 20 electrodes.

In Example 33, the system of Example 31, wherein the plurality of measurement electrodes comprises a plurality of anterior electrodes and a plurality of posterior electrodes, and wherein the plurality of anterior electrodes is less than ten electrodes and the plurality of posterior electrodes is less than 10 electrodes.

In Example 34, a system for cardiac resynchronization of a patient is provided. The system comprises one or more processors in communication with a plurality of measurement electrodes operatively coupled to the patient and a tangible, non-transitory storage medium. The tangible, non-transitory storage medium comprising instructions that, when executed by the one or more processors, cause the one or more processors to receive, from the plurality of measurement electrodes, a first set of electrical measurements indicating first electrical signals applied to the patient's heart, in response to providing one or more first instructions to an implantable medical device indicating a plurality of parameters for at least one lead, receive, from the plurality of measurement electrodes, a plurality of second sets of electrical measurements indicating second electrical signals applied to the patient's heart, determine a plurality of cardiac resynchronization index values based on comparing the first set of electrical measurements with the plurality of second sets of electrical measurements, determine an optimized parameter, from the plurality of parameters, based on the plurality of cardiac resynchronization index values, and provide, to the implantable medical device, one or more second instructions to administer cardiac resynchronization therapy (CRT) based on the optimized parameter.

In Example 35, the system of Example 34, wherein the at least one lead comprises a left ventricle lead operatively coupled to a left ventricle of the patient's heart and a right ventricle lead operatively coupled to a right ventricle of the patient's heart, and wherein the tangible, non-transitory storage medium further comprises instructions that, when executed by the one or more processors, cause the one or more processors to provide, to the implantable medical device, one or more third instructions to cause the implantable medical device to provide no electrical energy to the left ventricle lead and the right ventricle lead, and wherein receiving the first set of electrical measurements is based on providing the one or more third instructions.

In Example 36, the system of Example 34, wherein each of the plurality of second sets of electrical measurements is associated with a different parameter from the plurality of parameters.

In Example 37, the system of Example 36, wherein the at least one lead comprises a left ventricle lead operatively coupled to a left ventricle of the patient's heart, and wherein the plurality of parameters comprises a plurality of atrial-ventricular (AV) time delays for the left ventricle lead.

In Example 38, the system of Example 36, wherein the at least one lead comprises a left ventricle lead operatively coupled to a left ventricle of the patient's heart and a right ventricle lead operatively coupled to a right ventricle of the patient's heart, and wherein the plurality of parameters comprises a plurality of atrial-ventricular (AV) time delays for the left ventricle lead and the right ventricle lead.

In Example 39, the system of Example 36, wherein the at least one lead comprises a left ventricle lead operatively coupled to a left ventricle of the patient's heart and a right ventricle lead operatively coupled to a right ventricle of the patient's heart, and wherein the plurality of parameters comprises an atrial-ventricular time delay and a plurality of ventricular-ventricular (VV) time delays for the left ventricle lead and the right ventricle lead.

In Example 40, the system of Example 36, wherein determining the plurality of cardiac resynchronization index values comprises determining a first dyssynchrony measurement for the first set of electrical measurements, determining a plurality of second dyssynchrony measurements for each of the plurality of second sets of electrical measurements, and determining the plurality of cardiac resynchronization index values based on comparing the first dyssynchrony measurement with each of the plurality of second dyssynchrony measurements.

In Example 41, the system of Example 40, wherein the plurality of measurement electrodes comprises a plurality of anterior electrodes and a plurality of posterior electrodes, wherein the first set of electrical measurements comprises a plurality of anterior measurements from the plurality of anterior electrodes and a plurality of posterior measurements from the plurality of posterior electrodes, and wherein determining the first dyssynchrony measurement is based on comparing the plurality of anterior measurements with the plurality of posterior measurements.

In Example 42, the system of Example 40, wherein the plurality of measurement electrodes comprises a plurality of anterior electrodes and a plurality of posterior electrodes, wherein each of the plurality of second sets of electrical measurements comprises a plurality of anterior measurements from the plurality of anterior electrodes and a plurality of posterior measurements from the plurality of posterior electrodes, and wherein determining each of the plurality of second dyssynchrony measurements is based on comparing the corresponding second dyssynchrony measurement with the first dyssynchrony measurement.

In Example 43, the system of Example 34, wherein the at least one lead comprises one or more electrodes, and wherein all of the one or more electrodes provides the second electrical signals.

In Example 44, the system of Example 34, wherein the at least one lead comprises one or more electrodes, and wherein at least one of the one or more electrodes provides the second electrical signals.

In Example 45, a system for cardiac resynchronization of a patient is provided. The system comprises one or more processors in communication with a plurality of measurement electrodes operatively coupled to the patient, a display device in communication with the one or more processors, and a tangible, non-transitory storage medium. The tangible, non-transitory storage medium comprising instructions that, when executed by the one or more processors, cause the one or more processors to receive, from the plurality of measurement electrodes, a first set of electrical measurements indicating electrical characteristics of the patient's heart without at least one lead from an implantable medical device providing electrical energy to the patient's heart, receive, from the plurality of measurement electrodes, a plurality of second sets of electrical measurements indicating electrical characteristics of the patient's heart with the at least one lead providing electrical energy to the patient's heart, each of the plurality of second sets of electrical measurements indicating a different characteristic for the implantable medical device, determine a plurality of cardiac resynchronization index values based on comparing the first set of electrical measurements with the plurality of second sets of electrical measurements, wherein the plurality of cardiac resynchronization index values corresponds to the different characteristics for the implantable medical device, and cause display of an image on the display device, the image indicating the plurality of cardiac resynchronization index values.

In Example 46, the system of Example 45, wherein the different characteristics comprises a plurality of atrial-ventricular (AV) delays, wherein the image comprises a graphical representation of the plurality of cardiac resynchronization index values with the plurality of AV delays, and wherein each of the plurality of cardiac resynchronization index values has a corresponding AV delay from the plurality of AV delays.

In Example 47, the system of Example 45, wherein the different characteristics comprises a plurality of Bi-ventricular (BiV) delays and a plurality of left ventricular lead only (LV-only) delays, wherein the image comprises a graphical representation of the plurality of cardiac resynchronization index values with the plurality of Bi-V delays and the plurality of LV-only delays, and wherein each of the plurality of cardiac resynchronization index values has a corresponding Bi-V delays from the plurality of Bi-V delays or a corresponding LV-only delay from the plurality of LV-only delays.

In Example 48, the system of Example 45, wherein the different characteristics comprises a plurality of ventricular-ventricular (VV) delays, wherein the image comprises a graphical representation of the plurality of cardiac resynchronization index values with the plurality of VV delays, and wherein each of the plurality of cardiac resynchronization index values has a corresponding VV delay from the plurality of VV delays.

In Example 49, the system of Example 45, wherein the image comprises a graphical representation of a first signal from a left lead of the implantable medical device, a second signal from a right lead of the implantable medical device, and a third signal corresponding to a native signal of the patient's heart.

In Example 50, the system of Example 49, wherein the causing display of the image on the display device comprises causing display of an animation of a first wavefront, second wavefront, and third wavefront propagating through a second graphical representation of the patient's heart, wherein the first wavefront corresponds to the first signal, wherein the second wavefront corresponds to the second signal, and, wherein the third wavefront corresponds to the third signal.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The embodiments will be more readily understood in view of the following description when accompanied by the below figures and wherein like reference numerals represent like elements, wherein:

FIG. 12 is an exemplary graphical user interface depicting measurements from the measurement electrodes of the electrode apparatus;

FIG. 21 is an exemplary diagram of different VV delay methods;

FIGS. 23A-E show depictions of electrograms and CRI graphical representations for multiple patients with complete heart blockage (CHD) over a range of VV delays;

FIGS. 24A-E show depictions of electrograms and CRI graphical representations for multiple patients during LV only pacing over a range of AV delays;

FIGS. 26A-D show depictions of electrograms and CRI graphical representations for a single patient over a range of AV delays and VV delays;

FIG. 29 is another exemplary graphical user interface depicting a data structure used to determine optimal CRT treatments;

Figure 1:
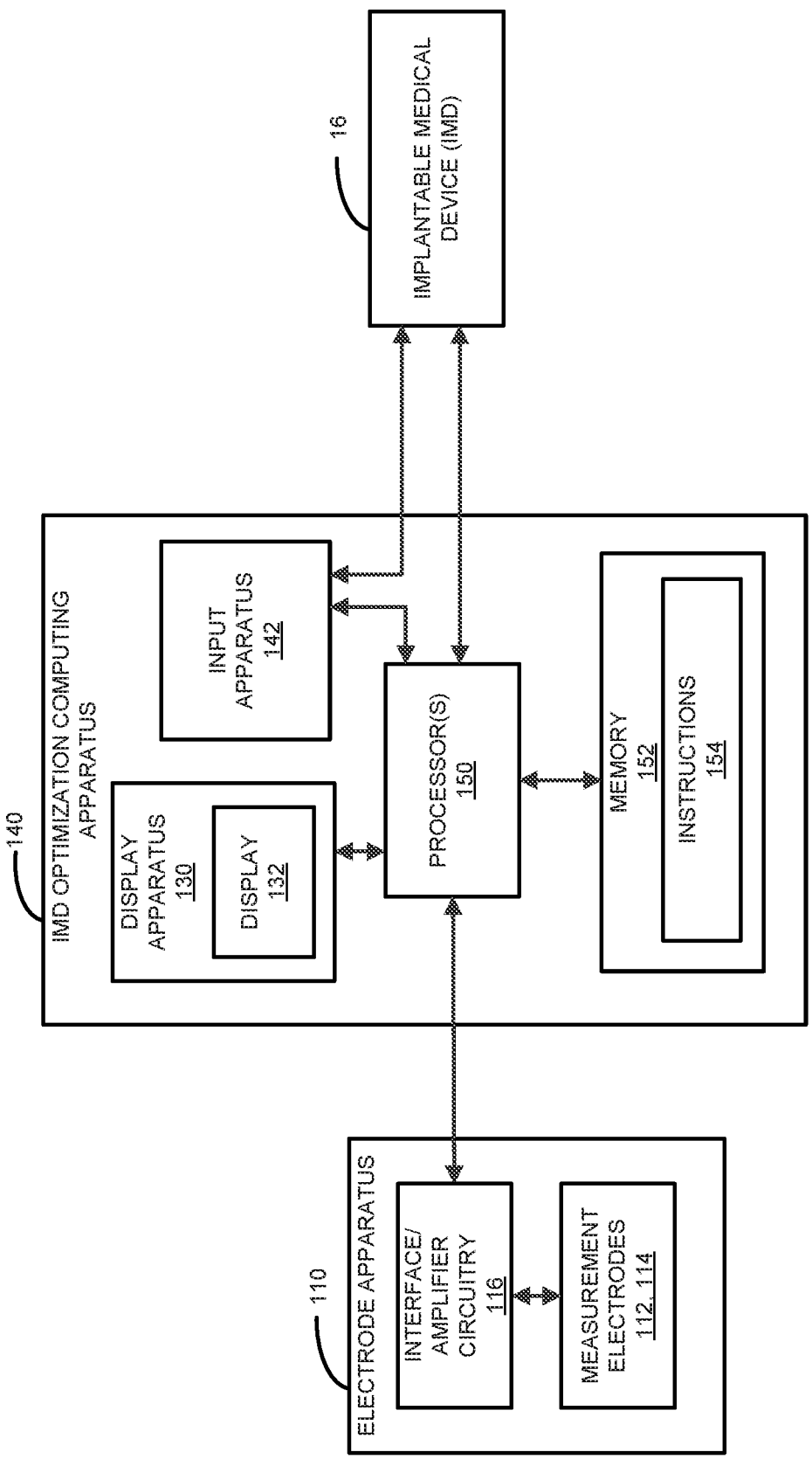
FIG. 1 is a diagram of an exemplary system including an electrode apparatus, an implantable medical device (IMD) optimization computing apparatus, and an implantable medical device.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION OF EMBODIMENTS

FIG. 1 shows one example of an implantable medical device (IMD) optimization system 100 for cardiac resynchronization and/or optimizing IMD characteristics. In some instances, the system 100 includes an electrode apparatus 110, an IMD optimization computing apparatus 140, and an IMD 16. The electrode apparatus 110 may include one or more measurement electrodes 112 and/or 114. The measurement electrodes 112, 114 and/or the electrode apparatus 110 may be any device, apparatus, or component that detects electrical information (e.g., cardiac electrical activation signals and/or electrocardiogram (ECG) signals) of the patient. In some instances, the electrode apparatus 100 may be an ECG sensor that detects, measures, and/or estimates cardiac electrical activation signals in proximity to a reference location. Such electrical activation signals may be measured and displayed, or conveyed, to a computing apparatus, such as the computing apparatus 140. For example, the electrode apparatus 110 may acquire the ECG signals from the measurement electrodes 112, 114 and generate the metric of electrical activation signals (e.g., depolarization and/or repolarization of the patient's heart) measured from various ECG locations (e.g., the locations of the measurement electrodes 112, 114). By using the electrode apparatus 100, a user (e.g., a physician) may evaluate a patient's cardiac condition and/or administer cardiac resynchronization therapy to the patient.

In some instances, the electrode apparatus 110 is operatively coupled to the computing apparatus 140 (e.g., through one or wired electrical connections, wirelessly, etc.) and/or provides information such as electrical signals (e.g., body-surface potentials) from each of the measurement electrodes 112, 114 to the computing apparatus 140 for analysis, evaluation, etc.

The IMD 16 is any type of implantable device used to assist with electrical dyssynchrony. In some instances, the IMD 16 is a pacemaker that includes one or more leads. Each lead may include one or more electrodes that provide pacing therapy (e.g., pacing pulses) to the patient. For example, the electrodes may be operatively coupled to a patient's heart and may provide pacing pulses to assist in depolarization and/or repolarization of the heart. In some instances, the IMD 16 is operatively coupled to the computing apparatus 140 (e.g., through one or wired electrical connections, wirelessly, etc.). The computing apparatus 140 may provide instructions, commands, and/or other types of information to the IMD 16. Additionally, and/or alternatively, the IMD 16 may provide feedback information to the computing apparatus 140. The IMD 16 will be described in further detail below.

The IMD optimization computing apparatus 140 is any type of computing apparatus suitable for implementing aspects of embodiments of the disclosed subject matter. Examples of computing apparatus 140 include but are not limited to workstations, laptops, desktops, tablet computers, hand-held devices, display devices, servers, cloud computing platforms and the like, all of which are contemplated within the scope of FIG. 1.

In some embodiments, the computing apparatus 140 includes one or more processors 150 that executes instructions 154 (e.g., code) stored in memory 152 (e.g., non-transitory storage medium). The computing apparatus 140 may also include other components such as one or more buses that interact one or more components within the computing apparatus 140, one or more communication ports (wired and/or wireless), a display apparatus 130, a display 132, and/or an input apparatus 142.

The processor 150 may be configured to analyze data such as the electrical information from the electrode apparatus 110, cardiac information representative of at least one of mechanical cardiac functionality, and/or electrical cardiac functionality. Cardiac information may include electrical heterogeneity information or electrical dyssynchrony information, body surface cardiac activation information, surrogate cardiac electrical activation information or data, that is generated using electrical signals (e.g., body-surface potentials) gathered, monitored, or collected, using the electrode apparatus 110.

The computing apparatus 140 may be configured to receive input from input apparatus 142 and transmit output to the display apparatus 130. For example, based on analyzing the data, the processor 150 may provide information to the display apparatus 130. The display apparatus 130 may include a display 132 that may be configured to display the data to the user and/or the patient.

Further, the computing apparatus 140 may include data storage (e.g., memory 152) that may allow for access to processing programs or routines and/or one or more other types of data, e.g., for driving a graphical user interface configured to noninvasively assist the user in evaluating, selecting, and/or determining cardiac therapy settings (e.g., the location of an implantable electrode used for pacing, the location of pacing therapy delivered by a particular pacing vector, type of pacing therapy such as biventricular pacing, and left ventricular-only pacing, and various timings of pacing therapy such as atrial-ventricular (AV) delay, ventricular-ventricular (VV) delay, pulse width, and/or voltage).

The computing apparatus 140 may include the input apparatus 142 and/or the display apparatus 130. In other words, the processor 150 may transmit and/or receive data from the input apparatus 142 and/or the display apparatus 130. In some examples, the computing apparatus 140 may be separate from the input apparatus 142 and/or the display apparatus 130. In other words, the computing apparatus 140 may be electrically coupled to the input apparatus 142 and/or the display apparatus 130 via one or more analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 and to view and/or select one or more pieces of information related to the cardiac therapy.

In some variations, the input apparatus 142 is a keyboard. However, it should be understood that the input apparatus 142 may be any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 and/or display 132 may include any apparatus, including a graphical user interface, capable of displaying information to a user. The information displayed by the display apparatus 130 may include cardiac information, textual instructions, graphical depictions of electrical activation information, graphical depictions of a plurality of signals including anterior and posterior electrode signals, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130 may include a liquid crystal display, an organic light-emitting diode screen, a touchscreen, a cathode ray tube display, etc.

The processing programs or routines stored and/or executed by the computing apparatus 140 may include programs or routines for computational mathematics, matrix mathematics, dispersion determinations (e.g. standard deviations, distances, areas under the curve, variances, ranges, interquartile ranges, mean absolute differences, average absolute deviations, etc.), filtering algorithms, maximum value determinations, minimum value determinations, threshold determinations, moving windowing algorithms, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more exemplary methods and/or processes described herein. Data stored and/or used by the computing apparatus 140 may include, for example, electrical signal/waveform data from the electrode apparatus 110 (such as, e.g., anterior and posterior electrode signals over a plurality of cardiac cycles, over a single cardiac cycles, over various slices of time, etc.), parts or portions of various signals, electrical activation times from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

In some instances, the computing apparatus 140 may be, for example, any fixed or mobile computer system (e.g., a controller, a microcontroller, a personal computer, minicomputer, tablet computer, etc.) and may be generally described as including processing circuitry. The exact configuration of the computing apparatus 140 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable medium such as a disk or tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

As mentioned above, the electrode apparatus 110 may monitor electrical signal activity of the patient's heart and may include multiple measurement electrodes 112 and 114. For example, the electrode apparatus 110 may be configured to measure electrical information (e.g., electrical signals)

representing different regions of a patient's heart and may provide the electrical information to the computing apparatus 140.

Figure 2:
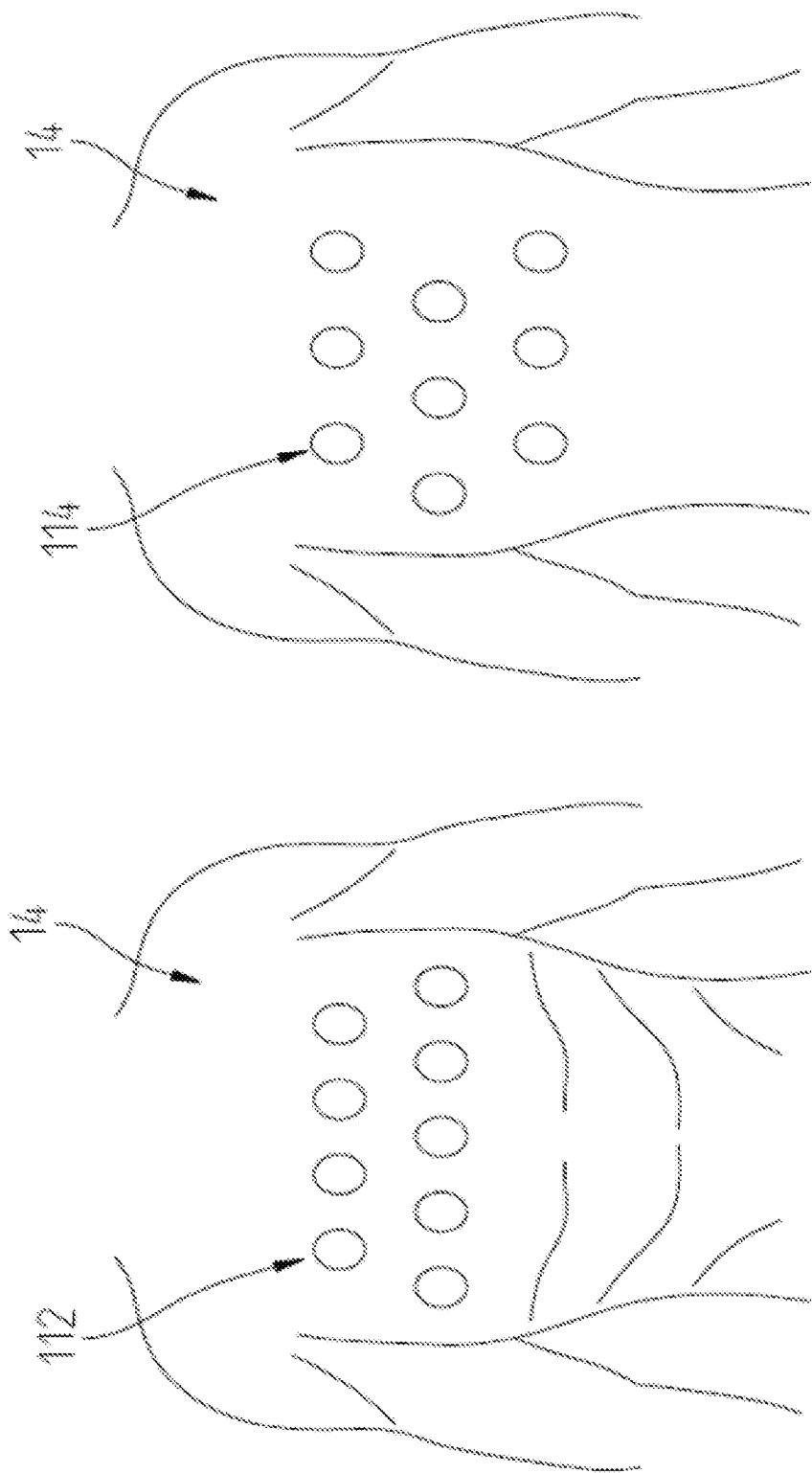
FIG. 2 is a diagram of an exemplary electrode configuration for the electrode apparatus.

In some examples, the electrical information may include surface electrocardiogram (ECG) signals measured using measurement electrodes 112 and 114 in proximity to surface areas corresponding to the patient and/or the patient's heart. FIG. 2 shows an exemplary electrode configuration for the measurement electrodes 112 and 114 for the electrode apparatus 100. As shown, the electrode apparatus 110 includes two sets of electrodes such as a first set or anterior electrodes 112 (e.g., electrodes located at the anterior or front of the patient 14) and a second set or posterior electrodes 114 (e.g., electrodes located at the posterior or rear of the patient 14).

The electrodes 112 and 114 may be attached, or coupled, to one or more leads. The leads may be attached or coupled to the electrode apparatus 100. As shown, the electrodes 112 and 114 are proximately located around the torso of a patient 14 such that the electrodes 112 and 114 surround the patient's heart. The electrodes 112 and 114 may be positioned proximate the tissue (e.g., skin) of the patient to acquire electrical signals or activity (e.g., body-surface potentials). In other words, the electrodes 112 and 114 may be positioned near or operably in contact with the tissue of the patient so as to be able to sense electrical signals or activity (e.g., body-surface potentials). Further, the electrodes 112 and 114 may be described as being "on" and/or secured to the skin of the patient. Still further, the electrodes 112 and 114 may be attached to the tissue of the patient using a conductive adhesive such as a conductive adhesive layer. Also, the conductive adhesive and/or conductive adhesive layer may include conductive gel.

In some examples, the electrode apparatus 110 may include interface/amplifier circuitry 116. The interface/amplifier circuitry 116 may be configured to amplify the signals from the electrodes 112 and 114. The electrodes 112 and 114 may be electrically connected to the interface/amplifier circuitry 116. The interface/amplifier circuitry 116 may be electrically connected and provide the signals from the electrodes 112 and 114 to the computing apparatus 140 via a wired connection. Other exemplary systems may use a wireless connection to transmit the signals sensed by electrodes 112 and 114 to the interface/amplifier circuitry 116 and, in turn, to the computing apparatus 140. Additionally, and/or alternatively, the interface/amplifier circuitry 116 may be electrically coupled to each of the computing apparatus 140 and the display apparatus 130 using analog electrical connections, digital electrical connections, wireless connections, bus-based connections, network-based connections, internet-based connections, etc. In some instances, the computing apparatus 140 may include the interface/amplifier circuitry 116. In some variations, the system 100 might not include the interface/amplifier circuitry 116. For example, the measurement electrodes 112, 114 may provide the signals to the processor 150 without amplifying the signals.

The configuration of the electrodes 112 and 114 may surround the heart of the patient 14. Further, the electrodes 112 and 114 may record or monitor the electrical signals associated with the depolarization and repolarization of the heart after the signals have propagated through the torso of the patient 14. Each of the electrodes 112 and 114 may be used in a unipolar configuration to sense the torso-surface potentials that reflect the cardiac signals. The interface/amplifier circuitry 116 may also be coupled to a return or indifferent electrode (not shown) that may be used in combination with each electrode 112 and/or 114 for unipolar sensing. In the exemplary embodiment of FIG. 2, there are 9 anterior electrodes 112 and 9 posterior electrodes 114. However, in other examples, the electrode apparatus 110 may include more or less than 18 total electrodes 112 and 114. For example, the electrode apparatus 110 may include between 8 to about 100 electrodes 112 and 114 spatially distributed around the torso of patient.

Additionally, and/or alternatively, in some instances, the electrode apparatus 110 includes a strap, belt, and/or a variety of mechanisms such as tape or adhesives that may be employed to aid in the spacing and placement of electrodes 112 and 114. In some examples, the strap may include an elastic band, strip of tape, or cloth. Further, in some examples, electrodes 112 and 114 (e.g., arranged in an array) may be part of, or located within, patches, vests, and/or other manners of securing the electrodes 112 and 114 to the torso of the patient 14.

The computing apparatus 140 may record and analyze the electrical information (e.g., torso-surface potential signals) sensed by electrodes 112, 114, and/or amplified/conditioned by the interface/amplifier circuitry 116. The computing apparatus 140 may be configured to analyze the signals from the electrodes 112 and 114 to determine the anterior and posterior electrode signals (e.g., the signals from the electrodes 112 and/or 114), body surface cardiac electrical activation times, and surrogate cardiac electrical activation times, e.g., representative of actual, or local, electrical activation times of one or more regions of the patient's heart as will be further described herein.

In some examples, the computing apparatus 140 may determine the activation times by measuring the period of time between an onset of cardiac depolarization (e.g., onset of QRS complex) and an appropriate fiducial point such as, e.g., a peak value, a minimum value, a minimum slope, a maximum slope, a zero crossing, a threshold crossing, etc. In one or more embodiments, activation times may be generally determined by measuring the time from the earliest onset time within electrical activity from a plurality of external electrodes over a cardiac cycle (e.g., a depolarization portion of the cardiac cycle, the QRS complex, etc.) to the steepest, or maximum, negative slope within the electrical activity monitored by the particular external electrode for which the activation time is being calculated for.

Additionally, the computing apparatus 140 may be configured to provide graphical user interfaces depicting the body surface cardiac electrical activation times and/or surrogate cardiac electrical activation times obtained using the electrode apparatus 110. Exemplary systems, methods, and/or interfaces may noninvasively use the electrical information collected using the electrode apparatus 110 to evaluate a patient's cardiac condition and/or cardiac therapy being delivered to the patient.

The electrode apparatus 110 and/or the computing apparatus 140 may be electrically connected to (e.g., wirelessly and/or wired) the IMD 16 and/or one or more leads of the IMD 16. The one or more leads of the IMD 16 may be located proximate one or more portions of a patient's heart. For example, the computing apparatus 140 may provide information, such as instructions or commands, to the 1 MB 16. The information may indicate one or more IMD 16 settings or characteristics (e.g., ventricular-ventricular (VV) delay and/or atrial-ventricular (AV) delay). Additionally, and/or alternatively, the IMD 16 may provide information to the computing apparatus 140 and/or the electrode apparatus 110.

Figure 3:
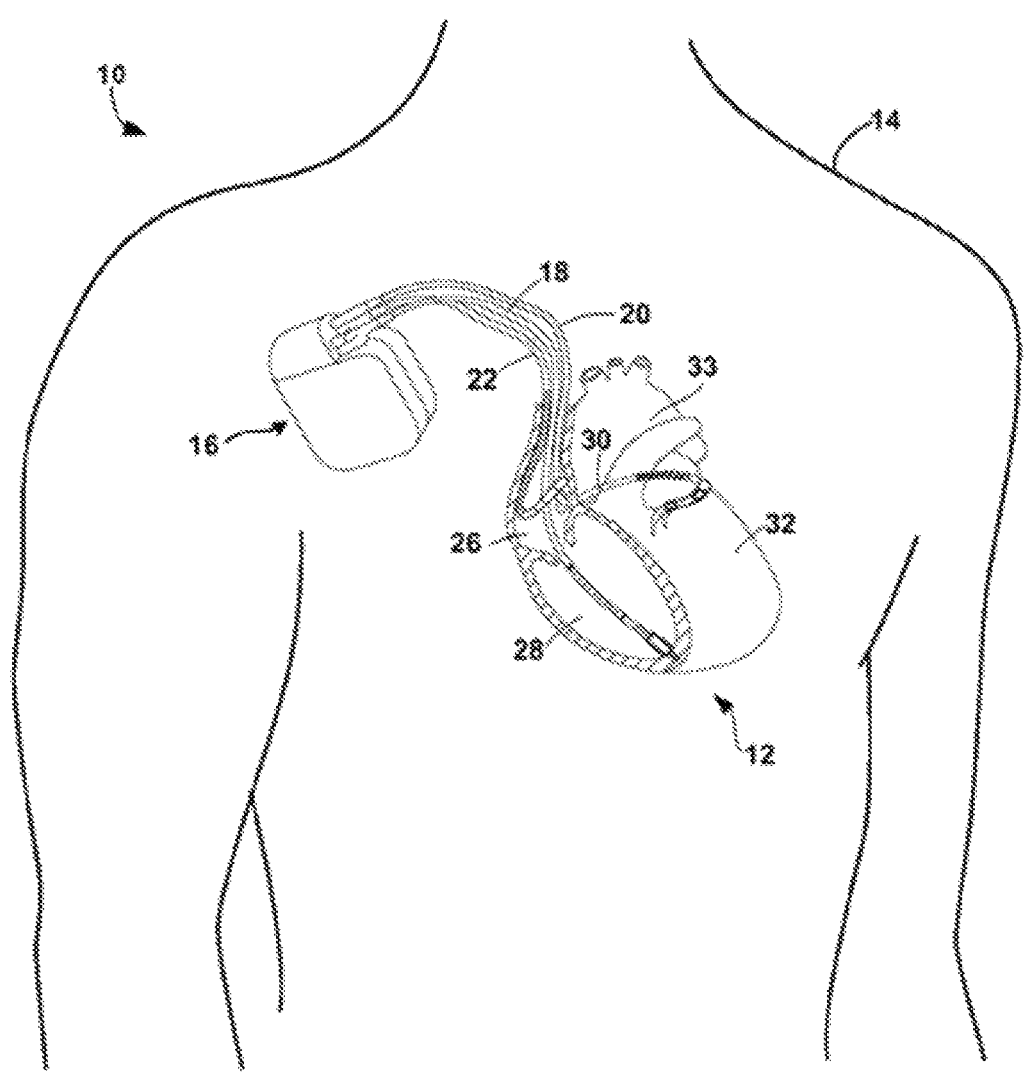
FIG. 3 is a diagram of an exemplary system including an exemplary IMD.

FIGS. 3-7 describe the exemplary IMD 16 of system 100 in more detail. FIG. 3 is a conceptual diagram illustrating an exemplary therapy system 10 that may be used to deliver pacing therapy to a patient 14 and includes the implantable medical device 16 (IMD). The 1 MB 16 may include and/or is coupled to leads 18, 20, 22. The IMD 16 may be, e.g., an implantable pacemaker, cardioverter, and/or defibrillator, that delivers, transmits, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 3, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMB 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The 1 MB 16 may be operable to adjust one or more parameters associated with the pacing therapy such as, e.g., AV delay, VV delay, other various timings/delays, pulse wide, amplitude, voltage, burst length, etc. Further, the IMD 16 may be operable to use various electrode configurations to deliver pacing therapy, which may be unipolar, bipolar, quadripoloar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD 16. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The 1 MB 16 may also provide defibrillation therapy and/or cardioversion therapy via electrodes located on at least one of the leads 18, 20, 22. Further, the 1 MB 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 4:
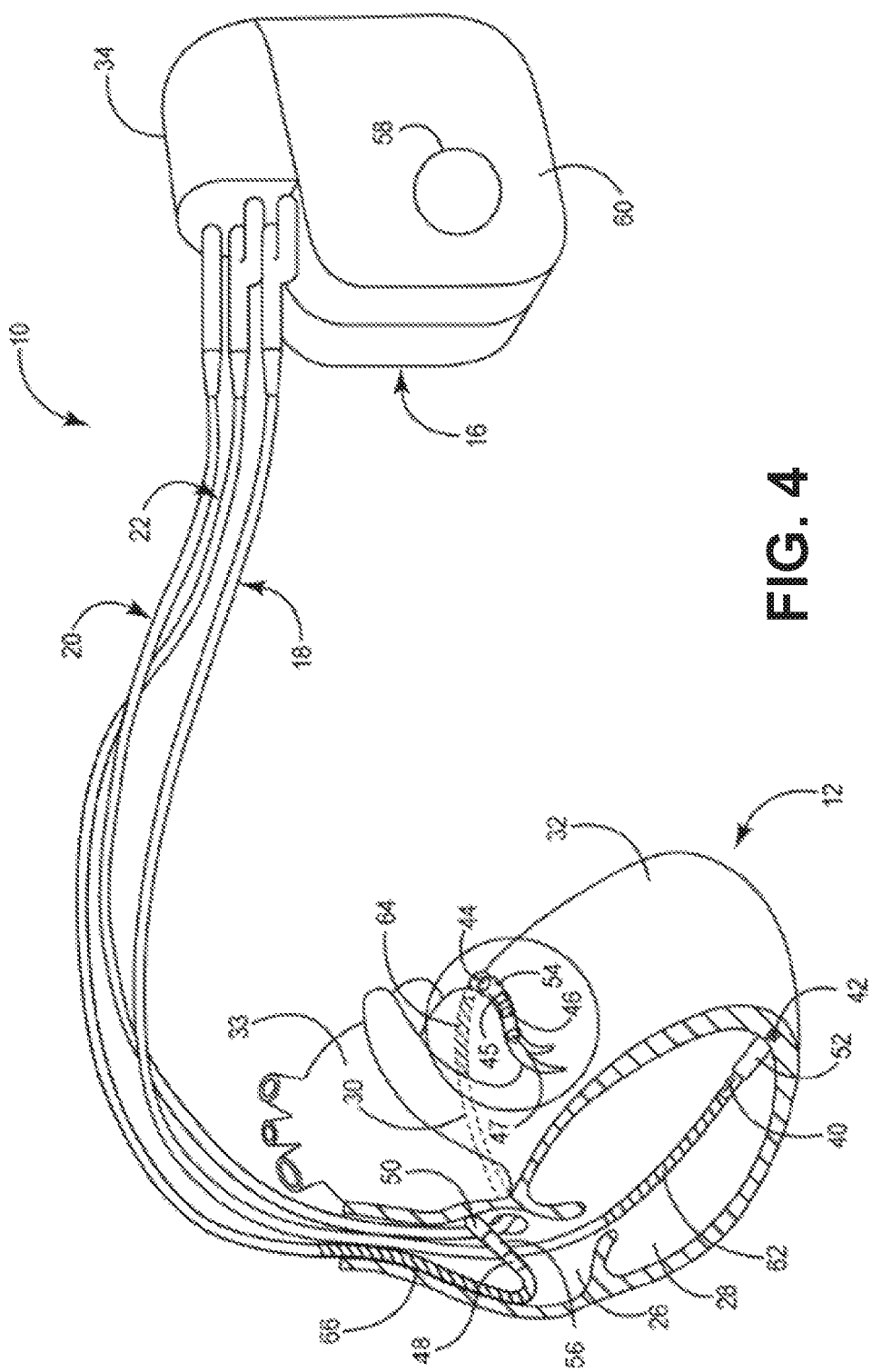
FIG. 4 is a diagram of the exemplary IMD of FIG. 3.
Figure 5:
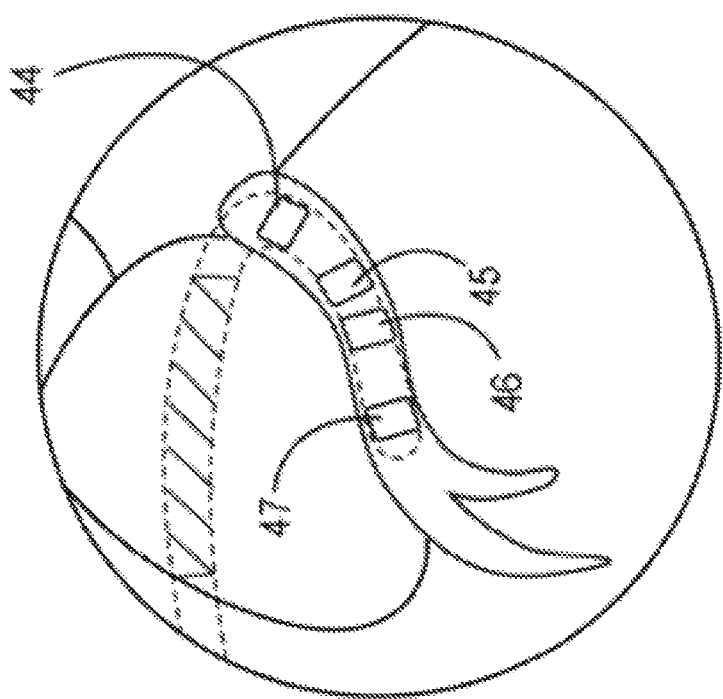
FIG. 5 is a diagram of an enlarged view of a distal end of the electrical lead disposed in the left ventricle of FIG. 4.

FIGS. 4 and 5 are conceptual diagrams illustrating the IMD 16 and the leads 18, 20, 22 of therapy system 10 of FIG. 3 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

Additionally, electrodes 44, 45, 46 and 47 may have an electrode surface area of about 5.3 mm$^2$ to about 5.8 mm$^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 4, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 4, the housing 60 may enclose a therapy delivery module that may include a stimulation generator for generating cardiac pacing pulses and defibrillation or cardioversion shocks, as well as a sensing module for monitoring the electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The configuration of the exemplary therapy system 10 illustrated in FIGS. 3-7 is merely one example. In other examples, the therapy system may include epicardial leads and/or patch electrodes instead of or in addition to the transvenous leads 18, 20, 22 illustrated in FIG. 3. Additionally, in other examples, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 3). Further, in one or more embodiments, the 1 MB 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the 1 MB 16, and each of the leads may extend to any location within or proximate to the heart 12. For example, other examples of therapy systems may include three transvenous leads located as illustrated in FIGS. 3-7. Still further, other therapy systems may include a single lead that extends from the IMD 16 into the right atrium 26 or the right ventricle 28, or two leads that extend into a respective one of the right atrium 26 and the right ventricle 28.

Figure 6:
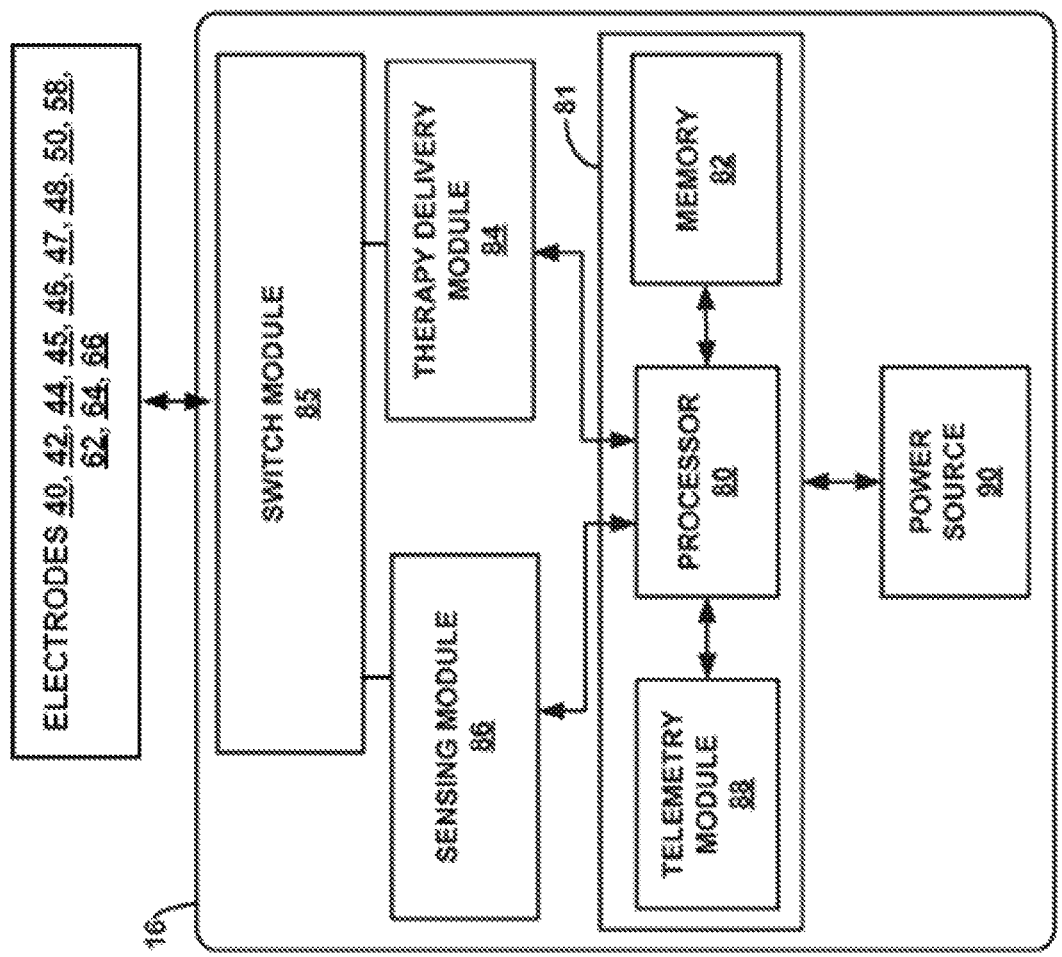
FIG. 6 is a block diagram of an exemplary IMD (e.g., the systems of the FIGS. 3-5)

FIG. 6 is a functional block diagram of one exemplary configuration of the 1 MB 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., AV delays, VV delays, pacing pulses with the amplitudes, pulse widths, frequency, or electrode polarities, etc., which may be specified by one or more selected therapy programs (e.g., AV and/or VV delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of 1 MB 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The 1 MB 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the 1 MB 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 7:
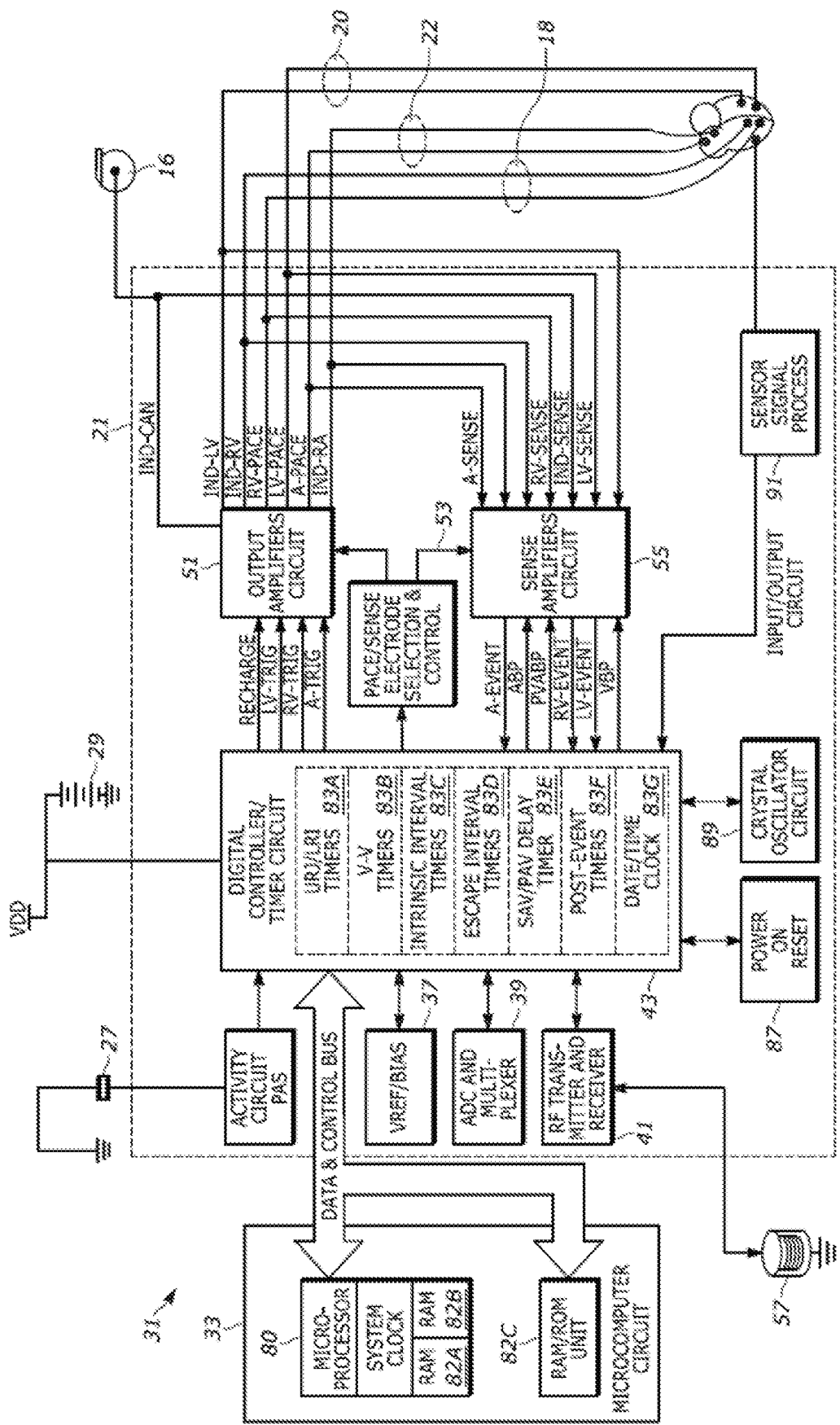
FIG. 7 is another block diagram of an exemplary IMD (e.g., an implantable pulse generator) circuitry and associated leads employed in the systems of FIGS. 3-5.

FIG. 7 is another embodiment of a functional block diagram for 1 MB 16 that depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 43 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in exemplary implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer. The output signal of the patient activity sensor 27 may be processed and used as a RCP. Sensor 27 generates electrical signals in response to sensed physical activity that are processed by activity circuit 35 and provided to digital controller/timer circuit 43. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which is incorporated herein by reference in its entirety. Similarly, the exemplary systems, apparatus, and methods described herein may be practiced in conjunction with alternate types of sensors such as oxygenation sensors, pressure sensors, pH sensors, and respiration sensors, for use in providing rate responsive pacing capabilities. Alternately, QT time may be used as a rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals, V-V delay intervals, and the energy delivered to each ventricle and/or atrium.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 21 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, VV delays, post-ventricular time periods, and post-atrial time periods that vary with the sensor based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 43 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

Figure 8:
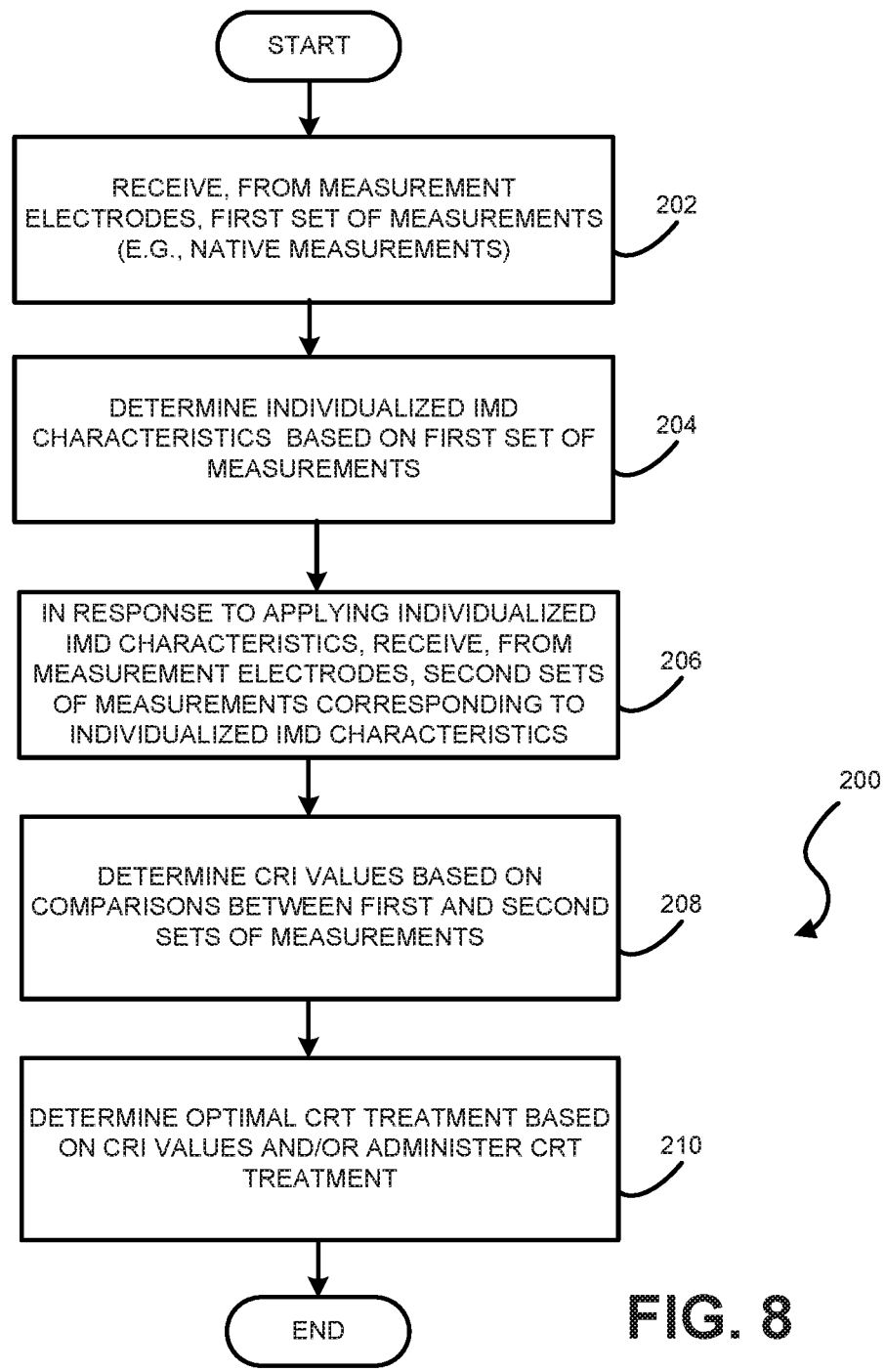
FIG. 8 is a block diagram of an exemplary method for optimizing cardiac resynchronization therapy (CRT) treatments.

FIG. 8 shows an example of a processing sequence 200 for determining IMD parameters and administering cardiac resynchronization therapy using the parameters. FIG. 8 will be described with reference to the system 100 illustrated in FIGS. 1-7. However, any suitable structure, system, component, device, and/or apparatus can be employed.

In operation, at block 202, the computing apparatus 140 may receive, from the measurement electrodes 112 and/or 114, one or more first sets of measurements (e.g., native measurements or first measurements). The native measurements are electrical measurements from the electrodes 112 and/or 114 with the leads 18, 20, and/or 22 of the IMD 16 are turned off. For example, while the leads 18, 20, and/or 22 of the IMD 16 are turned off (e.g., not providing pacing pulses to the heart 12), the measurement electrodes 112 and/or 114 may measure electrical information such as cardiac activation signals (e.g., depolarization and/or repolarization) of the patient's heart 12. The measurement electrodes 112 and/or 114 may provide the electrical information to the interface/amplifier circuitry 116. The interface/amplifier circuitry 116 may amplify the signals and then provide the signals the computing apparatus 140.

In some examples, the computing apparatus 140 may cause display of the electrical measurements, including the native measurements, on the display 132. FIG. 12 shows exemplary measurements from the measurement electrodes 112 and 114 that may be displayed on the display 132. For example, in response to receiving the electrical measurements from the electrodes 112 and/or 114, the computing apparatus 140 may analyze, determine, and/or cause display of the electrical measurements on the display 132. For instance, in response to receiving the native or first measurements, the computing apparatus 140 may determine and/or cause display of the display screen 602 indicating the native measurements. The computing apparatus 140 may receive and/or determine a separate electrical measurement for each of the measurement electrodes 112 and/or 114. Additionally, and/or alternatively, the computing apparatus 140 may determine whether the separate electrical measurement from the electrodes 112 and/or 114 is from an anterior 112 and/or posterior 114 measurement electrode.

As shown in display screen 602, each measurement electrode 112 and/or 114 may be displayed as a separate measurement (e.g., line). Further, the anterior electrodes 112 may be shown graphically distinct from the posterior electrodes 114 (e.g., by using different colors and/or different types of dash lines). In other words, dashed lines 608 may indicate the measurements from the posterior electrodes 114 and lines 610 may indicate the measurements from the anterior electrodes 112.

Returning back to FIG. 8, at block 204, the computing apparatus 140 may determine individualized IMD characteristics based on the first or native measurements and apply the characteristics to the IMD 16. In some examples, the electrical dyssynchrony for patients 14 may be different. As such, the IMD characteristics may be individualized for each patient. Thus, the computing apparatus 140 may determine, from the native measurements, one or more individualized IMD characteristics to apply to the patient 14. The individualized IMD characteristics may include different delays, such as ventricular-ventricular (VV) delays, atrial-ventricular (AV) delay, left-ventricular (LV) delays, bi-ventricular (BiV) delays, and/or other IMD 16 timing delays. Additionally, and/or alternatively, the individualized IMD characteristics may include one or more instructions to turn on or off different IMD 16 leads (e.g., 18, 20, 22) and/or IMD 16 electrodes (e.g., 40, 42, 44, 45, 46, 47, 48, 50). In other words, based on the individualized IMD characteristics, the 1 MB 16 may turn on (e.g., apply pacing pulses to the heart 12) one or more leads/electrodes and/or turn off (e.g., not apply pacing pulses to the heart 12) one or more leads/electrodes.

At block 206, in response to applying the individualized IMD characteristics, the computing apparatus 140 may receive, from the measurement electrodes 112 and/or 114, second sets of measurements (e.g., second measurements) corresponding to the individualized characteristics. For example, at block 204, the computing apparatus 140 may determine multiple different characteristics (e.g., multiple different delays, such as VV delays and/or AV delays). The 1 MB 16 may receive and/or apply the individualized IMD characteristics. In response to applying each individualized IMD characteristics, the computing apparatus 140 may receive a set of second measurements from the measurement electrodes 112 and/or 114 for the corresponding individualized IMD characteristic. For example, if the individualized IMD characteristics includes an AV delay, such as an AV delay of 120 milliseconds (ms), then the computing apparatus 140 may receive second measurements from the electrodes 112 and/or 114 indicating electrical signals of the patient's heart in response to the IMD 16 setting an AV delay of 120 ms.

In some instances, the computing apparatus 140 may determine multiple different individualized 1 MB characteristics. The computing apparatus 140 may receive multiple sets of second measurements from the electrodes 112 and/or 114. Each of the sets of second measurements may correspond to a different individualized IMD characteristics. For example, the individualized IMD characteristics may include an 80 ms, 100 ms, 120 ms, and/or 140 ms AV delay. The 1 MB 16 may apply or set the AV delay to each of the individualized IMD characteristics. In response to setting the AV delay, the computing apparatus 140 may receive a set of second measurements for the corresponding AV delay.

In some variations and referring to FIG. 12, the computing apparatus 140 may cause display of the second measurements on the display 132. For example, the computing apparatus 140 may cause display of display screen 604 on the display 132. The display screen 604 may indicate multiple different individualized IMD characteristic measurements. For example, the left portion of the display screen 604 may indicate first individualized characteristic measurements 606 (e.g., AV delay of 100 ms) and the right portion may indicate second individualized characteristics measurements 607 (e.g., AV delay of 120 ms). The computing apparatus 140 may cause display of separate measurements for each of the measurement electrodes 112 and/or 114 similar to the native measurements. Also, the anterior electrodes 112 may be shown graphically distinct from the posterior electrodes 114 (e.g., by using different colors and/or different types of dash lines).

In some examples, applying the individualized 1 MB characteristics may be automated. For example, the computing apparatus 140 may provide one or more commands and/or instructions to the IMD 16 to apply or set an individualized IMD characteristic. In response to providing the one or more instructions, the computing apparatus 140 may receive measurements from the electrode apparatus 110 (e.g., the measurement electrodes 112 and/or 114) indicating the electrical measurements for the applied individualized IMD characteristic. If there are two or more individualized 1 MB characteristics, the computing apparatus 140 may continuously and/or sequentially provide instructions to apply or set individualized IMD characteristics. Further, the computing apparatus 140 may receive measurements from the electrode apparatus 110 for each of the different individualized IMD characteristics.

In some examples, applying the individualized 1 MB characteristics may be manual. For example, the user may provide user input using the input apparatus 142 for each individualized IMD characteristic. The input apparatus 142 may provide the user input to the processor 150 and/or the IMD 16. Based on the user input, the 1 MB 16 may set or apply the individualized characteristics. Then, the computing apparatus 140 may receive measurements from the electrode apparatus 110 for each of the individualized IMD characteristics.

At block 208, the computing apparatus 140 may determine cardiac resynchronization index (CRI) values based on comparisons between the first (e.g., native measurements) and second measurements (e.g., measurements with corresponding individualized IMD characteristics). For example, the computing apparatus 140 may receive multiple second measurements from the electrode apparatus 110. Each second measurement may have a corresponding individualized 1 MB characteristic. The computing apparatus 140 may determine multiple CRI values by comparing each of the second measurements with the native measurements. For example, the second measurements may correspond to individualized 1 MB characteristics of 60 ms, 80 ms, 100 ms, and 120 ms AV delays. The computing apparatus 140 may compare each of the second measurements with the native measurements to determine CRI values for the 60 ms, 80 ms, 100 ms, and 120 ms AV delays.

Figure 13:
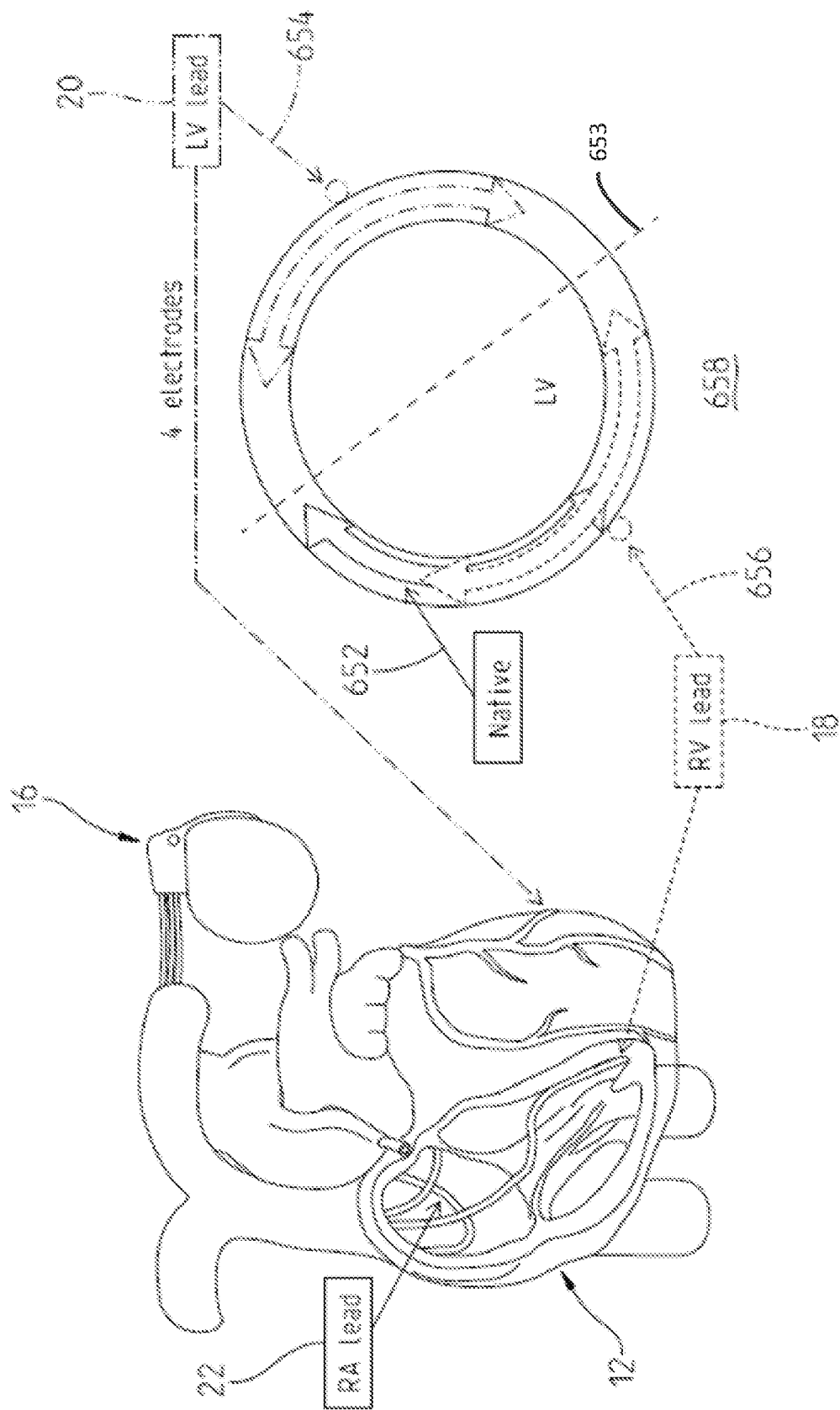
FIG. 13 is an exemplary diagram of a patient's heart, the leads from the IMD, and the wavefronts formed by the leads.

The CRI values may indicate a way to measure the wavefront fusion and cancellation for the leads 18, 20, 22 of the 1 MB 16. FIG. 13 shows a graphical representation of the CRI values and the corresponding leads of the IMD 16. For example, the right atrium (RA) lead 22 may be operatively coupled to the right atrium of the patient's heart 12. Similarly, the right ventricle (RV) lead 18 may be operatively coupled to the right ventricle and the left ventricle (LV) lead 20 may be operatively coupled to the left ventricle. Based on the individualized IMD characteristics, the IMD 16 may apply pacing therapy (e.g., electrical signals) to the leads 18, 20, and/or 22. For instance, the LV lead 20 may provide the LV pulse 654 to the patient's heart 12. Additionally, and/or alternatively, the RV lead 18 may provide the RV pulse 656 to the patient's heart. The pulses 652, 654, 656 may create wavefronts (e.g., RV, LV, and native wavefronts) that propagate throughout the patient's heart 12.

Furthermore, the IMD 16 may operate in an atrial sensing (AS) mode and/or an atrial pacing (AP) mode. For example, in the AS mode, the RA lead 22 (e.g., an atrial sensing lead) may measure the native pulse 652 and/or the timing of the native pulse 652. In other words, the patient 14 provides the native pulse 652 for the heart 12 to depolarize/repolarize and the RA lead 22 may measure the native pulse 652. Additionally, and/or alternatively, in the AP mode, the RA lead 22 (e.g., an atrial pulsing lead) provides the native pulse 652 to the heart 12.

Image 658 shows an exemplary graphical representation of the wavefronts propagating through the left ventricle of the patient's heart 12. For example, the native and RV wavefronts may fuse together and move towards the LV wavefront. Eventually, when the LV wavefront meets the native/RV wavefronts, the wavefronts may cancel each other out. The CRI values indicate the location within the left ventricle of the patient's heart 12 that the wavefronts cancel each other out. For example, a CRI value of 100% may indicate the LV wavefront cancelling the RV/native wavefront at the center of the left ventricle. The center of the left ventricle is shown by line 653. A higher CRI value (e.g., 90%) may indicate a cancellation or a meeting of the wavefronts near the center 653 of the left ventricle (e.g., slightly to the left or right of the center 653). A lower CRI value (e.g., 50%) may indicate a cancellation or a meeting of the wavefronts that is farther away from the center 653 of the left ventricle. In some examples, the computing apparatus 140 may cause display of the image 658 on the display 132.

In some instances, the individualized IMD characteristics may indicate that the RV lead 18 is to be off (e.g., LV only wavefronts). For example, the LV lead 20 may provide the LV pulse 654, but the RV lead 18 might not provide the RV pulse 656. In such instances, the CRI values may indicate a cancellation or a meeting of the LV wavefront with the native wavefront.

At block 210, the computing apparatus 140 may determine the optimal CRI value based on the CRI values and/or provide information to administer cardiac resynchronization therapy (CRT) treatment. For example, based on the determined CRI values (e.g., the CRI values for the 60 ms, 80 ms, 100 ms, and 120 ms AV delays), the computing apparatus 140 may determine the optimal CRI value from the determined CRI values. In some variations, the CRI values are percentages or fractions. The computing apparatus 140 may determine the optimal CRI value as the greatest magnitude percentage or fraction from the determined CRI values.

In response to determining the optimal CRI values, the computing apparatus 140 may provide information to and/or administer the CRT treatment. In some examples, the computing apparatus 140 may provide one or more instructions and/or commands to the IMD 16 to apply or set the IMD 16 to the individualized IMD characteristic for the optimal CRI value. For instance, if the optimal CRI value has an individualized IMD characteristic as 100 ms AV delay, then the computing apparatus 140 may provide instructions to the IMD 16 to set the 1 MB 16 at the 100 ms AV delay.

Figure 14:
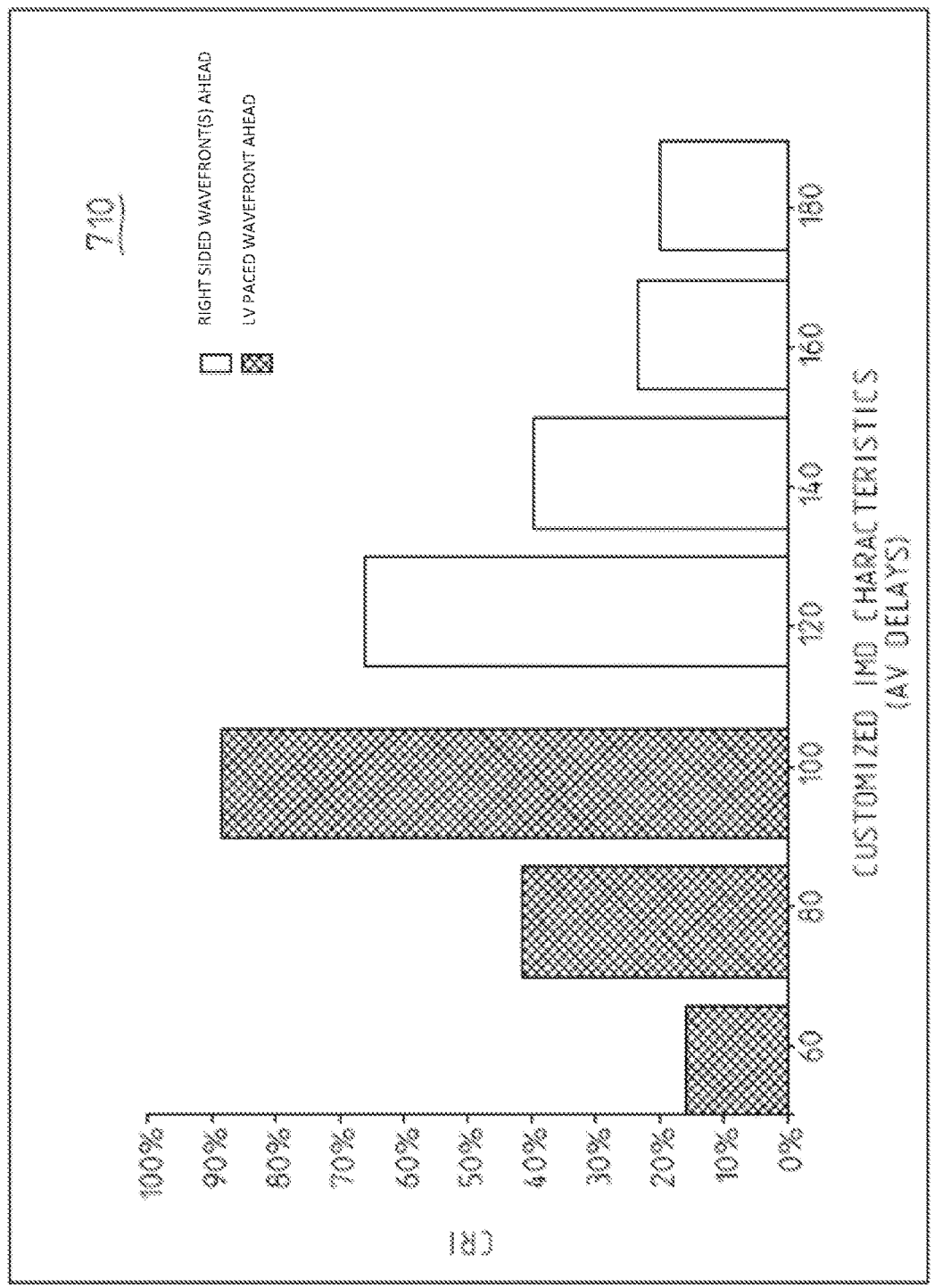
FIG. 14 is another exemplary graphical user interface depicting cardiac resynchronization index (CRI) graphical representations for atrial-ventricular (AV) delays.

In other examples, the computing apparatus 140 may cause display of the CRI values on the display 132. FIG. 14 illustrates an exemplary display 132 showing multiple different CRI values with corresponding individualized 1 MB characteristics (e.g., AV delays). For example, the computing apparatus 140 may cause display of the CRI values for each of the AV delays 60-180 ms. Using the input apparatus 142, the user may provide user input indicating the optimal individualized IMD characteristic (e.g., 100 ms AV delay). The input apparatus 142 may provide information to the processor 150 and/or the IMD 16 to set the IMD 16 at the optimal individualized 1 MB characteristic (e.g., 100 ms AV delay).

Figure 9:
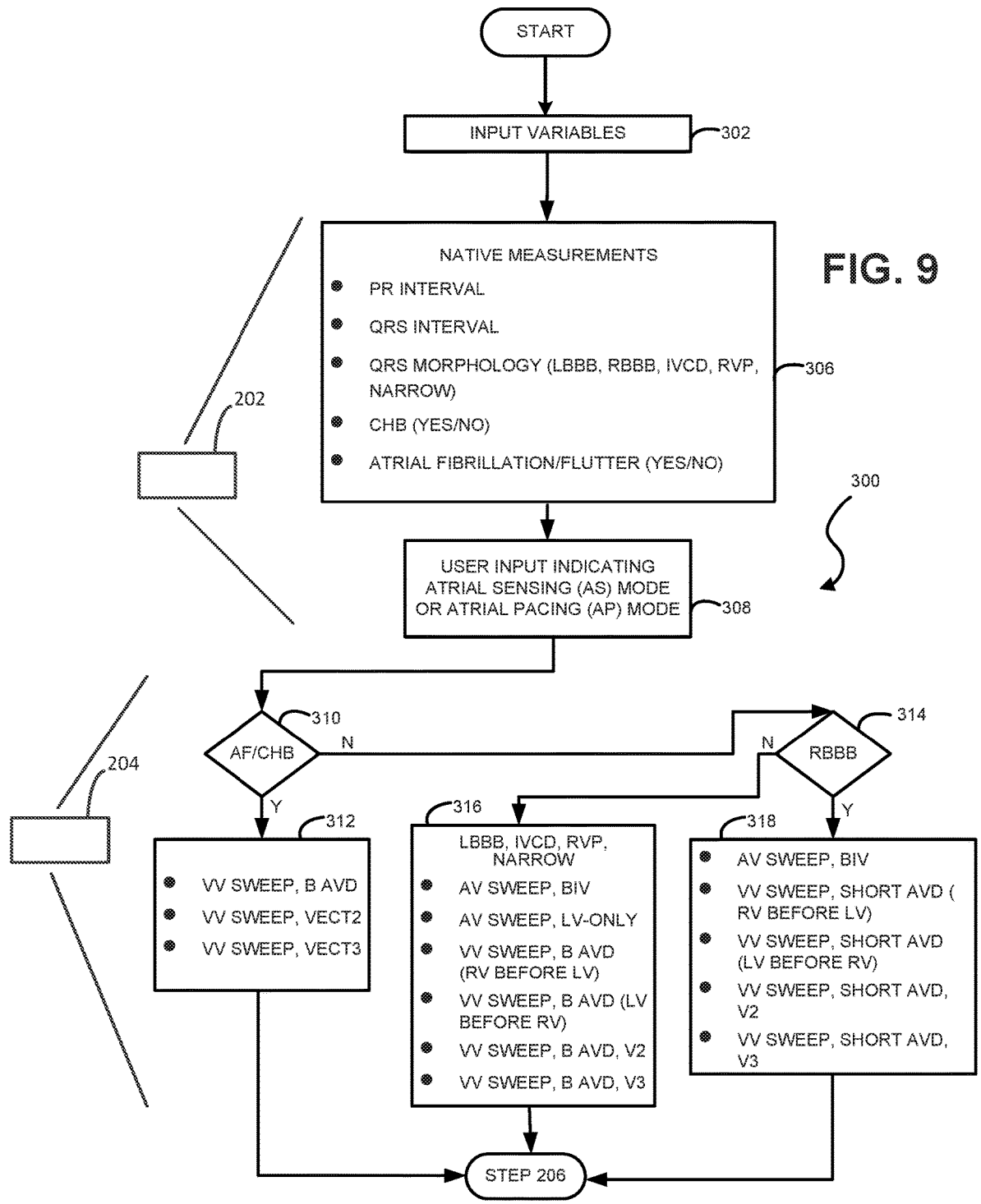
FIG. 9 is another block diagram of an exemplary method for optimizing cardiac resynchronization therapy (CRT) treatments.
Figure 10:
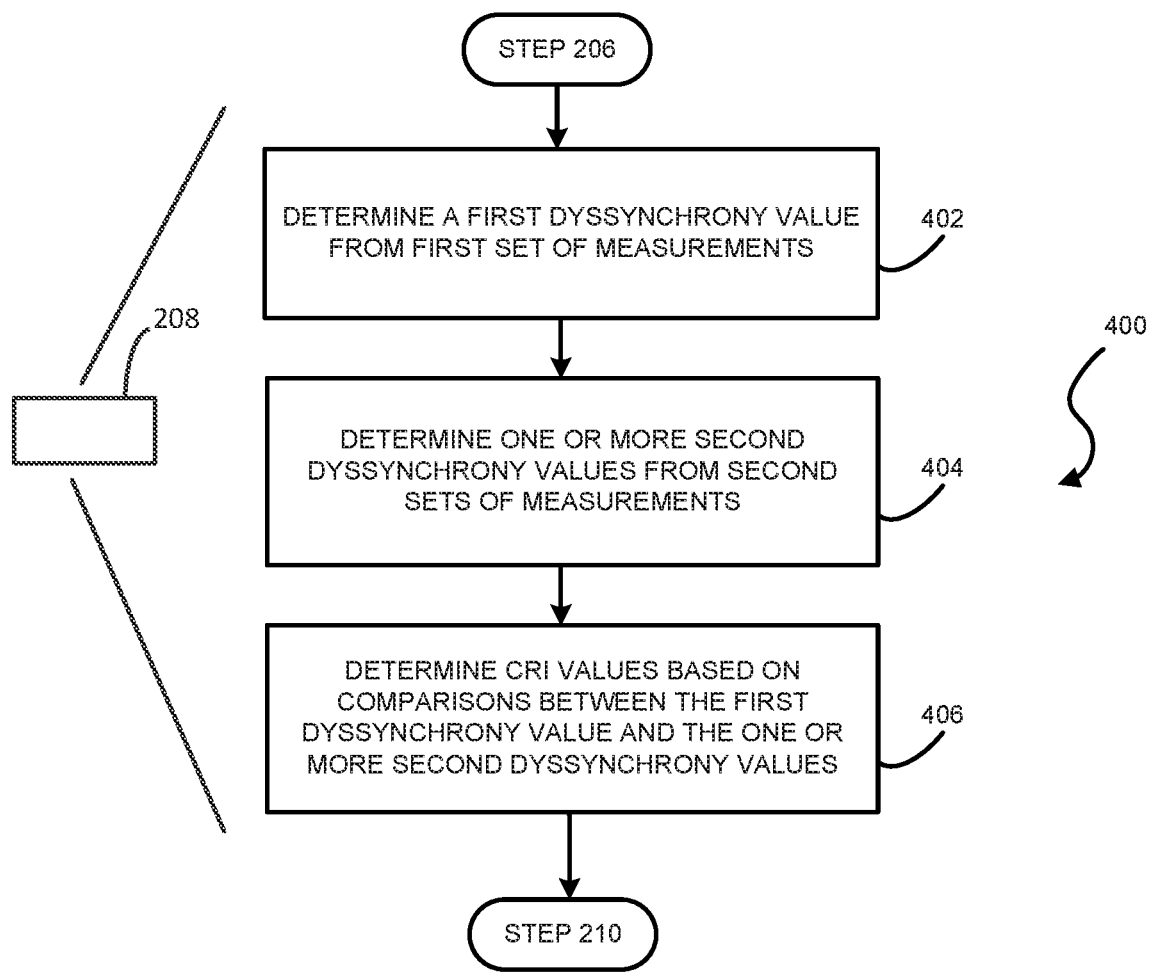
FIG. 10 is another block diagram of an exemplary method for optimizing cardiac resynchronization therapy (CRT) treatments.
Figure 11:
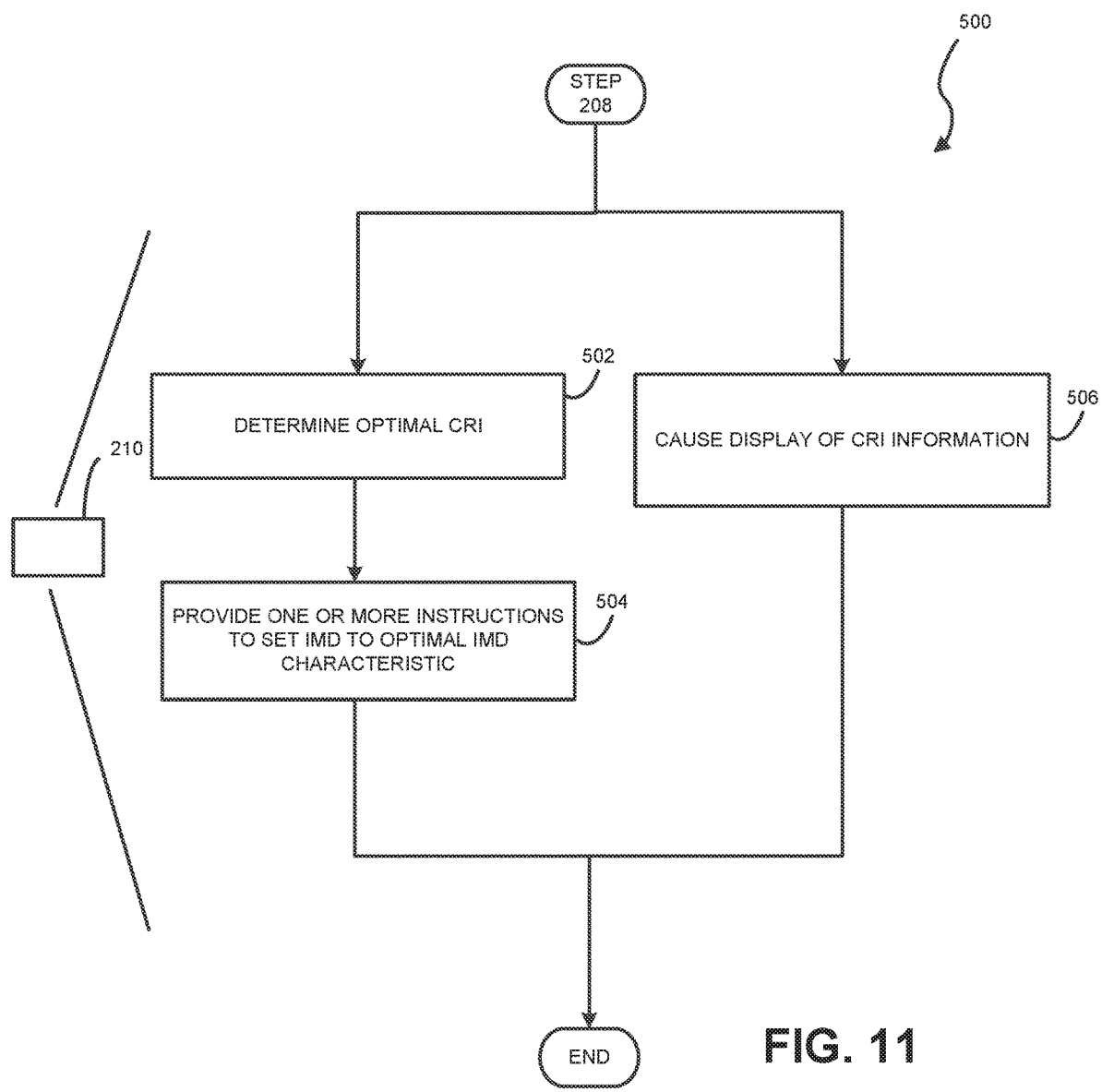
FIG. 11 is another block diagram of an exemplary method for optimizing cardiac resynchronization therapy (CRT) treatments.

FIGS. 9-11 will describe blocks of the processing sequence 200 in more detail. For example, FIG. 9 shows a more detailed version of blocks 202 and 204 from processing sequence 200. In operation, at block 302, the computing apparatus 140 may receive one or more input variables. For example, the computing apparatus 140 may receive, from the input apparatus 142, the name of the patient 14, the date of birth of the patient 14, the date the IMD 16 was implanted in the patient 14, the etiology heart failure (HF) (e.g., the ischemic cardiomyopathy (ICM), non-ischemic cardiomyopathy (NICM), and/or others), and the type of the 1 MB 16 (e.g., manufacturer of the 1 MB 16).

At block 306, the computing apparatus 140 may receive the native measurements from the measurement electrodes 112 and/or 114. As mentioned above, the native measurements may be measurements from the electrodes 112 and/or 114 with one or more leads of the IMD 16 turned off. In some examples, the electrode apparatus 110 may be a 12-lead ECG-CRT device. The computing apparatus 140 may provide one or more instructions or commands to turn off the 1 MB 16. Additionally, and/or alternatively, the user may manually turn off the IMD 16. After turning off the IMD 16, the computing apparatus 140 may receive the native measurements from the measurement electrodes 112 and/or 114 of the 12-lead ECG-CRT device. Based on the native measurements, the computing apparatus 140 may determine the PR interval, the QRS interval, the QRS morphology (e.g., LBBB, RBBB, interventricular conduction delay (IVCD), right ventricular pacing (RVP), Narrow), a complete heart block (CHB) of the patient's heart 12, and/or atrial fibrillation/flutter (AF) of the patient's heart 12.

At block 308, the computing apparatus 140 may determine whether it has received user input indicating atrial sensing (AS) mode or atrial pacing (AP) mode. For example, the computer apparatus 140 may cause display of a prompt (e.g., report) indicating whether the IMD 16 has been operating in an AS mode or an AP mode. Afterwards, the computing apparatus 140 may receive user input indicating to operate in the AS mode or AP mode. The computing apparatus 140 may apply the individualized IMD characteristics to the IMD 16 based on the user input.

In some instances, if the IMD 16 has been operating in a particular mode, such as the AS mode, less than 90% of the time, then the computing apparatus 140 may cause display of a prompt indicating for the user to select a mode to apply the individualized IMD characteristics to the IMD 16 (e.g., the delay types determined at step 204). The computing apparatus 140 may receive user input indicating the mode and use the mode when applying the individualized IMD characteristics. If the IMD 16 is operating in a particular mode, such as mode, more than 90% of the time, the computing apparatus 140 might not cause display of the prompt and may automatically use the particular mode when applying the individualized IMD characteristics.

At block 310, the computing apparatus 140 may determine whether the patient's heart 12 has an AF and/or a CHB. If so, processing sequence 300 may move to block 312. If not, the processing sequence 300 may move to block 314. At block 314, the computing apparatus 140 may determine whether the patient's heart 12 has a RBBB. If so, the processing sequence 300 may move to block 314. If not, the processing sequence 300 may move to block 316. In other words, if the patient's heart 12 has a LBBB, IVCD, RVP, or Narrow, the processing sequence 300 may move to block 316.

In some examples, the determination of blocks 310 and 314 is not sequential, but in parallel. For example, if the computing apparatus 140 determines an AF or CHB, then the processing sequence 300 moves to block 312. If the computing apparatus 140 determines an LBBB, IVCD, RVP, or Narrow, then the processing sequence 300 moves to block 316. If the computing apparatus 140 determines a RBBB, the processing sequence 300 moves to block 318.

At block 312, the computing apparatus 140 determines one or more individualized IMD characteristics such as a first VV delay sweep with an AV delay setting, a second VV delay sweep with a second vector, and/or a third VV delay sweep with a third vector. Additionally, and/or alternatively, the computing apparatus 140 may determine one or more leads (e.g., leads 18, 20, and/or 22) and electrodes (e.g., electrodes 40, 42, 44, 45, 46, 47, 48, 50) from the LV lead 20 to turn on to apply the pacing pulses for the AV and/or VV delays. For example, for the first VV delay sweep with an AV delay setting, the computing apparatus 140 may determine an AV delay characteristic and multiple different VV delay characteristics (e.g., a sweep is multiple different delay characteristics). Additionally, and/or alternatively, the computing apparatus 140 may determine to turn on the LV lead 20 and electrode 44 to apply the pacing pulses.

For the second VV delay sweep with the second vector, the computing apparatus 140 may determine an AV delay characteristic and multiple different VV delay characteristics. Additionally, and/or alternatively, for the second vector, the computing apparatus 140 may determine to turn on the LV lead 20 and a different or second electrode (e.g., electrode 45) from the LV lead 20 to apply the pacing pulses. In some examples, the second VV delay sweep may include the same VV delays and the same AV delay as the first VV delay sweep with the AV delay setting.

In other examples, these may be different. For example, for the first VV delay sweep with an AV delay setting, the computing apparatus 140 may determine an AV delay characteristic and multiple different VV delay characteristics (e.g., a sweep is multiple different delay characteristics). Additionally, and/or alternatively, the computing apparatus 140 may determine to turn on the LV lead 20 and a different or third electrode (e.g., electrode 46) to apply the pacing pulses. In some examples, the third VV delay sweep may include the same VV delays and the same AV delay as the first and second VV delay sweeps. In other examples, these may be different.

Referring to FIG. 13, the AV delay characteristic may indicate a delay characteristic between the native pulse 652 and the RV/LV lead pulses 654/656. For example, in response to detecting and/or providing the native pulse 652, the IMD 16 may delay the RV/LV lead pulses by the AV delay characteristic prior to providing the RV/LV pulses 654/656. The AV delay characteristic may also indicate whether the characteristic is Biventricular (BiV) or LV only. For example, the BiV characteristic indicates that the IMD 16 provides both the RV pulse 656 and the LV pulse 654. The LV only indicates that the IMD 16 provides only the LV pulse 654.

The VV delay characteristic may indicate a VV delay between the RV pulse 656 and the LV pulse 654 (e.g., the RV lead 18 may provide the RV pulse 656 prior to the LV lead 20 providing the LV pulse 654 or the LV lead 20 may provide the LV pulse 654 prior to the RV lead 18 providing the RV pulse 656). In some examples, the type of IMD 16 may indicate which pulse (RV or LV pulse 656, 654) is provided first and which pulse is delayed and provided second. FIG. 21 shows this in more detail. For example, diagram 810 shows a first IMD characteristic that has an AV delay of 130 ms and a VV delay of 0. With just an AV delay of 130 ms, the RV lead 18 and the LV lead 20 both provide an electrical pulse at 130 ms (e.g., the AV delay).

Diagram 820 and 830 show a second IMD characteristic that has an AV delay of 130 ms and a VV delay of –20 ms. However, diagram 820 is for a first type of IMD device 16 and diagram 830 is for a second type of IMD device 16. In diagram 820, the first type of 1 MB device 16 directs the RV lead 18 to provide a pulse at 130 ms (e.g., at the AV delay), but based on the –20 ms VV delay, the 1 MB 16 directs the LV lead 20 to provide a pulse at 110 ms (e.g., 20 seconds prior to the RV delay). In other words, for the first type of 1 MB device 16, the 1 MB 16 provides the electrical pulse for the RV lead at the AV delay and alters the pulse for the LV lead based on the VV delay (e.g., for a positive +20 VV delay, the RV lead pulse would be at 130 ms and the LV lead pulse would be at 150 ms).

In diagram 830, the second type of IMD device 16 directs the LV lead 20 to provide a pulse at 130 ms (e.g., at the AV delay), but based on the –20 ms VV delay, the 1 MB 16 directs the RV lead 18 to provide a pulse at 150 ms. In other words, for the second type of 1 MB device 16, the IMD 16 provides the electrical pulse for the LV or RV lead based on whichever one is ahead (e.g., if VV delay is negative, then LV lead is at the AV delay; if VV delay is positive, then RV lead is at the AV delay), then the other lead is offset by the VV delay.

Returning back to FIG. 9, the 1 MB 16 may delay the RV/LV pulses 654/656 based on the AV delay characteristic and the VV delay characteristics. After applying each of the VV delay characteristics, the processing sequence 300 may move to block 206 and the computing apparatus 140 may receive these second measurements from the measurement electrodes 112 and/or 114.

At block 316, the computing apparatus 140 determines one or more individualized IMD characteristics such as an AV sweep for BiV, an AV sweep for LV-only, a VV sweep for a baseline AV delay with the RV lead 18 providing the pulse 656 prior to the LV lead 20 providing the pulse 654, a VV sweep for a baseline AV delay with the LV lead 20 providing the pulse 654 prior to the RV lead 18 providing the pulse 656, a VV sweep with a baseline AV delay at a second vector, and/or a VV sweep with a baseline AV delay at a third vector. Additionally, and/or alternatively, the computing apparatus 140 may determine one or more leads (e.g., leads 18, 20, and/or 22) and electrodes (e.g., electrodes 40, 42, 44, 45, 46, 47, 48, 50) from the LV lead 20 to turn on to apply the pacing pulses for the AV and/or VV delays. In other words, the 1 MB 16 may delay the RV/LV pulses 654/656 based on the AV and/or VV delay characteristics. Further, the computing apparatus 140 may determine one or more leads and/or electrodes to turn on (e.g., based on the second/third vector). Then, the processing sequence 300 may move to block 206 the computing apparatus 140 may receive these second measurements from the measurement electrodes 112 and/or 114.

At block 318, the computing apparatus 140 determines one or more individualized IMD characteristics such as an AV sweep for BiV, a VV sweep for an AV delay with the RV lead 18 providing the pulse 656 prior to the LV lead 20 providing the pulse 654, a VV sweep for an AV delay with the LV lead 20 providing the pulse 654 prior to the RV lead 18 providing the pulse 656, a VV sweep with a baseline AV delay at a second vector, and/or a VV sweep with a baseline AV delay at a third vector. Additionally, and/or alternatively, the computing apparatus 140 may determine one or more leads (e.g., leads 18, 20, and/or 22) and electrodes (e.g., electrodes 40, 42, 44, 45, 46, 47, 48, 50) from the LV lead 20 to turn on to apply the pacing pulses for the AV and/or VV delays. In other words, the 1 MB 16 may delay the RV/LV pulses 654/656 based on the AV and/or VV delay characteristics. Further, the computing apparatus 140 may determine one or more leads and/or electrodes to turn on (e.g., based on the second/third vector). Then, the processing sequence 300 may move to block 206 the computing apparatus 140 may receive these second measurements from the measurement electrodes 112 and/or 114.

Additionally, and/or alternatively, the determined delay characteristics (e.g., AV/VV) may be based on the PR interval and/or QRS interval. For example, based on the PR interval and/or QRS interval, the computing apparatus 140 may determine different delay timings (e.g., 60 ms, 80 ms, 100 ms, and so on). As such, these delay characteristics may be individualized for the patient 14 based on their own QRS or PR intervals.

Processing sequence 300 shows merely an exemplary processing sequence for determining the individualized IMD characteristics. In other examples, other inputs, parameters, and/or determinations may be used by the computing apparatus 140 to determine the individualized IMD characteristics. Additionally, and/or alternatively, the computing apparatus 140 may determine additional or different delay characteristics and/or types of delay characteristics (e.g., AV, VV, BiV, or LV-only) for the blocks 312, 316, and/or 318.

FIG. 10 shows a more detailed version of block 208 from processing sequence 200. For example, the computing apparatus 140 may use processing sequence 400 to determine the CRI values. At block 402, the computing apparatus 140 may determine a first dyssynchrony value from the first set or native measurements (e.g., from block 202). In some instances, the computing apparatus 140 may use an area under the curve calculation to determine the first dyssynchrony value. For instance, referring to FIG. 12, the computing apparatus 140 may determine the first dyssynchrony value based on the area under of the curve between lines 608 and 610 from the individual measurement electrodes 112 and/or 114.

In some examples, the computing apparatus 140 may determine the area under the curve for a first set of the measurement electrodes (e.g., the anterior electrodes 112 or the posterior electrodes 114) as compared to the other set of measurement electrodes (e.g., the other of the anterior electrodes 112 or the posterior electrodes 114). In other words, the computing apparatus 140 may determine the area under the curve between the sets of the measurement electrodes. For example, the electrode apparatus 110 may include 9 anterior electrodes 112 and 9 posterior electrodes 114. The computing apparatus 140 may calculate the area under the curve between a first anterior electrode measurement and the 9 posterior electrodes measurements. The computing apparatus 140 may determine this for all 9 anterior electrodes 112. The computing apparatus 140 may determine the first dyssynchrony value based on the 81-total area under the curve calculations (e.g., the 9 anterior by 9 posterior electrode measurements). In other words, the computing apparatus 140 may add all 81-total area under the curve calculations to determine the first dyssynchrony value.

In some instances, the electrode apparatus 110 may include more or less than 9 electrodes. As such, the computing apparatus 140 may perform more or less than 81 total area under the curve calculations to determine the first dyssynchrony value. In some variations, the computing apparatus 140 may use one or more matrixes (e.g., a 9×9 matrix for the 9 anterior electrodes 112 and the 9 posterior electrodes 114) to determine the area under the curve calculations and/or the first dyssynchrony value.

At block 404, the computing apparatus 140 may determine one or more second dyssynchrony values from one or more second sets of measurements (e.g., from block 206). Each of the second dyssynchrony values may correspond to a different individualized IMD characteristic. In some instances, the computing apparatus 140 may use an area under the curve calculation to determine the second dyssynchrony value. For instance, similar to block 402, the computing apparatus 140 may determine the area under the curve for a first set of the measurement electrodes (e.g., the anterior electrodes 112 or the posterior electrodes 114) as compared to the other set of measurement electrodes (e.g., the other of the anterior electrodes 112 or the posterior electrodes 114). The computing apparatus 140 may use the area under the curve calculations to determine the second dyssynchrony value. The computing apparatus 140 may repeat block 404 multiple times to determine the second measurements for each of the individualized IMD characteristics. In some variations, the computing apparatus 140 may use one or more matrixes (e.g., a 9×9 matrix for the 9 anterior electrodes 112 and the 9 posterior electrodes 114) to determine the area under the curve calculations and/or the second dyssynchrony values.

In some examples, instead of using area under the curve, the computing apparatus 140 may use a different method, process, or algorithm to determine the first and/or second dyssynchrony values. Exemplary methods, processes, or algorithms to determine the first and/or second dyssynchrony values, including the area under the curve metric and other metrics such as inter-activation event distance metric, composite height metric based on maximum heights of the measurement electrodes 112 and 114, and/or ventricular electrical uncoupling (VEU) metric, may be described in U.S. Patent Application No. 62/609,935 filed on Dec. 22, 2017 and entitled "ANTERIOR AND POSTERIOR ELECTRODE SIGNALS," which is incorporated herein by reference in its entirety.

At block 406, the computing apparatus 140 may determine the CRI values based on comparisons between the first dyssynchrony value and the one or more second dyssynchrony values. For example, the computing apparatus 140 may compare the first and second dyssynchrony values to determine the CRI values (e.g., the location within the left ventricle of the patient's heart 12 that the wavefronts (the LV wavefront and the RV/native wavefronts) cancel each other out).

For instance, the computing apparatus 140 may use area under the curve to calculate the amount of electrical dyssynchrony within the heart 12 (e.g., the more extreme the electrical dyssynchrony, the greater magnitude the value of the area under the curve). In patients with electrical dyssynchrony, the heart 12 may beat out of synch, which may cause a greater area under the curve value between the measurements from the anterior electrodes 112 and the measurements from the posterior electrodes 114. In patients without electrical dyssynchrony, the heart 12 may beat in synch, which may cause a smaller (including substantially zero) area under the curve value between the measurements from the anterior electrodes 112 and the measurements from the posterior electrodes 114. The computing apparatus 140 may use the following calculation to determine the CRI values for the one or more second dyssynchrony values for the individualized IMD characteristics:

$$\text{CRI Value (Percentage)} = \text{Abs}[(\text{First Dyssynchrony Value} - \text{Second Dyssynchrony Value})/\text{First Dyssynchrony Value} * 100]$$

where the first and second dyssynchrony values are described above and Abs is an absolute value of the calculation.

In some examples, the computing apparatus 140 may determine the optimal individualized IMD characteristic for the CRT treatment as the characteristic with the greatest magnitude CRI value or percentage (e.g., the value closest to 1 or 100%). For example, as the second dyssynchrony value increases, the CRI value may decrease. However, as the second dyssynchrony value decreases, the CRI value may increase. The optimal IMD characteristic may be the characteristic with the greatest magnitude CRI value.

Additionally, and/or alternatively, the first dyssynchrony value (e.g., the value corresponding to the native measurements) may cause the IMD characteristic to be more individualized for the patient 14. For example, the native measurements indicate the patient's heart 12 without leads 18, 20, 22 providing electrical pulses (e.g., the native or natural measurements of the heart). Each patient may have a different native measurement with a different dyssynchrony value. In other words, each patient may be unique, and some patients may have greater electrical dyssynchrony while others may have less electrical dyssynchrony. As such, by using the equation above, the computing apparatus 140 takes into account the native measurements (e.g., the natural heartbeat) for the particular patient when determining the effectiveness of the individualized IMD characteristics.

Additionally, and/or alternatively, by using the CRI values to determine the optimized IMD characteristic for the IMD 16, less measurement electrodes 112 and/or 114 may be used. For example, traditional methods may need to use substantially more measurement electrodes due to outlier measurements and other faults. However, by using area under the curve to determine the CRI values, less measurement electrodes, including 18 noninvasive measurement electrodes, may be used to determine the optimized 1 MB characteristic.

FIG. 11 shows a more detailed version of block 210 from processing sequence 200. For example, the computing apparatus 140 may use processing sequence 500 to administer the CRT treatment. At block 502, the computing apparatus 140 may determine the optimal CRI value. As mentioned previously, the optimal CRI value may be the greatest magnitude CRI value or percentage (e.g., the value closest to 1 or 100%). At block 504, the computing apparatus 140 may provide one or more instructions to set the IMD 16 to the optimal IMD characteristic corresponding to the optimal CRI value. For example, if the computing apparatus 140 determines the individualized IMD characteristic of 120 ms AV delay has the greatest magnitude CRI value, then the computing apparatus 140 may provide one or more instructions to set the IMD 16 to 120 ms AV delay.

Additionally, and/or alternatively, at block 506, the computing apparatus 140 may cause display of the CRI information, including one or more of the CRI values, as images and/or visual indicia. In some examples, as mentioned previously, the user may manually input the optimized CRI value based on the displayed CRI information on the display 132. Based on the user input, the computing apparatus 140 may set the IMD 16 to the optimized CRI value. In other examples, block 506 may be in series with blocks 502 and 504. In other words, the computing apparatus 140 may determine the optimized CRI value, provide one or more instructions to set the 1 MB 16 at the optimized IMD characteristic based on the optimized CRI value, and cause display of the CRI information on the display 132.

FIGS. 14-20 show different images and/or visual indicia that the computing apparatus 140 may cause display of on the display 132. The images from FIGS. 14-19 are exemplary and additional images indicating the CRI information may be displayed on the display 132. Referring to FIG. 14, the computing apparatus 140 may cause display of image 710 on the display 132. Image 710 shows different AV delays (e.g., LV-only AV delays) with their corresponding CRI values. Furthermore, image 710 may also show whether the AV delays cause a dominant LV lead wavefront or a dominant RV/native lead wavefront. For example, the hatched shading may indicate a dominant LV lead wavefront (e.g., the LV wavefront and the RV/native wavefront meet on the right side from the center 653 of the left ventricle). The white color may indicate a dominant RV/native lead wavefront (e.g., the LV wavefront and the RV/native wavefront meet on the left side from the center 653 of the left ventricle).

Figure 15:
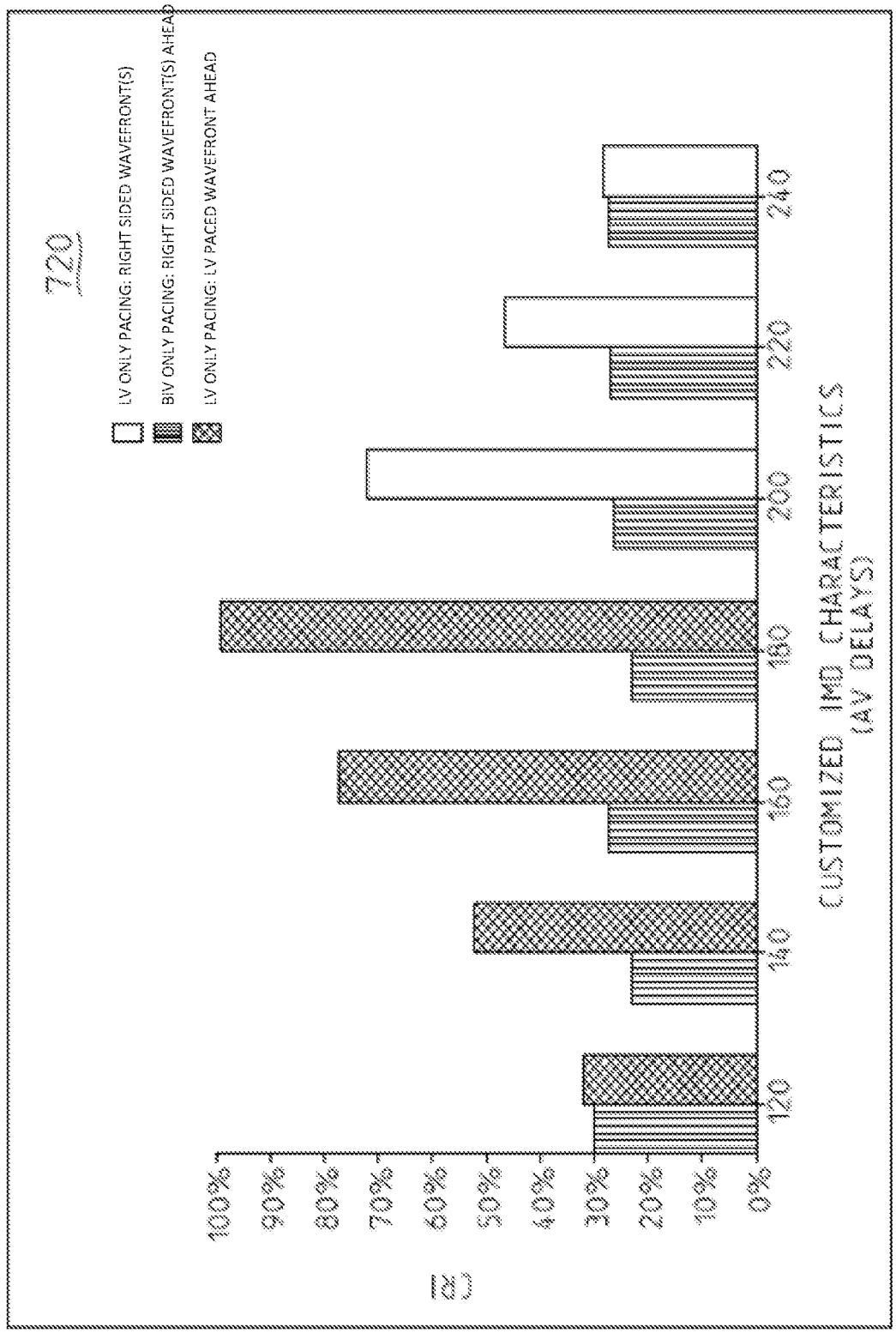
FIG. 15 is another exemplary graphical user interface depicting CRI graphical representations for atrial-ventricular (AV) delay, including Bi-Ventricular (BiV) delays and Left Ventricle (LV) only delays.

Referring to FIG. 15, the computing apparatus 140 may cause display of image 720 on the display 132. Image 720 shows different AV delays with their corresponding CRI values. Additionally, image 720 shows the LV-only AV delays and the BiV AV delays. Furthermore, image 720 may also show whether the AV delays cause a dominant LV lead wavefront or a dominant RV/native lead wavefront.

Figure 16:
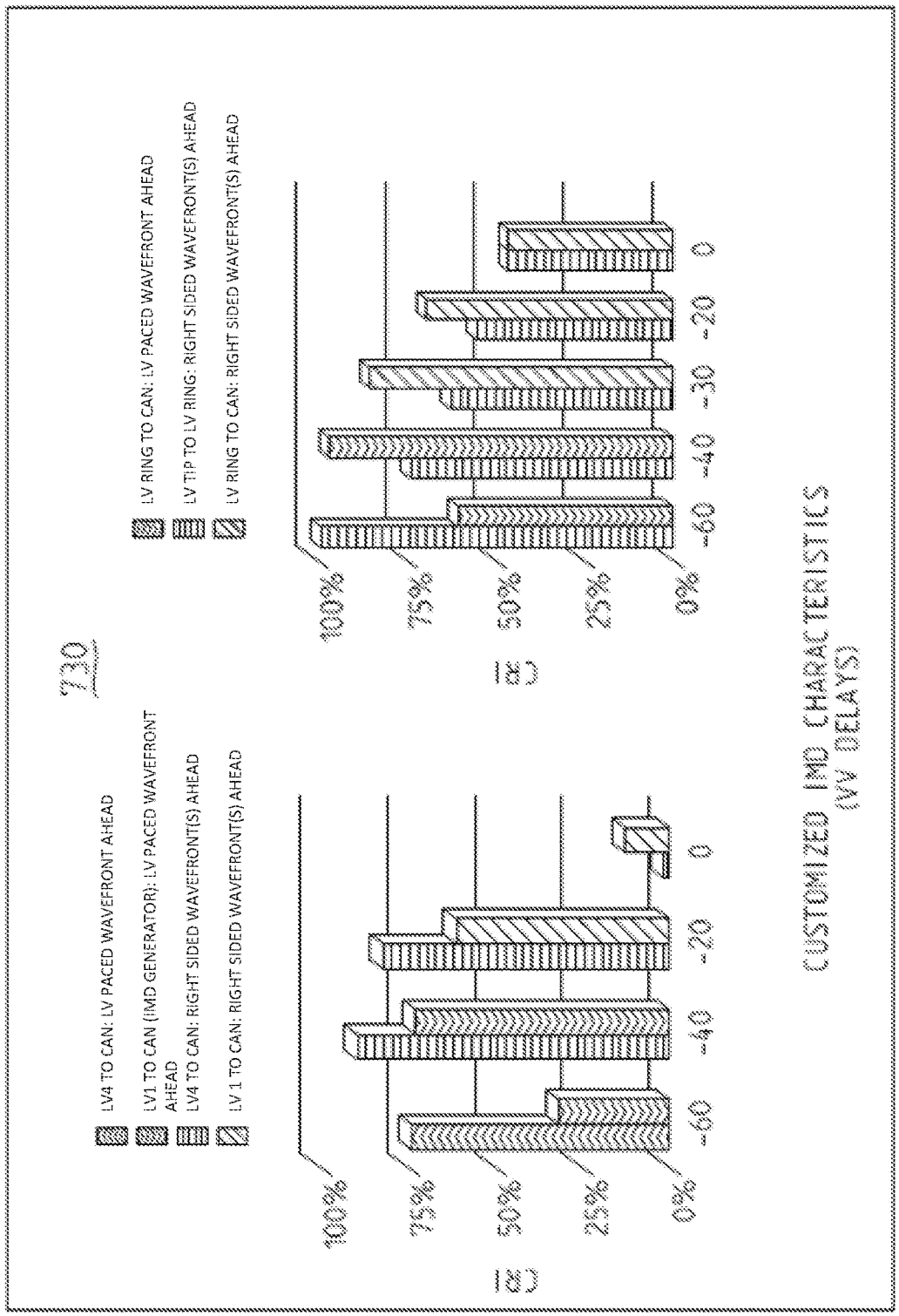
FIG. 16 is another exemplary graphical user interface depicting CRI graphical representations for ventricular-ventricular (VV) delays.

Referring to FIG. 16, the computing apparatus 140 may cause display of image 730 on the display 132. Image 730 shows different VV delays with their corresponding CRI values. Furthermore, image 710 may also show whether the VV delays cause a dominant LV lead wavefront or a dominant RV/native lead wavefront. Additionally, image 730 shows the CRI values for the different electrodes 44, 45, 46, 47 of the LV lead 20 being turned on or off (e.g., the LV 4 to CAN indicates measurements with the LV 4 electrode from the LV lead 20 being turned on as a cathode and the 1 MB 16 being the anode; the LV 1 to CAN indicates measurements with the LV 1 electrode from the LV lead 20 being turned on as a cathode and the 1 MB 16 being the anode; the LV tip to LV ring indicates measurements with the a first electrode from the LV lead 20 being turned on as a cathode and a second electrode from the LV lead 20 as the anode; the LV ring to CAN indicates measurements with a first electrode from the LV lead 20 being turned on as a cathode and the IMD 16 being the anode).

Figure 17:
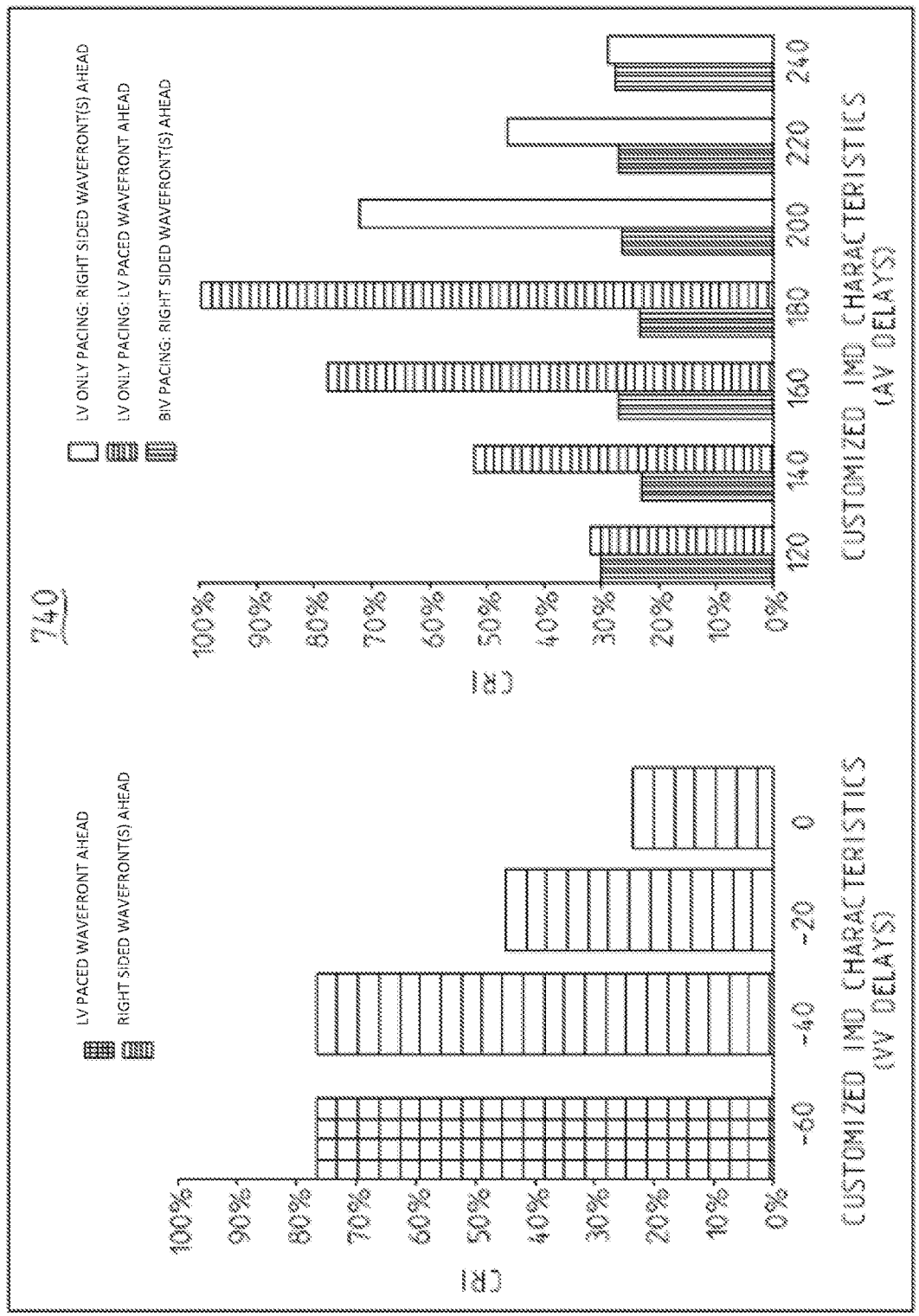
FIG. 17 is another exemplary graphical user interface depicting CRI graphical representations for AV delays and VV delays.

Referring to FIG. 17, the computing apparatus 140 may cause display of image 740 on the display 132. Image 740 shows different AV delays with their corresponding CRI values and different VV delays with their corresponding CRI values. Furthermore, image 740 may show whether the AV delays cause a dominant LV lead wavefront or a dominant RV/native lead wavefront.

Figure 18:
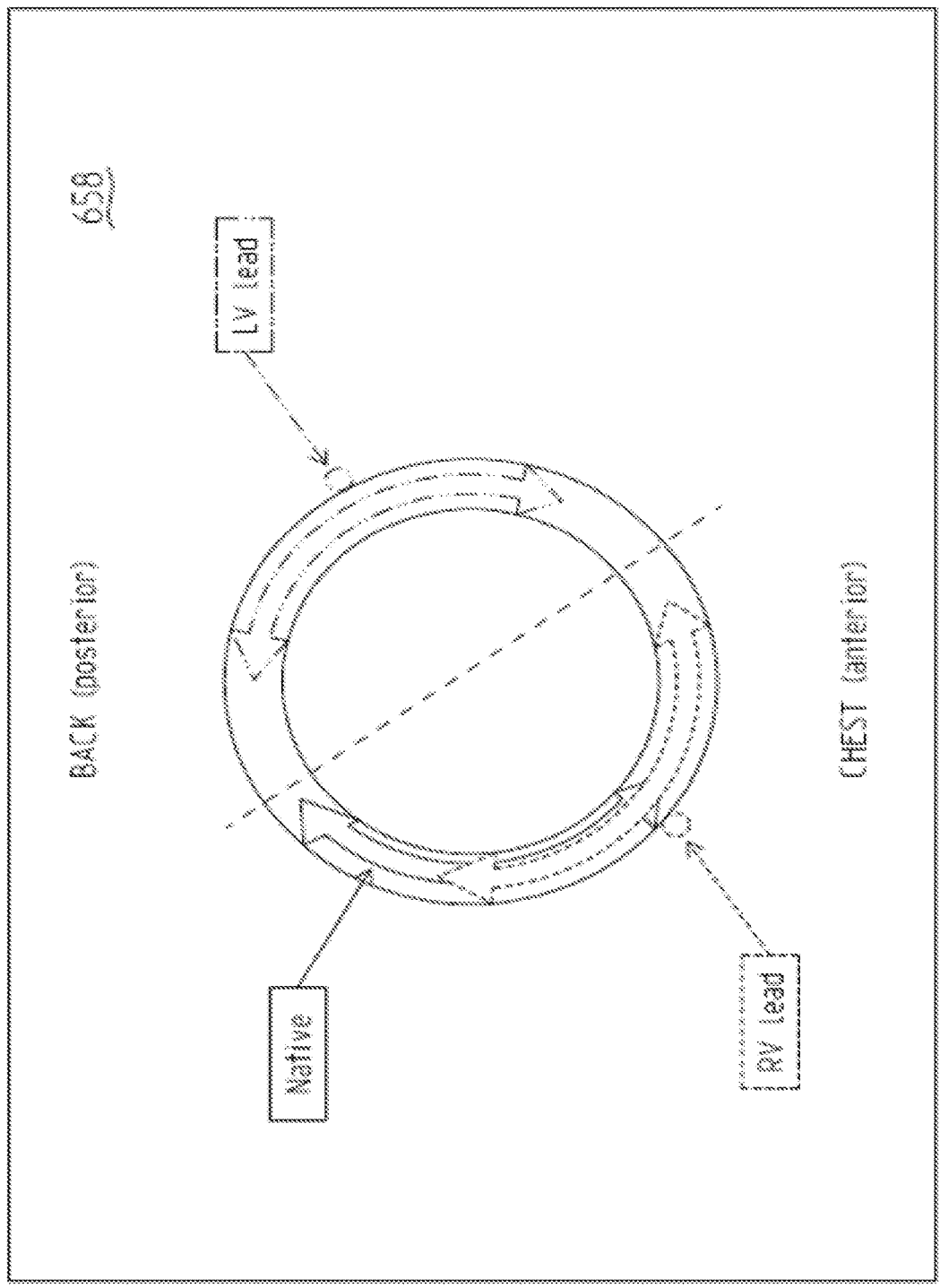
FIG. 18 is another exemplary graphical user interface depicting wavefronts from the leads of the IMD propagating through a patient's heart.

Referring to FIG. 18, the computing apparatus 140 may cause display of the image 658 from FIG. 13 on the display 132. As mentioned above, image 658 shows an exemplary graphical representation of the wavefronts from the leads 18, 20, and 22 propagating through the left ventricle of the patient's heart 12. In some instances, image 658 may be an animation. For instance, the display 132 may show the wavefronts propagating from the leads 18, 20, and/or 22 and through the left ventricle until the cancellation between the LV wavefront and the RV/native wavefronts.

In some examples, the user may use the input apparatus 142 to select an individualized IMD characteristic from the images 710-740. Based on the user selection, the computing apparatus 140 may cause display of the image 658 or the animation for the image 658 corresponding to the selected individualized IMD characteristic on the display 132.

Figure 19:
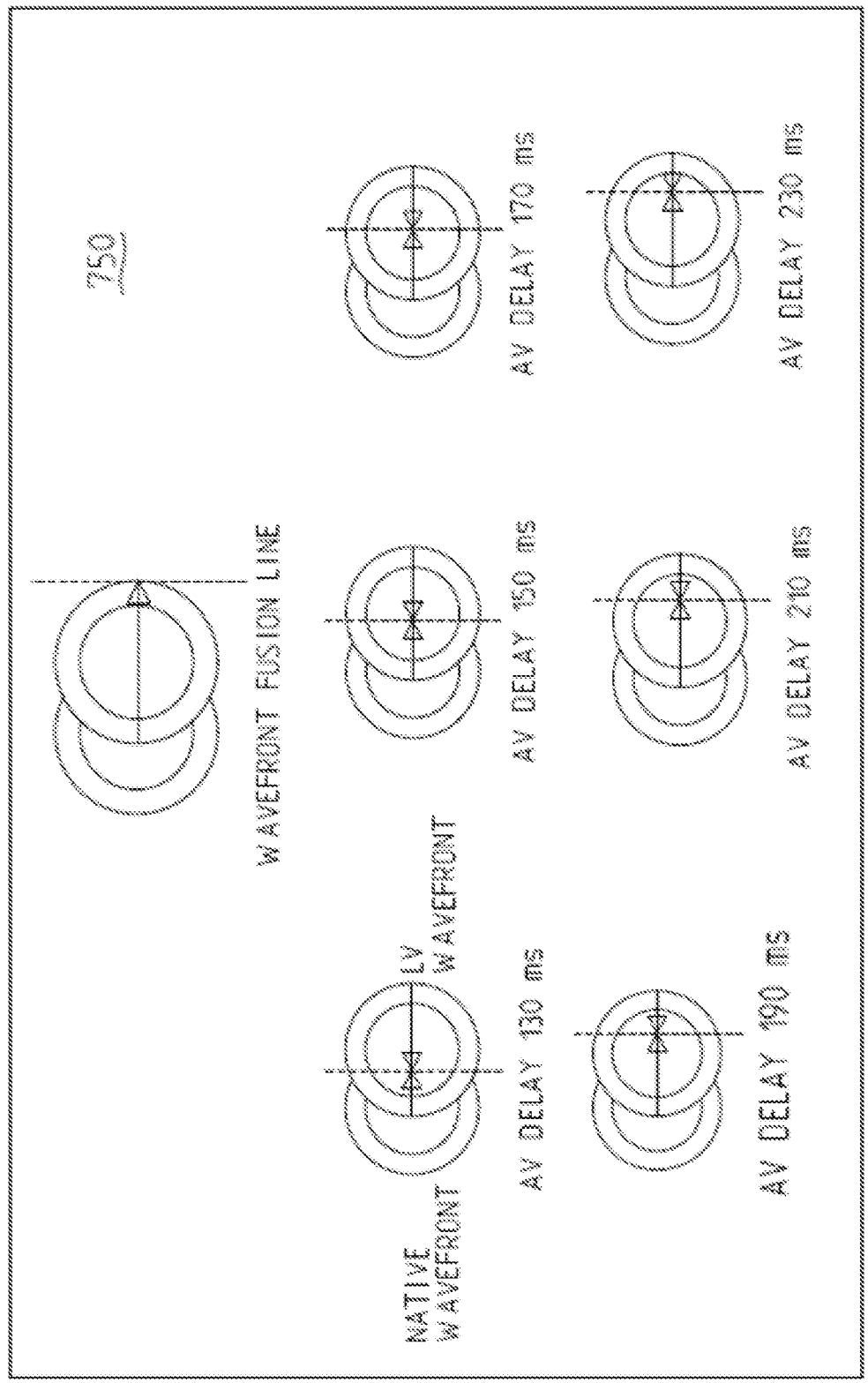
FIG. 19 is another exemplary graphical user interface depicting wavefronts from the leads of the IMD propagating through a patient's heart for different AV delays.

Referring to FIG. 19, the computing apparatus 140 may cause display of the image 750 on the display 132. Image 750 may be similar to image 658 and show exemplary graphical representations of the wavefronts from the leads 18, 20, and 22 propagating through the left ventricle of the patient's heart 12 for multiple different IMD characteristics. In some instances, image 750 may be an animation. For instance, the display 132 may show the wavefronts propagating from the leads 18, 20, and/or 22 and through the left ventricle until the cancellation between the LV wavefront and the native wavefronts for different IMD characteristics (e.g., AV delays).

In some examples, the computing apparatus 140 may determine the timing for each of the wavefronts (e.g., when each of the wavefronts may begin propagating through the left ventricle). For example, the computing apparatus 140 may determine the delay timing between the RA lead 22 (e.g., the right atrium sensing or right atrium pulse lead and/or electrode) and the RV lead 18 may be the PR interval determined from the native measurements. The LV lead 20 pulse (e.g., the native ahead of the LV pulse) may be determined by the PR interval minus the AV delay at the LV-only CRI optimized value, which is described above. The RV lead 18 pulse for being ahead of the LV lead 20 pulse may be determined by 100%−(CRI at BiV short AVD/2).

In other words, if the PR interval for a patient is 260 ms, the AV delay at LV-only CRI optimal is 180 ms, and the CRI at BIV short AV delay is at 30%, then the native is 80 ms (260 ms−180 ms) ahead of the LV pulse, the RV pulse is 35 ms ahead of the LV pulse and the native is 45 ms ahead of the RV pulse. In response to determining these timing, the computing apparatus 140 may cause display of an animation showing the wavefronts for the pulses propagating through the patient's left ventricle and meeting (e.g., cancelling) at a particular location.

Figure 20:
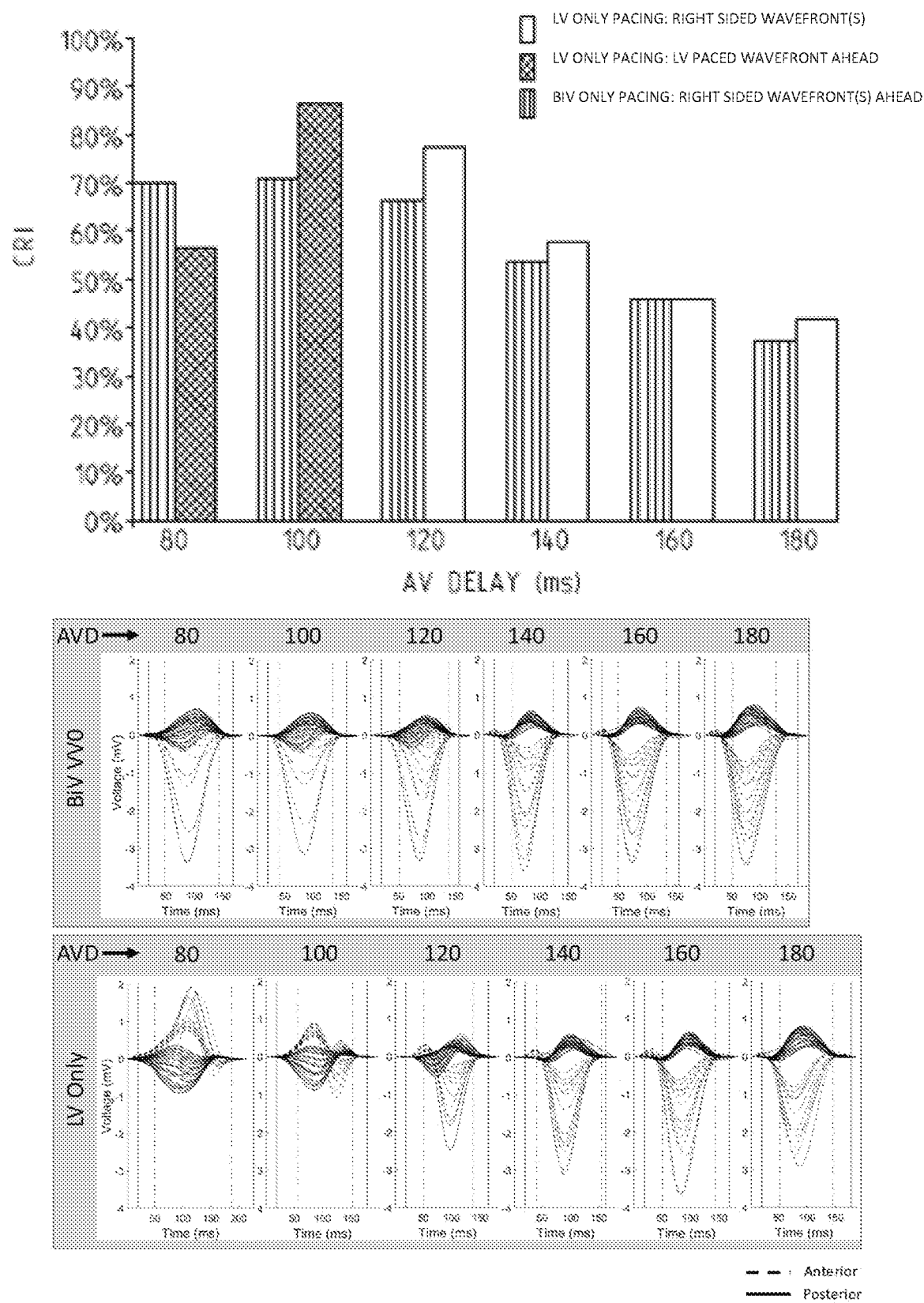
FIG. 20 is another exemplary graphical user interface depicting measurements from the measurement electrodes and the CRI values for AV delays.

Referring to FIG. 20, the computing apparatus 140 may cause display of the image 760 on the display 132. Image 760 shows different AV delays (e.g., LV-only and BiV delays) with their corresponding CRI values. Furthermore, image 760 shows the measurement electrode 112 and/or 114 measurements used to determine the CRI values for the different AV delays.

A study was performed using the above methods, and processes (e.g., the processing sequences 200-500). During the study, patients underwent routine device interrogation to assess lead thresholds and the atrial-RV sense time (A-RVs). Standard 12-lead ECGs measurements were performed with CRT off (e.g., leads from 1 MB 16 off) to confirm the presence of LBBB and to measure QRS and PR intervals. In patients with underlying complete heart block (CHB), RV pacing (e.g., using the RV lead 18) was used in place of native condition. Data was acquired with biventricular (BiV) and LV-only pacing over a wide range of AVDs (typically 40-90% of intrinsic PR interval in 20 ms steps) and VV delays (typically VV=0 to LV pre-activation of 60 ms in 20 ms steps). All data was acquired at the pacing vector and electrode chosen by the implanting electrophysiologist and VV delays were assessed at the presenting AV delay (usually about 70% of intrinsic PR interval).

Figure 22:
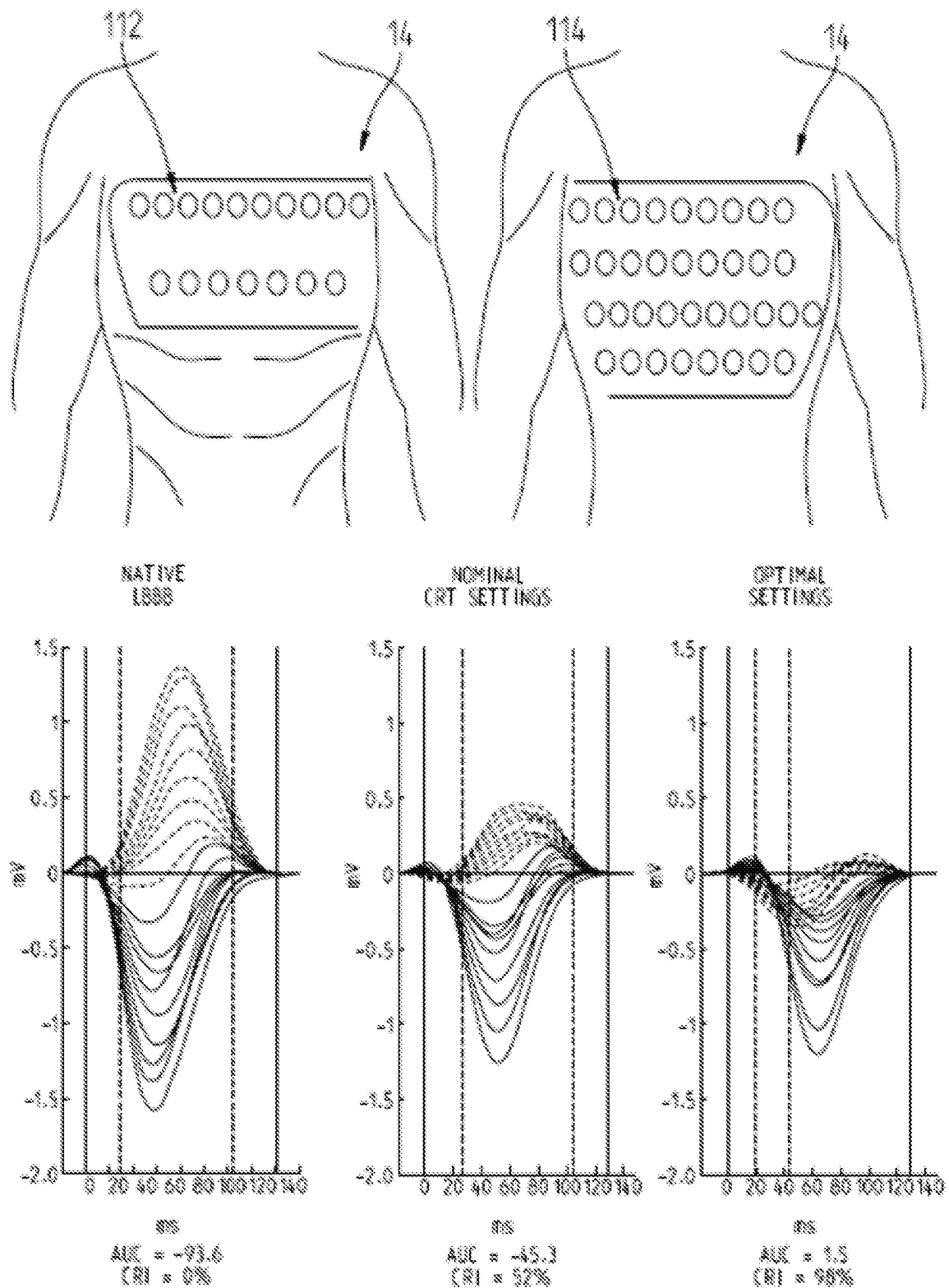
FIG. 22 is another exemplary graphical user interface depicting of another exemplary electrode configuration for the electrode apparatus and the corresponding measurements from the electrode apparatus.
Figure 23A:
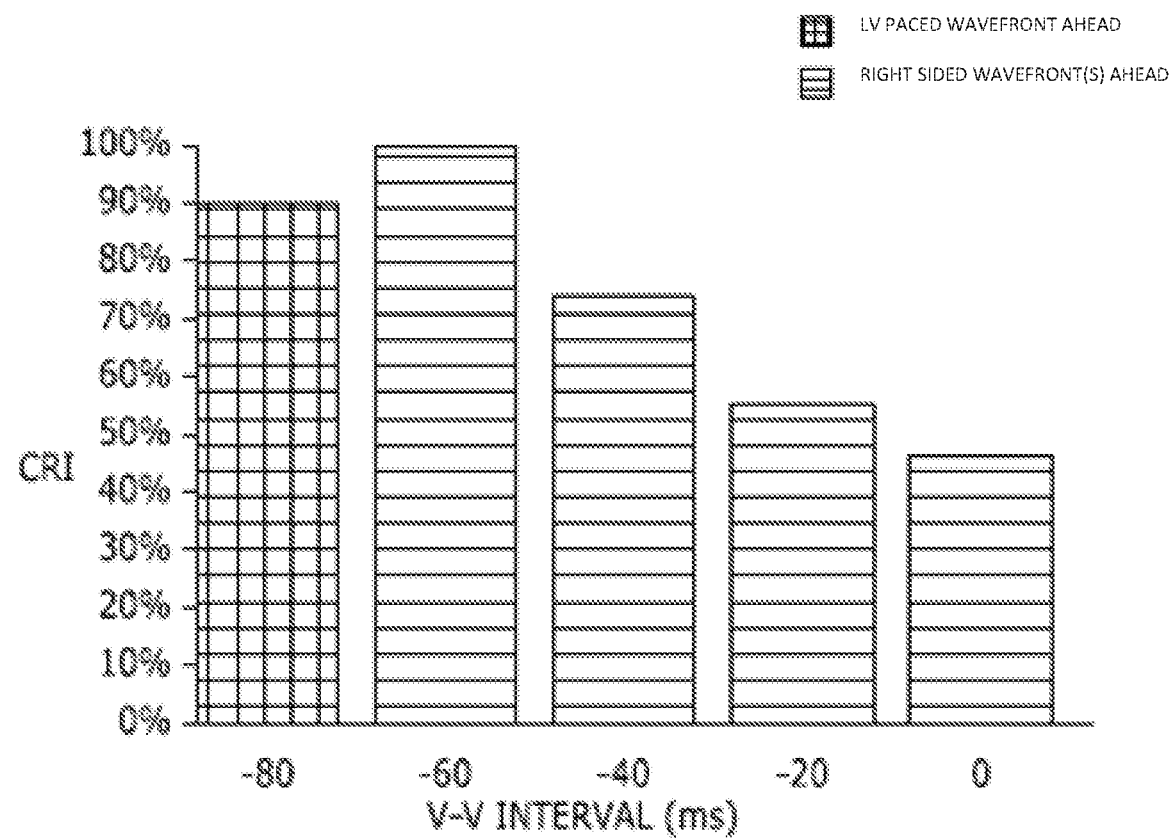
Figure 23B:
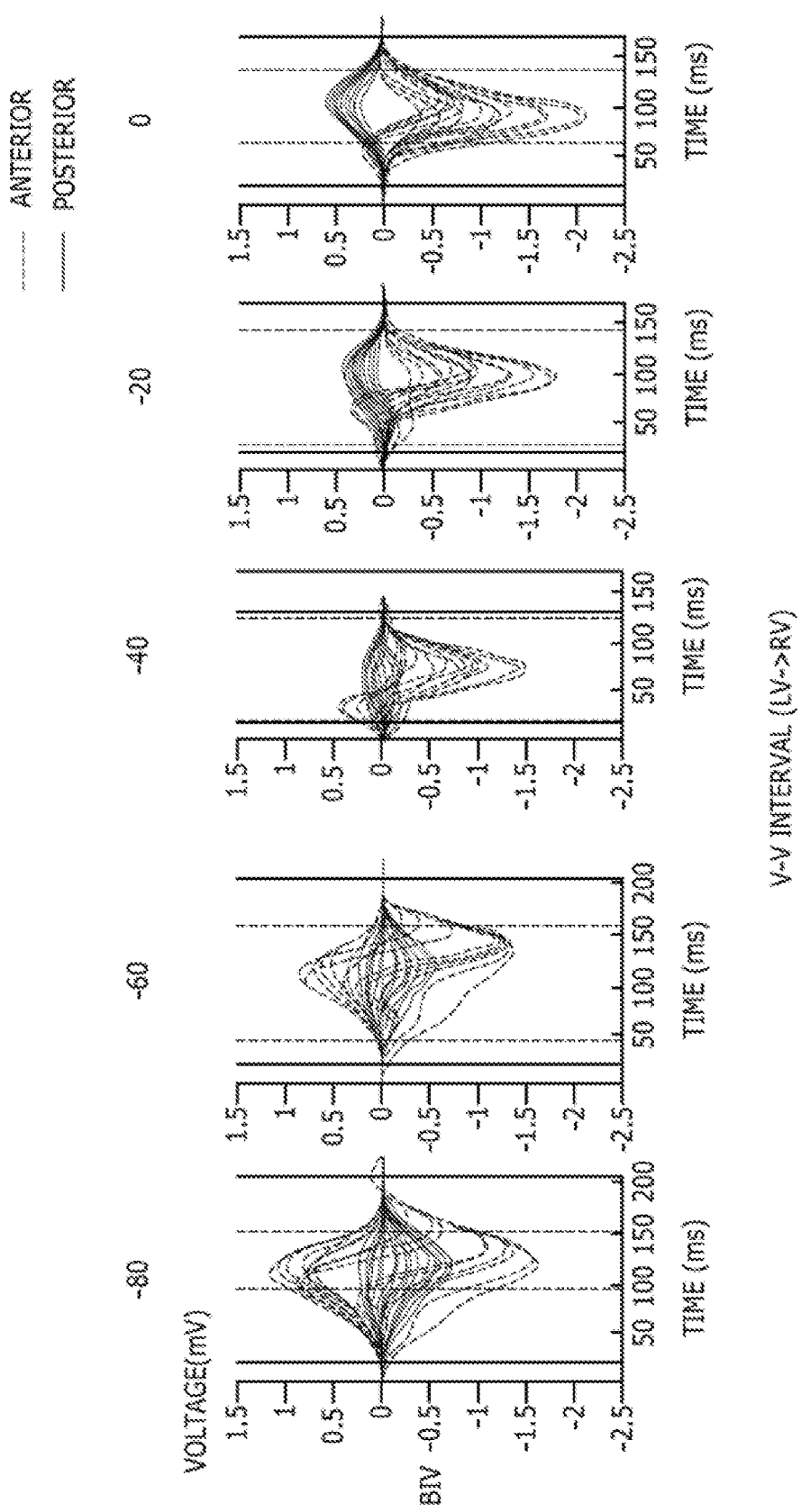
Figure 23C:
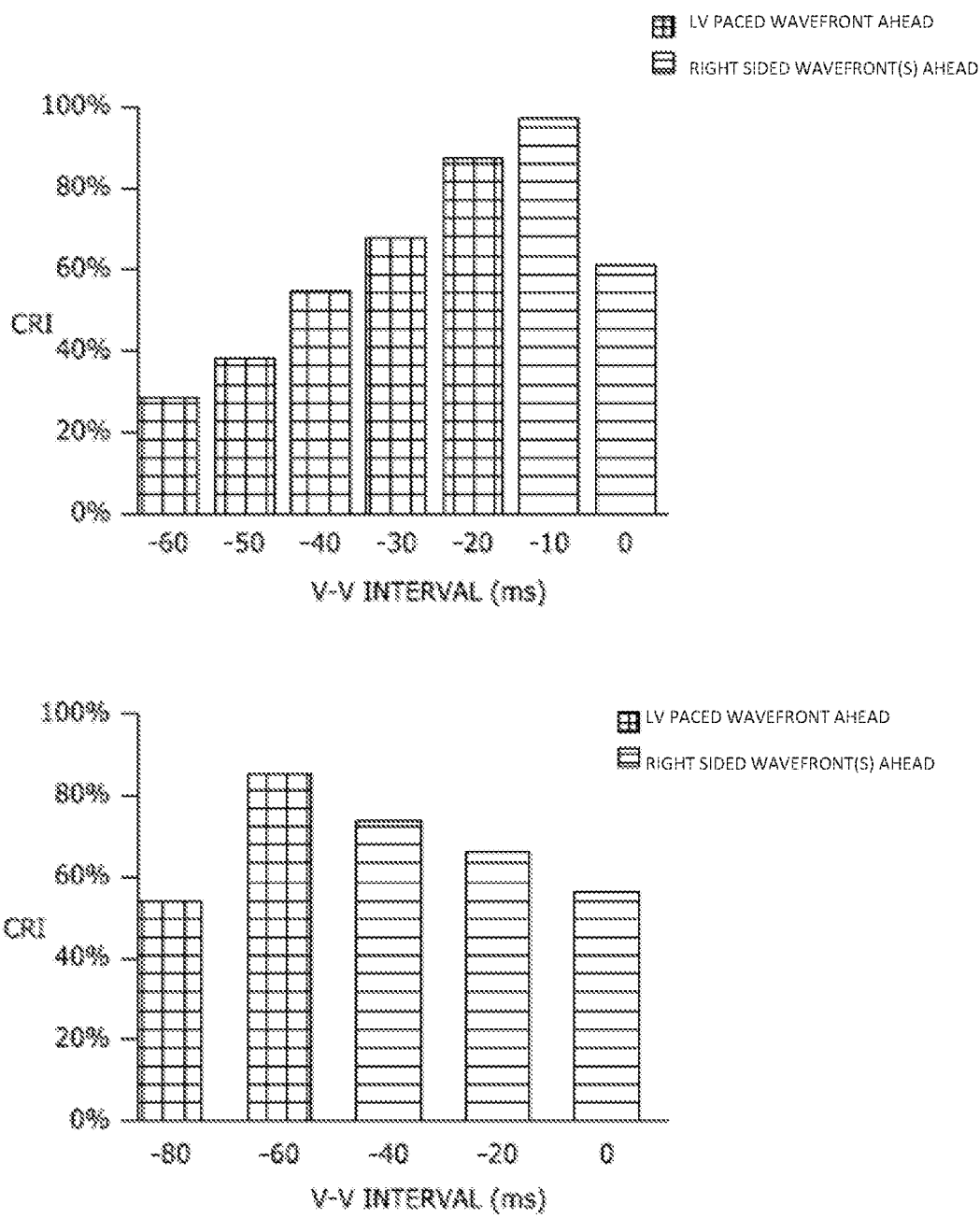

Instead of using the electrode configuration from FIG. 2, a 53-electrode ECG belt was used to acquire data for the study. The ECG belt measures unipolar ECGs using 17 anterior and 36 posterior electrodes on the upper torso. FIG. 22 shows the ECG belt electrograms from a patient with LBBB with CRT off, at standard CRT setting and at optimal CRT setting. The steepest slope of each electrogram and the time between earliest and latest steepest slopes were demarcated. The 17 anterior electrograms were matched with each of the 36 posterior electrograms to generate 612 pairs and the area between each pair of electrograms (shaded area) was calculated. The beginning and end of each area was defined based on the earliest and latest steepest slope respectively rather than the onset and end of the QRS complex as these time-points were more consistently and reproducibly identified. Mean area under all paired curves (AUC) was negative if the dominant wavefront was anterior to posterior and positive if posterior to anterior. Cardiac resynchronization index (CRI) was calculated as the % change in AUC at any setting as compared to native.

12 patients with CHB and 2 patients with atrial fibrillation were in the study. FIGS. 23A-E show ECG belt electrograms and CRI in a patient with CHB over a range of VV delays (A) and similar graphs of CRI over a range of VV delays (B) in 6 other patients. As the LV was preactivated from 0 to −80 ms (2A), waveform morphology changed with progressive decrease in anterior and posterior amplitudes and eventual "flipping" of many individual electrograms. AUC decreased and CRI increased to peak at LV preactivation. Dose response curves were observed in the 6 patients shown (2B) and in all 14 patients studied. The mean VV offset with best CRI was LVp 40+/−18 ms ahead of RVp. Mean CRI at the best VV offset (90+/−8.5%) was significantly (p<0.001) greater than the CRI at VV=0 (54.2+/−23.3%).

Figure 24A:
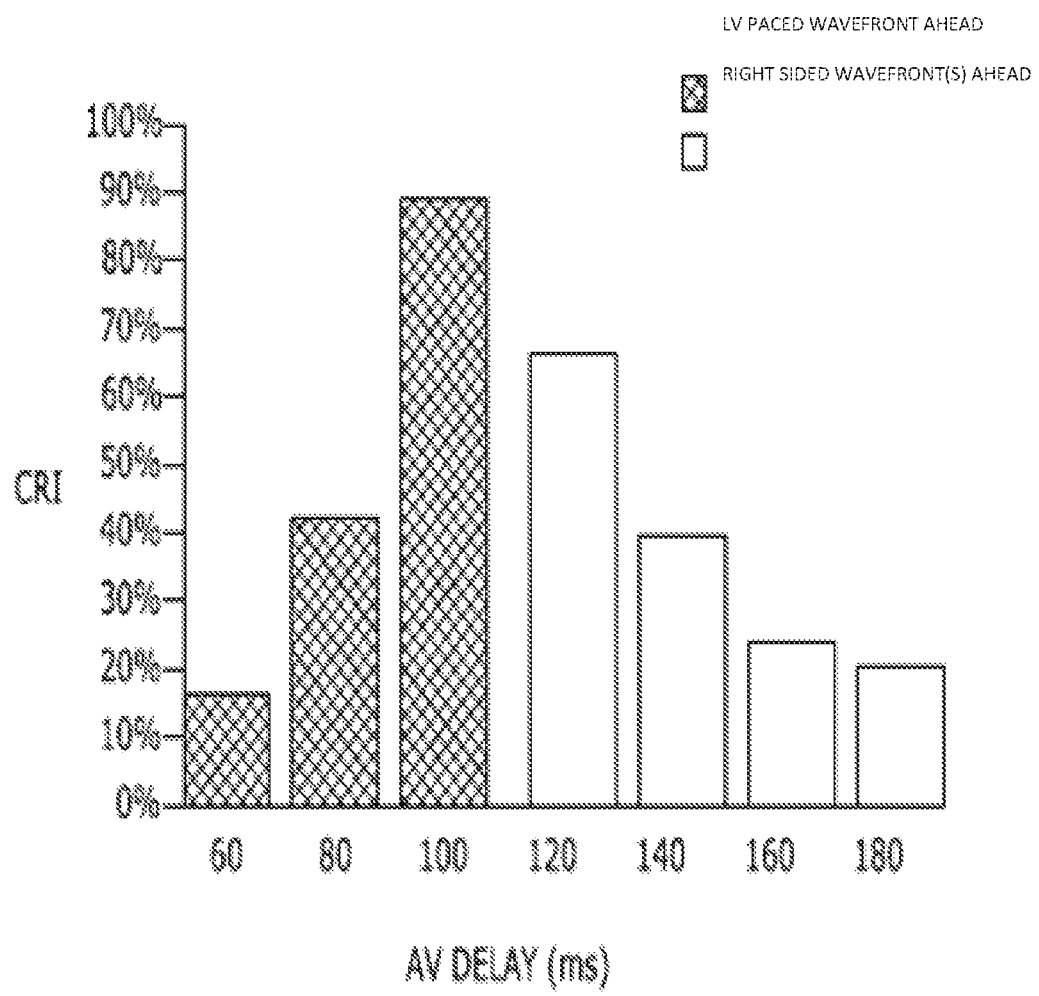
Figure 24B:
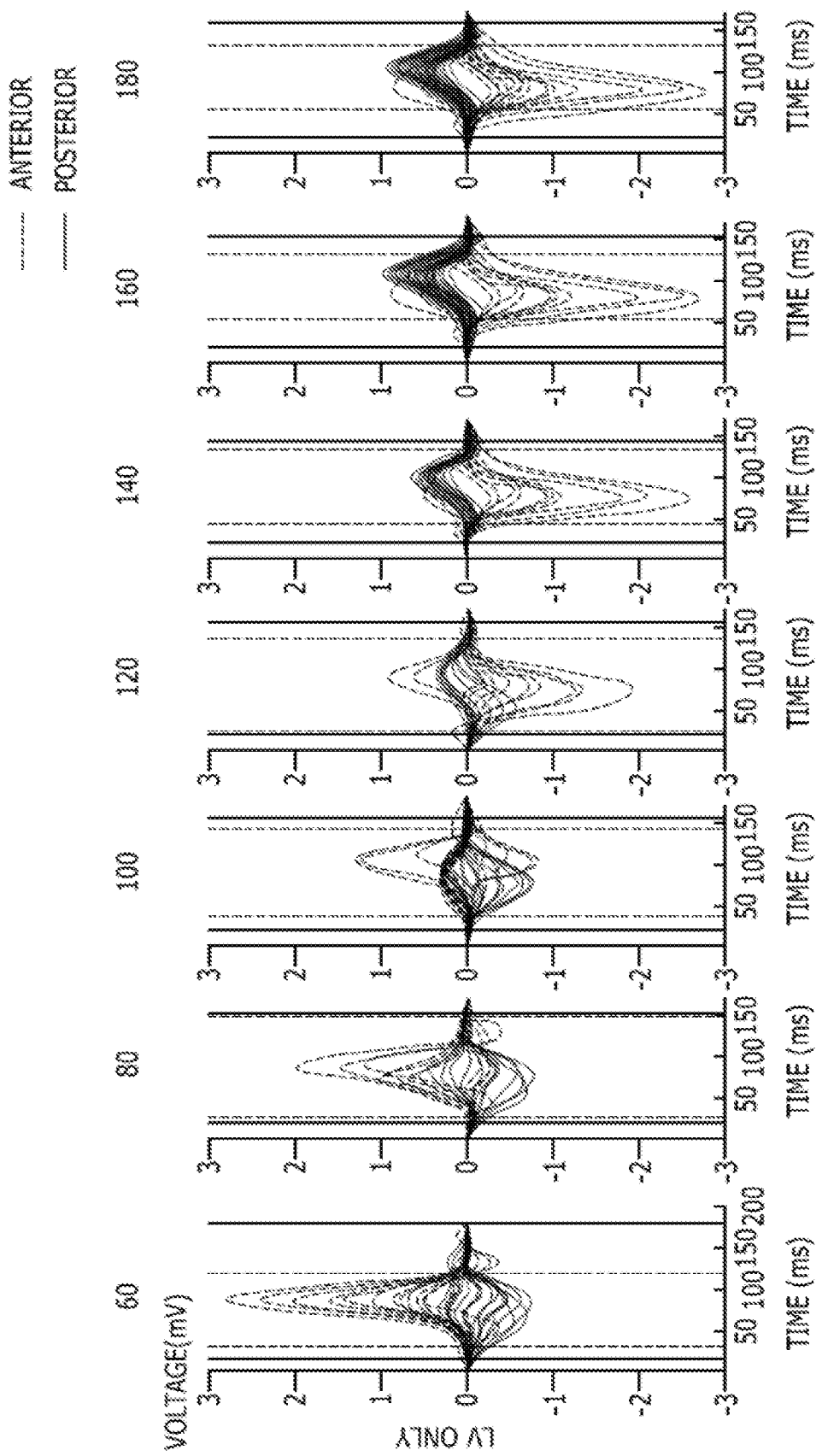
Figure 24C:
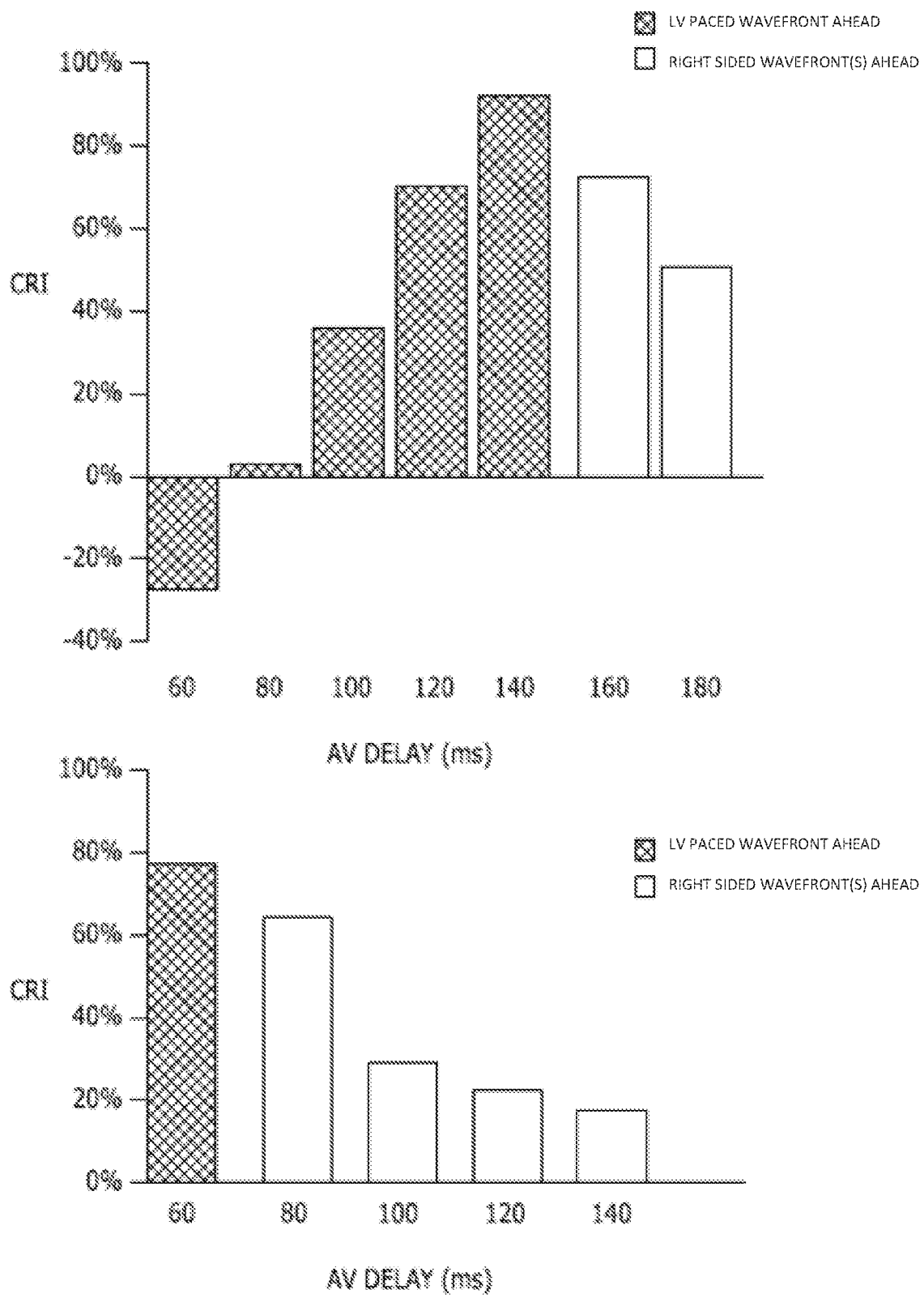
Figure 24E:
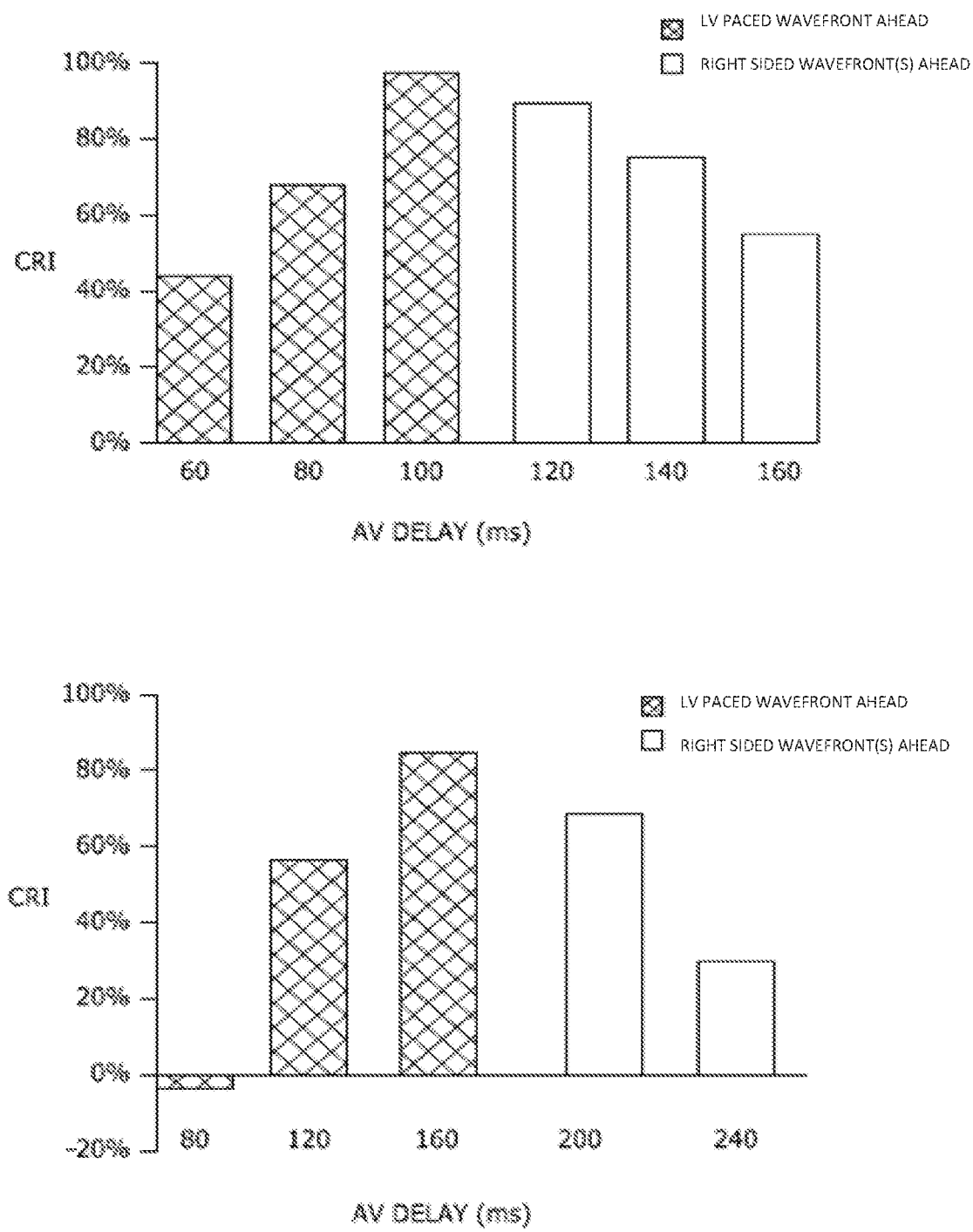
Figure 25A:
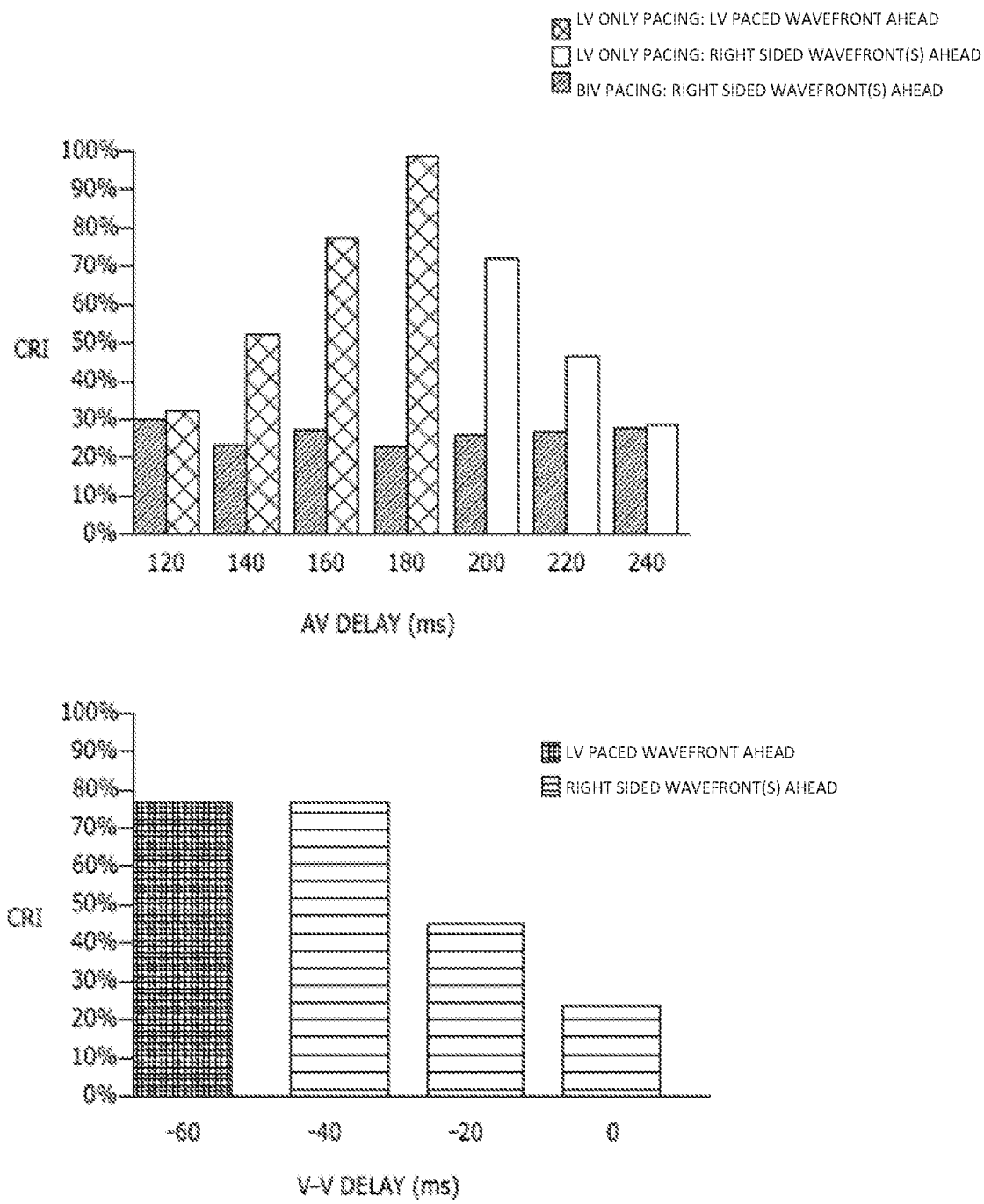
FIGS. 25A-D show depictions of electrograms and CRI graphical representations for a single patient over a range of AV delays and VV delays.
Figure 25B:
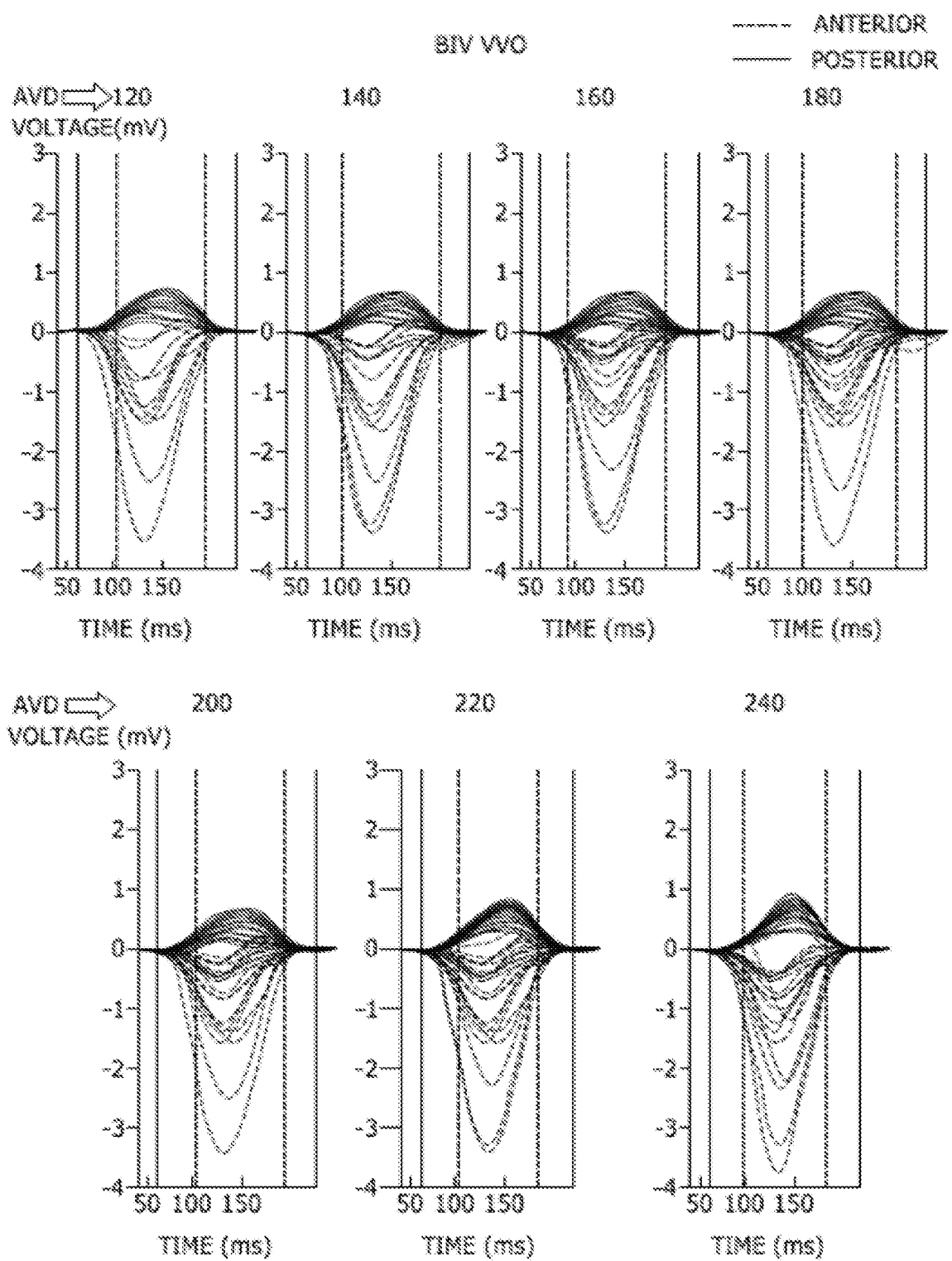
Figure 25C:
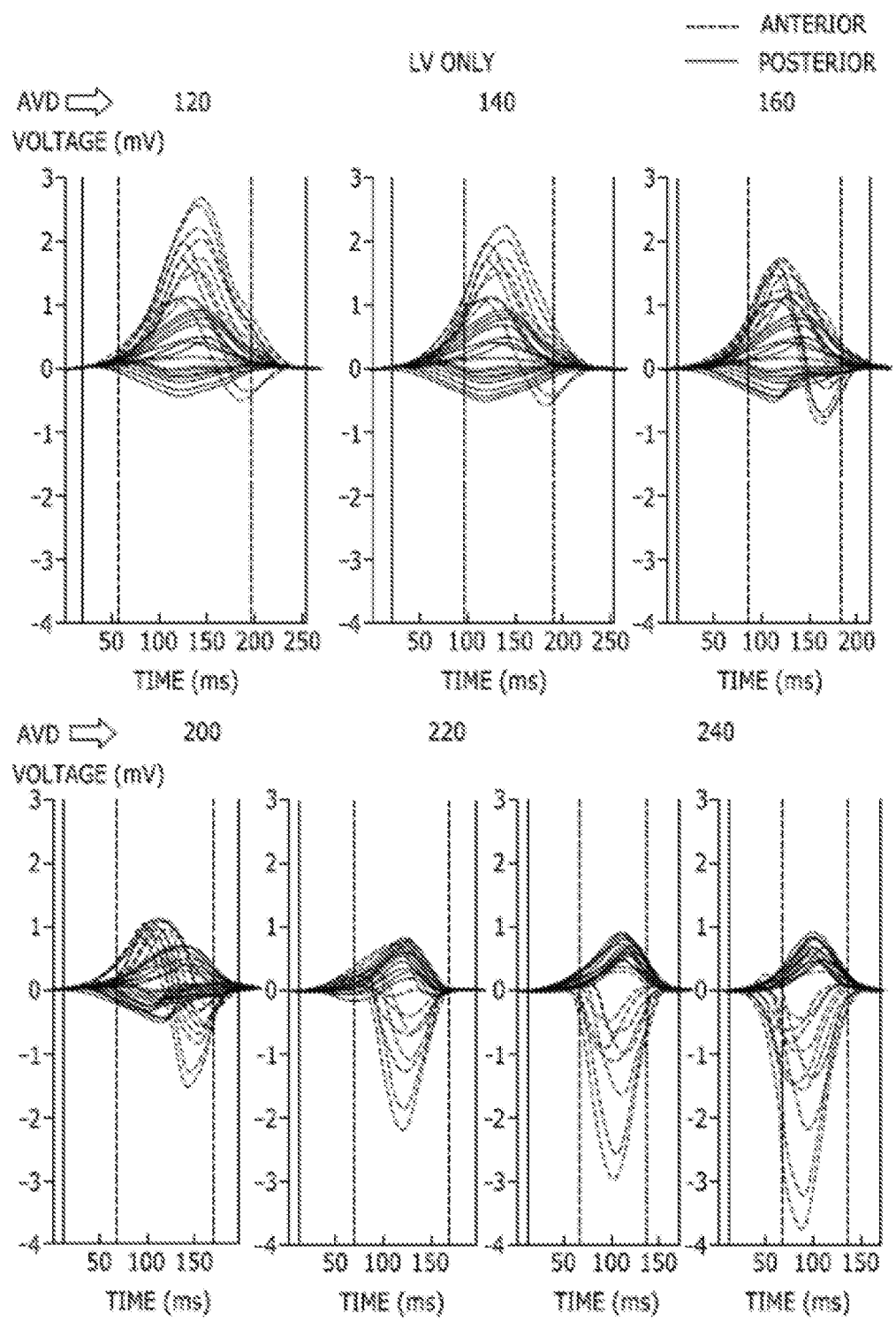
Figure 25D:
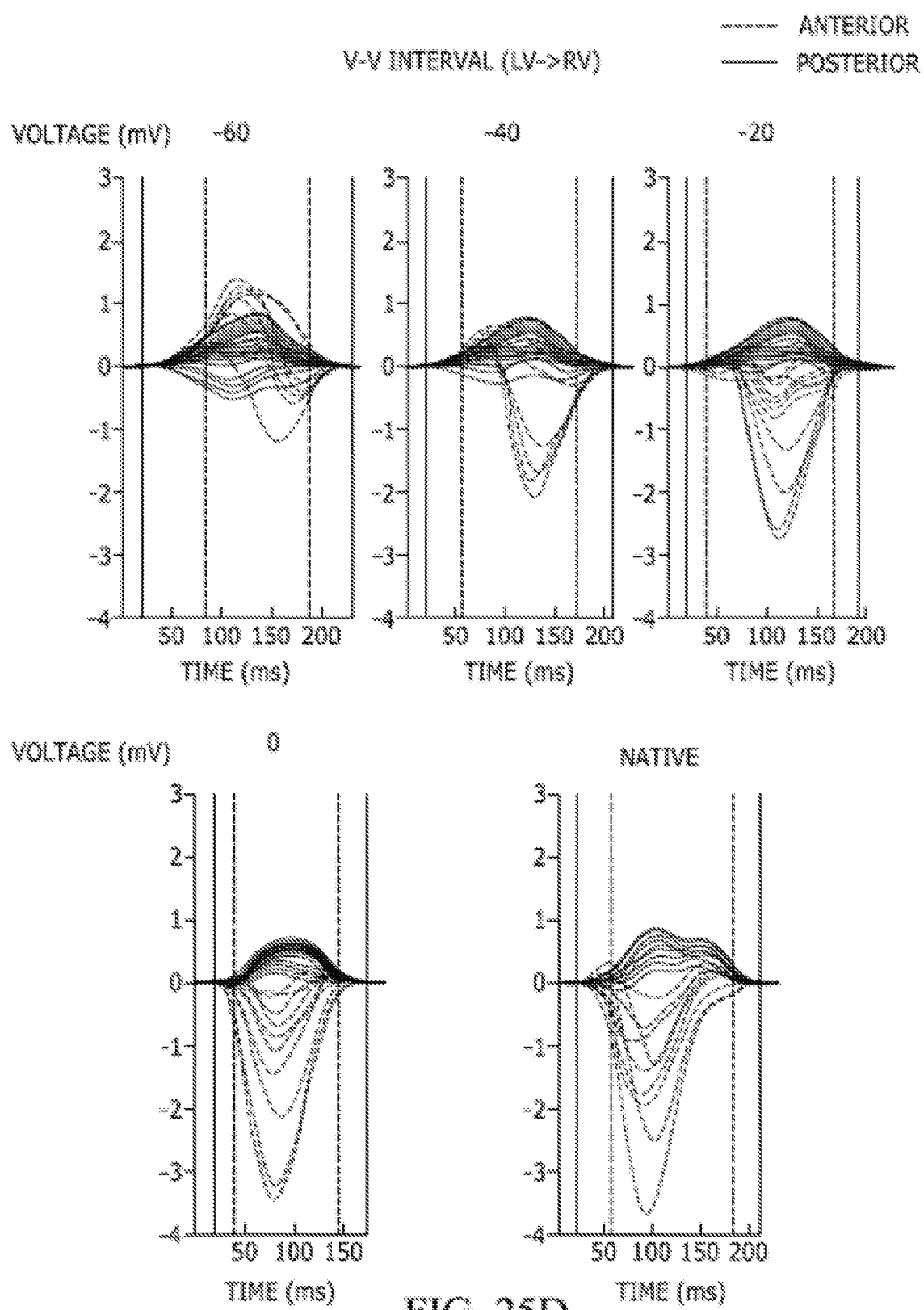
Figure 26B:
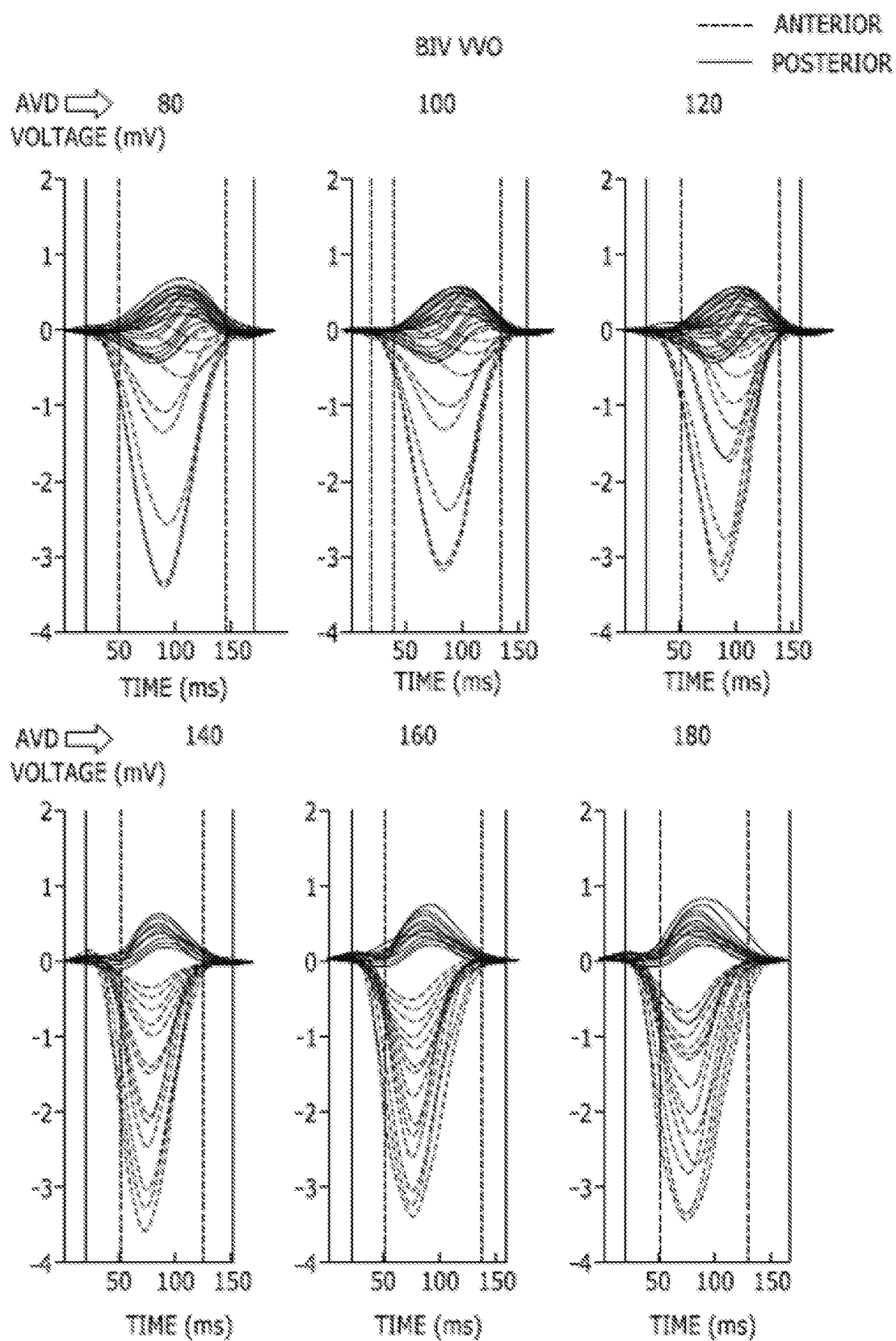
Figure 26C:
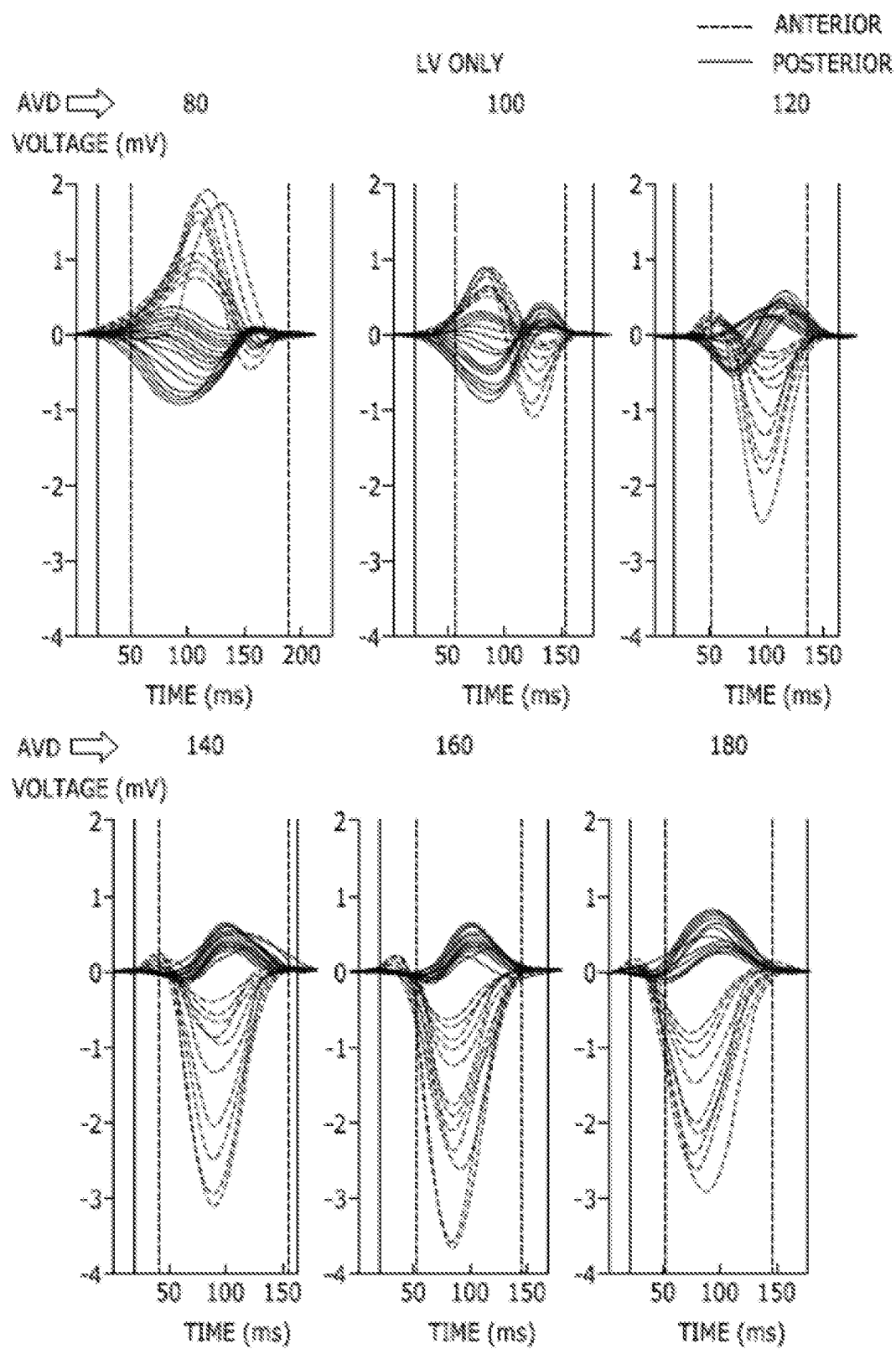
Figure 26D:
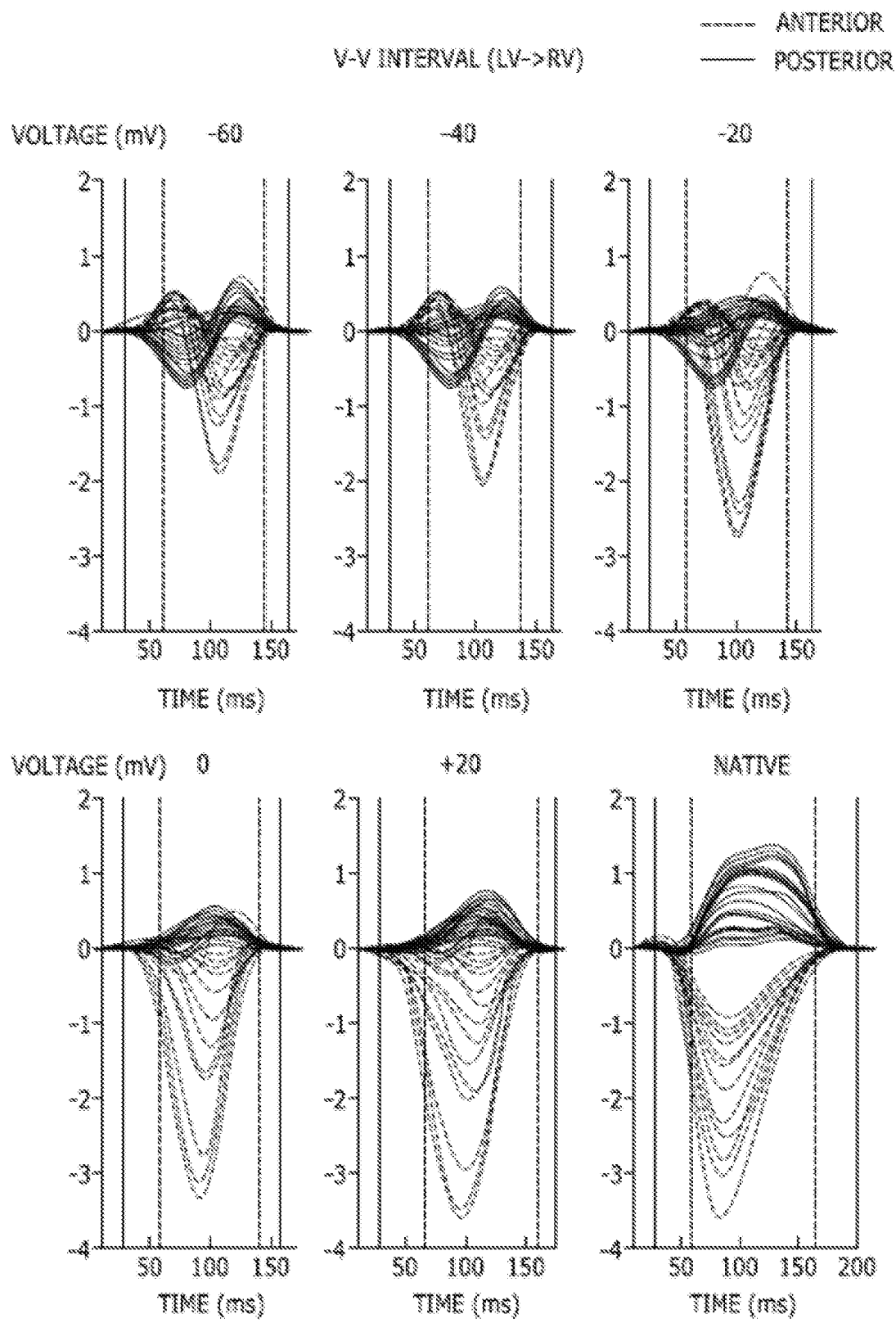
Figure 27A:
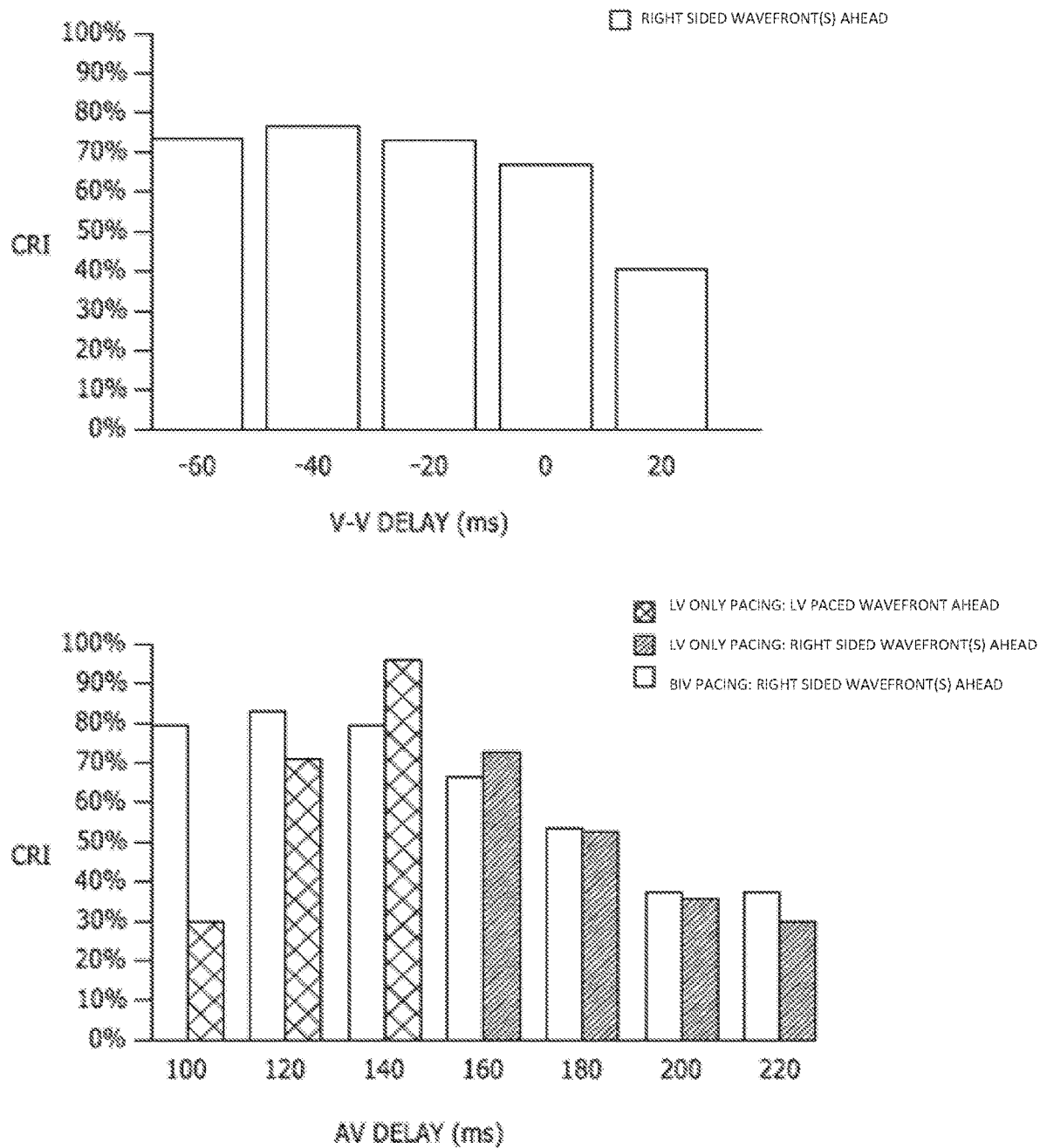
FIGS. 27A-D show depictions of electrograms and CRI graphical representations for a single patient over a range of AV delays and VV delays.
Figure 27B:
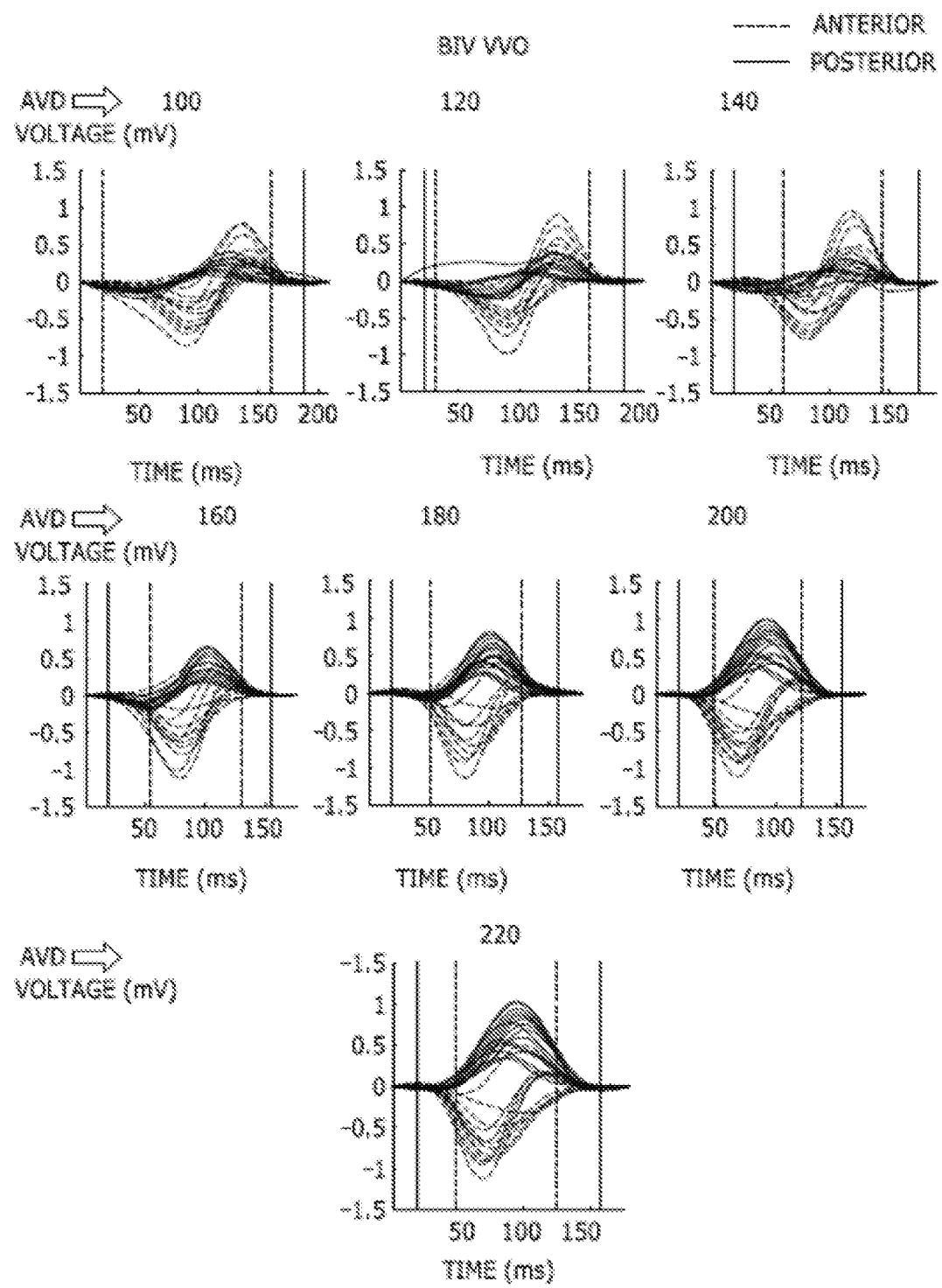
Figure 27C:
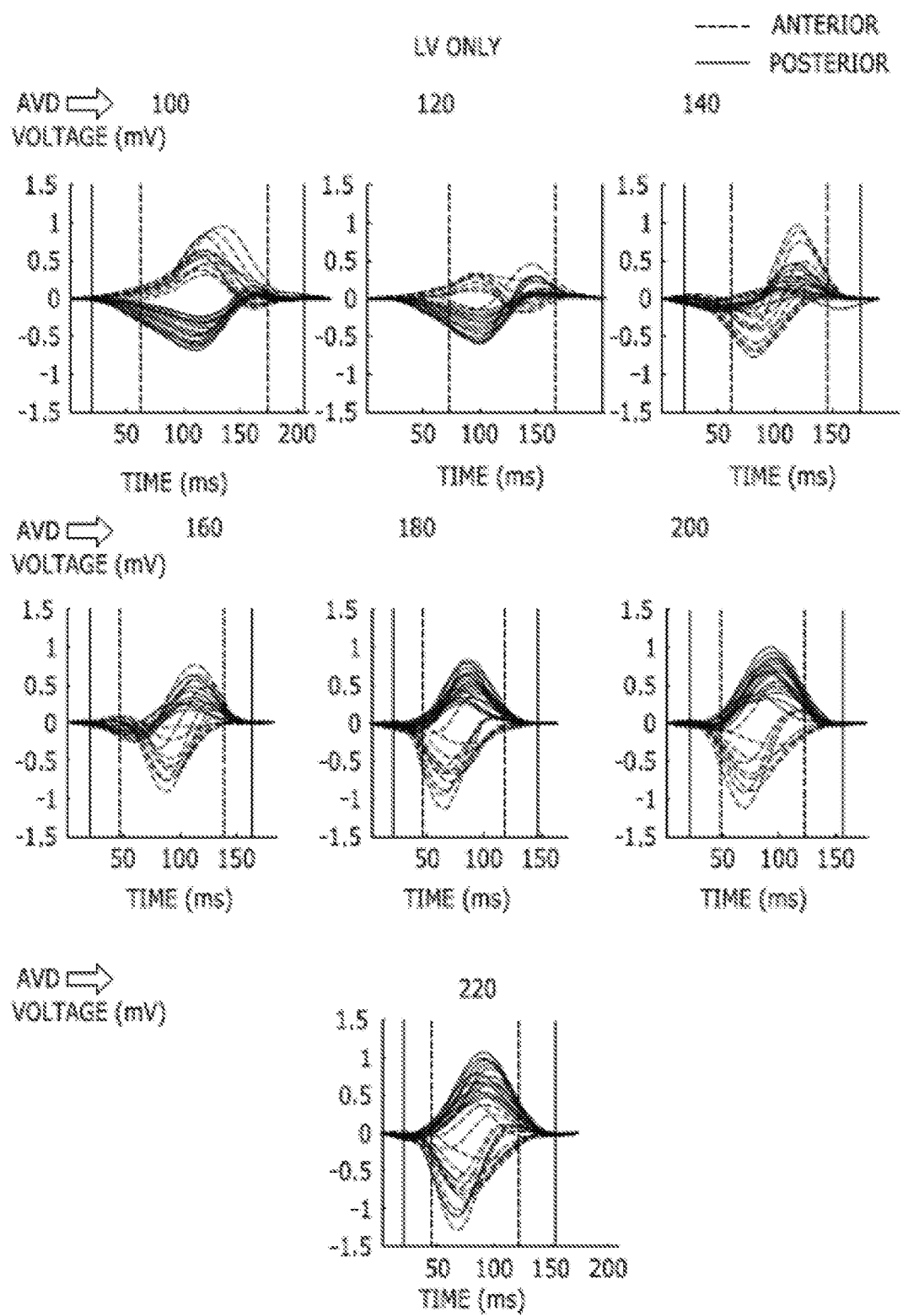
Figure 27D:
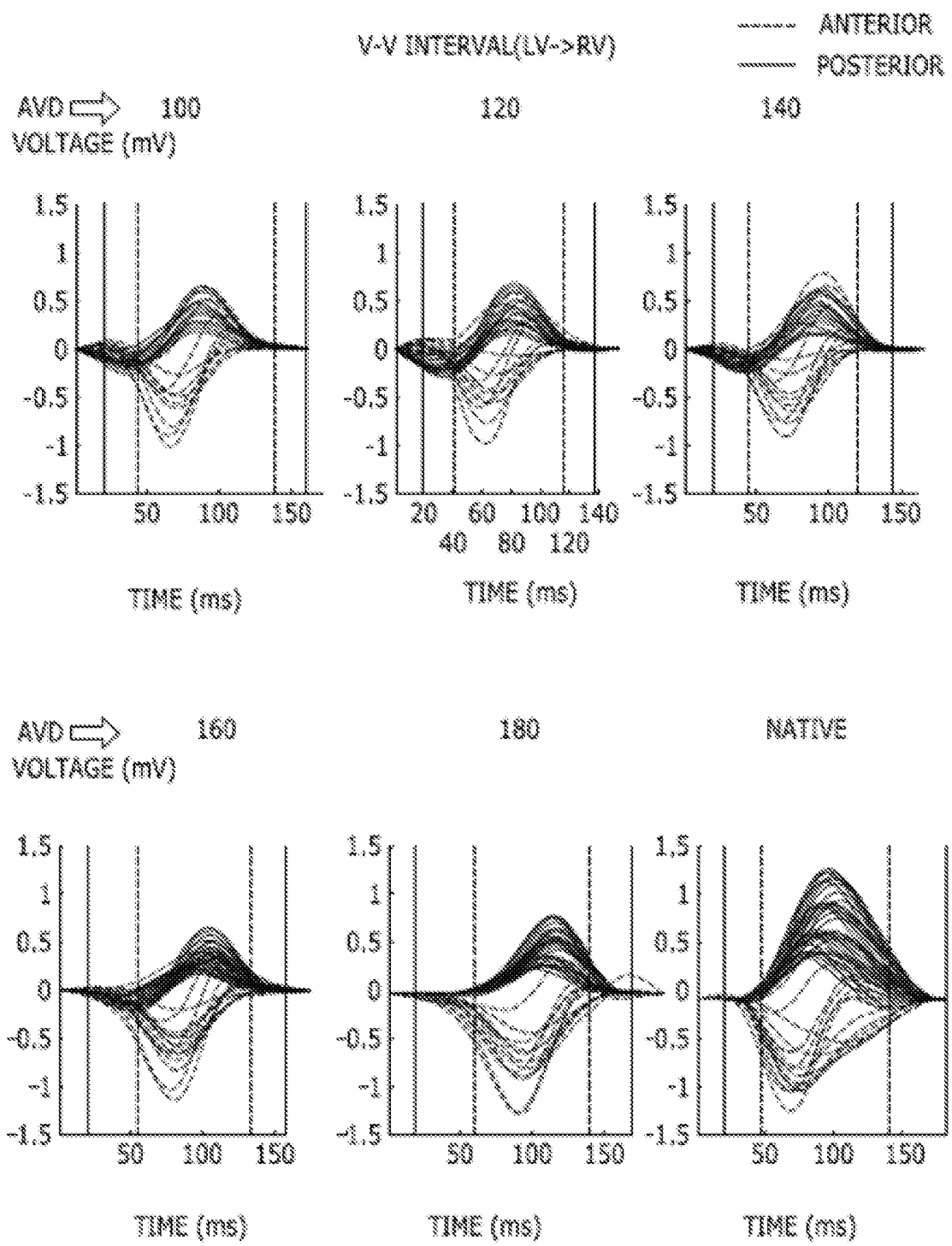

FIGS. 24A-E shows depictions of electrograms and CRI graphical representations for multiple patients during LV only pacing over a range of AV delays. For example, LV-only pacing was studied in 70 patients. In FIGS. 24A and 24B, a short AVD (60 ms) resulted in flipping of anterior and posterior electrograms as compared to native with the LVp wavefront way ahead of the native wavefront and low CRI of 15.9%. As AVD was increased the anterior and posterior electrogram amplitudes decreased, the AUC decreased and CRI improved to peak at 88.9% at an AVD of 100 ms. As AVD increased further, the electrogram morphology progressively became closer to the native LBBB electrogram morphology and CRI declined. In FIGS. 24C-E, similar dose-response relationships were seen between AVD and CRI with the LVp wavefront always ahead of the native wavefront at short AVDs and the native wavefront always ahead of the LVp wavefront at relatively long AVDs. In all 70 patients studied there were similar dose-responses seen. The best CRI (mean 89.6%+/−8%) was found at a mean AV delay of 116 ms+/−44 ms (61.8+/−12% of. As-RVs interval), 68+/−22 ms shorter than the As-RVs interval.

Sixty-one of the 70 patients with LV-only data (87.1%) also had data collected during simultaneous and sequential BiV pacing. CRI at a short AVD with BiV pacing was used to divide patients into 3 relatively equal subgroups since RVp and LVp wavefronts fuse, with little contribution from the native wavefront, at short AVD. CRI was <50% in 21 (34.4%), 50-75% in 21 (34.4%) and >75% in 19 (31.2%) patients. FIGS. 25A-D show ECG Belt electrograms and CRI graphs in a patient, with the RVp wavefront far ahead of the LVp wavefront (CRI 30%) when BiV pacing at short AVD. As AVD was increased there was minimal change in electrogram morphology or CRI. In contrast, with LV-only pacing at short AVD the anterior electrograms were flipped consistent with the LVp wavefront far ahead of the native wavefront. CRI was low but gradually increased to peak at 99% at an AVD of 180 ms. As AVD increased further, the native wavefront moved progressively further ahead of the LVp wavefront and CRI decreased. With sequential BiV pacing at a paced AVD of 150 ms, preactivation of the LV lead progressively flattened the electrograms and increased CRI with best CRT setting likely at VV −50 (half-way between VV −40 ms and VV −60 ms).

FIGS. 26A-D shows depictions of electrograms and CRI graphical representations for a single patient over a range of AV delays and VV delays. For example, the RVp wavefront was modestly ahead of the LVp wavefront during BiV pacing at a short AVD (CRI 70%). As AVD was increased, CRI gradually decreased due to increased anterior to posterior electrical activity generated by the native wavefront. At AVD of 140 ms the BiV paced and LV-only paced electrograms were nearly identical, consistent with fusion of native and LVp wavefronts with minimal contribution from the RVp wavefront. LV-only pacing resulted in a dose-dependent increase in CRT that peaked at an AVD of 100 ms and then gradually decreased. Sequential BiV pacing at an AVD of 120 ms demonstrated a consistent and steady increase in CRI as LV preactivation increased.

FIGS. 27A-D show data in a patient where the RVp and LVp wavefront are fairly well-timed (CRI 80% at an AVD of 100 ms). Increasing AVD resulted in a gradual decrease in CRI as the combined RVp and native wavefronts got further ahead of the LVp wavefront. As in the previous patients, LV-only pacing produced a peak CRI with a gradual decrease in CRI as AVD was increased further (due to the native wavefront moving increasingly ahead of the LVp wavefront). Sequential BiV pacing in this patient was performed by keeping the A-LVp interval constant at 160 ms and sequentially prolonging the A-RVp interval. This resulted in only a minimal change in electrogram morphology and CRI because at an AVD of 160 ms, the RVp wavefront was not contributing much to fusion (electrogram morphology during BiV pacing and LV-only pacing at an AVD of 160 ms was nearly identical). Thus, delaying the RVp wavefront by 20 to 60 ms did not significantly alter the fusion of the native and LVp wavefronts.

Only 5 (8.2%) patients had a positive AUC (LVp wavefront ahead of RVp wavefront) during BiV pacing at a short AVD, and CRI was >75% in all of them. The mean CRI with BiV pacing at a short AVD was 57.2+/−30%. Best CRI during BiV pacing averaged only 7.3+/−14.7% higher. With sequential BiV pacing, best CRI occurred at VV=0 in only 3 (5%) patients. The best CRI was found with LV preactivation of 20 ms in 20 (33%), 40 ms in 19 (31%) and 60 ms in 19 (31%) patients. Best CRI during sequential BiV pacing was 83.9+/−13% and occurred at LV preactivation of 40.2+/−20 ms. CRI at standard device settings (VV=0 and AVD~70% of PR interval) was 49.9+/−23.2%. CRI at the best overall device setting was markedly better at 91.6+/−7.8% (p<0.001).

On average, the RVp wavefront is ~40 ms ahead of the LVp wavefront, and the native wavefront is ~70 ms ahead of the LVp wavefront. CRI with BiV pacing at a short AVD helps to determine if the RVp and LVp wavefronts are synchronized. Changes in AVD with BiV pacing do not usually produce substantial improvements in electrical synchrony. In contrast, in all patients studied, starting at a short AVD and gradually increasing AVD with LV-only pacing produces a dose-dependent increase in CRI with peak and then gradual decrease. Sequential BiV pacing with LV pre-activation often increases CRI by moving the LVp wavefront (which is typically delayed) further ahead of the RVp and/or native wavefronts. BiV pacing at standard settings (VV=0, AVD ~70% PR interval) produces an ~50% increase in CRI as compared to native LBBB which can be improved markedly to a CRI of ~92% with optimal programming using the ECG Belt.

In patients with atrial fibrillation or CHB, there is no native wavefront to fuse with the LVp and RVp wavefronts and thus the effects of pure BiV pacing can be studied. The degree of wavefront fusion with simultaneous BiV pacing in these patients is determined by the location of the LV and RV leads and the conduction properties (latency, block, wavefront conduction velocity) of the LV myocardium. Wavefront fusion and cancellation during simultaneous BiV pacing, as measured by CRI, varies from −3.1% to 89.2% in these patients with a mean of 54%. In all of these patients the RVp wavefront was ahead of the LVp wavefront with simultaneous RV and LV pacing. The only programming option to improve wavefront fusion and electrical synchrony in these patients is changing VV delay. LV preactivation by a mean of ~40 ms resulted in an improvement in CRI from 54% to 90%.

LV-only pacing in patients with intact AV node conduction was used to investigate the effects of LVp wavefront and native wavefront fusion and cancellation. LV pacing produced a consistent effect on wavefront fusion and cancellation in all 70 patients studied. At very short AV delays, the LVp wavefront was always ahead of the native wavefront. As AV delay was gradually lengthened, CRI improved as a result of increased electrical fusion and cancellation and was seen as a reduction in first posterior, and then anterior, QRS amplitude in combination with a shortening of QRSd. The majority (90%) of patients achieved a peak CRI of >80% when assessing AV delay at 20 ms increments. Once peak CRI was reached, further increase in AV delay resulted in a gradually decreasing CRI due to the native wavefront increasingly moving ahead of the LVp wavefront and exemplified by gradual increase in the anterior and posterior electrogram amplitudes. On average, the peak CRI occurred at an AV delay~70 ms shorter than the PR interval. Although peak CRI occurred at a mean AV delay of 62% of native PR interval, there was considerable variation and individual optimization was required to achieve optimal wavefront fusion.

Changes in AV delay at constant VV delay of 0 resulted in varying degrees of fusion among native, RVp and LVp wavefronts. At short AV delays, the RVp wavefront consistently preceded the native wavefront and the patient received BiV pacing without major contribution from the native wavefront. As AV delay was increased, the native wavefront increasingly contributed to LV depolarization. The contribution of the native wavefront to LV depolarization could be determined by the change in waveform morphology and the change in CRI, with the typical response an increase in anterior waveform amplitude and a reduction in CRI due to the combined native and RVp wavefronts providing a more dominant anterior to posterior wavefront. Once AV delay was within about 20-30 ms of native PR interval, the RVp wavefront contributed little, if anything, to LV depolarization as shown by no change in morphology or CRI between electrograms obtained with or without RV pacing at the same longer AV delay. At these longer AV delays during BiV pacing, the patient was effectively receiving LV-only pacing fused with native conduction, but at too long of an AV delay, resulting in large dominance of the native over the LVp wavefront.

The mean peak CRI over a range of AV delays during simultaneous BiV pacing was significantly lower (p<0.001) than that during LV-only pacing across the same range of AV delays (63.4% vs 89.6%). This is likely because the RVp wavefront is dominant in almost all patients and markedly ahead of the LVp wavefront. Without pre-activating the LV lead in these patients, the RVp wavefront (or the combined right sided RVp and native wavefronts) typically remained ahead of the LVp wavefront over the entire range of AV delays. In patients with a relatively high CRI during BiV pacing at a short AV delay, LV pre-activation only needed to be 20 ms or so in order to optimize electrical synchrony, since the RVp wavefront was only slightly ahead of the LVp wavefront. In patients with a low CRI during BiV pacing at a short AV delay, LV pre-activation needed to be 40-60 ms to optimize LV electrical synchrony since the RVp wavefront was far ahead of the LVp wavefront.

As mentioned above, there is no standard, well-accepted methodology for optimizing CRT programming and the vast majority of patients are left at their initial CRT device settings. Although 12-lead ECG optimization can be performed and has been shown to be of value, the above system and methods offers a number of benefits. For example, the above system and methods may detect changes in wavefront fusion and cancellation much better than 12-lead ECG due to the increased number of leads and the presence of posterior leads. Since the LV is positioned mostly posteriorly in the chest, the posterior electrodes provide a great deal of information not obtained by anterior leads. The ECG belt methodology described here offers a number of potential benefits for use in optimizing CRT: it is non-invasive, practical, fast (30 settings can be tested in about 30 minutes), and independent of observer bias (all measurements are automated).

Figure 28:
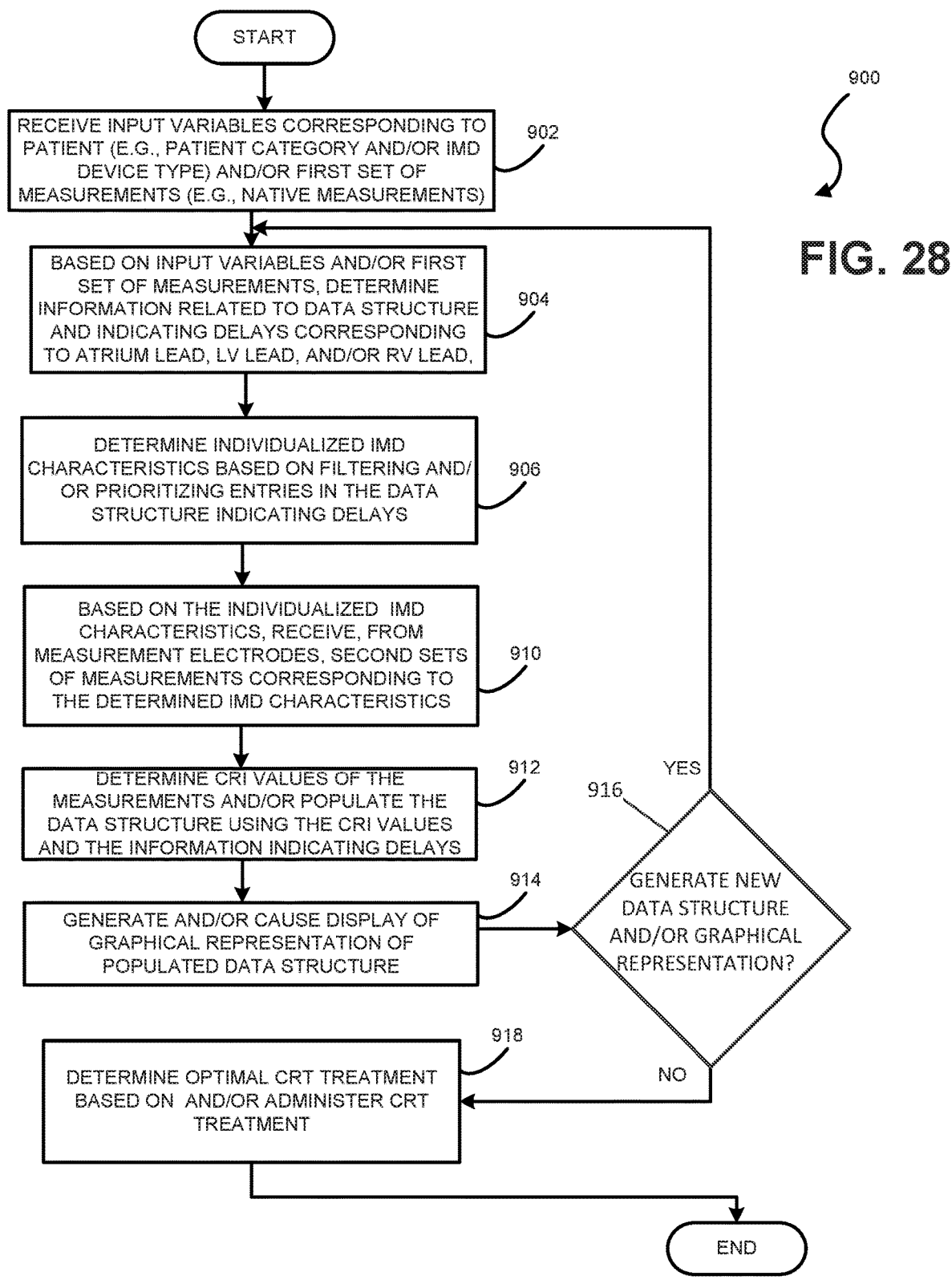
FIG. 28 is another block diagram of an exemplary method for optimizing cardiac resynchronization therapy (CRT) treatments.

FIG. 28 is a block diagram of another exemplary processing sequence 900 for optimizing cardiac resynchronization therapy (CRT) treatments (e.g., determining one or more individualized IMD characteristics, CRI values, and/or optimal CRT treatments). Processing sequence 900 will be described with reference to the system 100 illustrated in FIGS. 1-7. However, any suitable structure, system, component, device, and/or apparatus can be employed.

Furthermore, one or more blocks from processing sequence 900 may function similarly to the blocks from processing sequences 200-500 described above. For example, similar to processing sequence 200, the computing apparatus 140 may receive native measurements (first measurements) and second measurements for individualized IMD characteristics (e.g., IMD delay characteristics such as AV, BiV, and/or VV delays). Then, the computing apparatus 140 may determine CRI values and optimal CRT treatments (e.g., optimal delays to apply to the IMD 16 based on cancellation of wavefronts between leads 18, 20, and/or 22).

Additionally, and/or alternatively, the computing apparatus 140 may determine information for a data structure, such as a matrix. The information may indicate different delays to apply to the IMD 16 to use for the second measurements and the CRI values. Furthermore, additionally, and/or alternatively, the computing apparatus 140 may generate and cause display of a heat map representing the CRI values. In some instances, using a data structure with the CRI values and/or a heat map may make it easier for a user, such as a doctor, to determine optimal CRT treatments. For example, the heat map that is generated from CRI values may assist a doctor in determining optimal settings for the 1 MB 16 (e.g., the doctor can easily see sections of optimal CRT settings to use for the CRT programming). In other instances, by using the data structure with the CRI values and/or a heat map may allow a more robust and standardized process of determining optimal CRT treatment. For example, as mentioned above, there is no standard, well-accepted methodology for optimizing CRT programming. As such, the information for the data structure may indicate priorities, such as always acquired, usually acquired, and/or sometimes acquired, which may help standardize the process for optimizing CRT programming.

In operation, at block 902, the computing apparatus 140 may receive one or more input variables corresponding to a patient 14 (e.g., patient category and/or 1 MB device type) and/or one or more first set of measurements (e.g., the native measurements). For example, similar to block 202 above, the computing apparatus 140 may receive the one or more the native measurements from the measurement electrodes 112 and/or 114. For instance, while the leads 18, 20, and/or 22 of the 1 MB 16 are turned off, the measurement electrodes 112 and/or 114 may measure electrical information such as cardiac activation signals (e.g., depolarization and/or repolarization) of the patient's heart 12. The measurement electrodes 112 and/or 114 may provide the electrical information to the interface/amplifier circuitry 116. The interface/amplifier circuitry 116 may amplify the signals and then provide the signals the computing apparatus 140.

Additionally, and/or alternatively, similar to block 302 above, the computing apparatus 140 may receive one or more input variables (e.g., user input) corresponding to a patient, such as patient 14. For example, the computing apparatus 140 may receive, from the input apparatus 142, the name of the patient 14, the date of birth of the patient 14, the date the 1 MB 16 was implanted in the patient 14, the etiology heart failure (HF) (e.g., the ischemic cardiomyopathy (ICM), non-ischemic cardiomyopathy (NICM), and/or others), the patient category, and/or the IMD device type (e.g., the manufacturer of the IMD 16). The patient category may include, but is not limited to, atrial fibrillation/flutter (AF), complete heart block (CHB), left branch bundle block (LBBB), interventricular conduction delay (IVCD), right ventricular pacing (RVP), Narrow, and/or right branch bundle block (RBBB). In some instances, as described above at block 306, based on received native measurements, the computing apparatus 140 may determine the patient category (e.g., LBBB, RBBB, IVCD, RVP, Narrow, CHB, and/or AF).

At block 904, based on the input variables and/or the native measurements, the computing apparatus 140 may determine information related to a data structure (e.g., a template, table, matrix, and/or another type of data type or structure) and indicating delays corresponding to an atrium lead (e.g., RA lead 22), the LV lead 20, and/or the RV lead 18. For instance, the delays for the RA lead 22, LV lead 20, and the RV lead 18 may include, but not limited to, delays from the RA lead 22 to the RV lead 18 (A-RV delays) and/or delay from the RA lead 22 to the LV lead 20 (A-LV delays).

Figure 29:
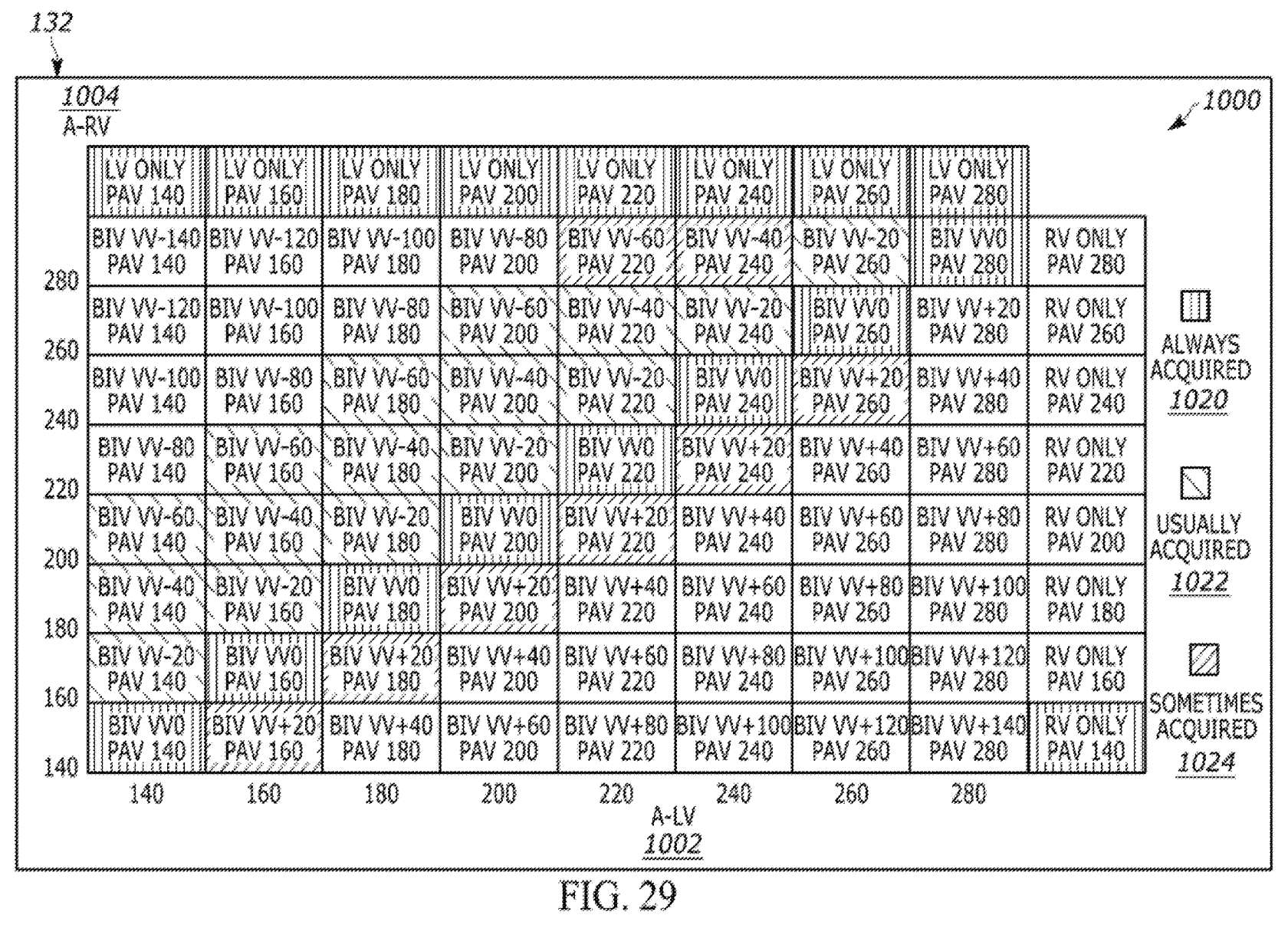
Figure 30:
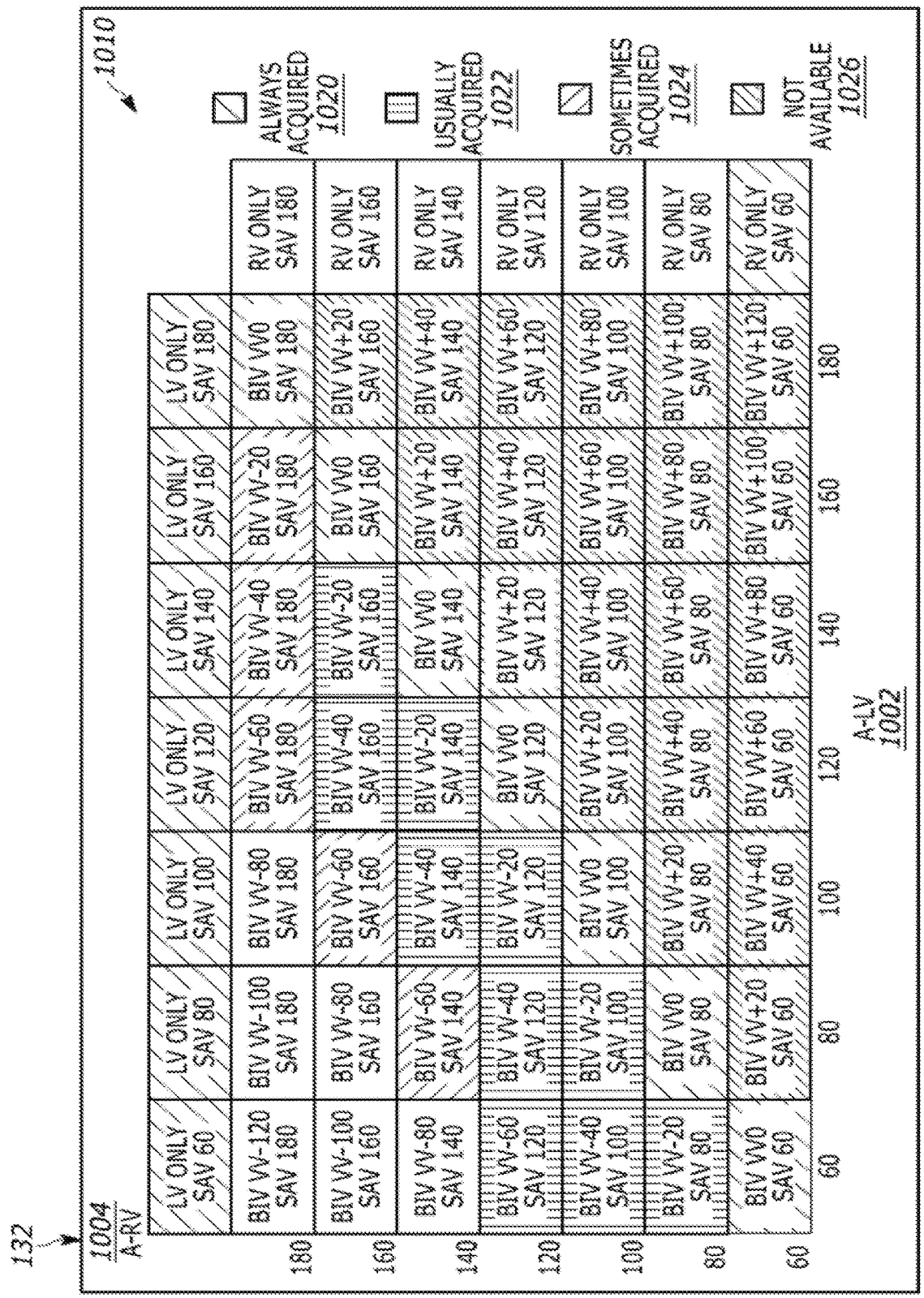
FIG. 30 is another exemplary graphical user interface depicting another data structure used to determine optimal CRT treatments.

FIGS. 29 and 30 show exemplary data structures for two patients using two different input variables. For example, in data structure 1000, the patient is using a first device type where VV −20 ms at atrial paced AV delay (PAV) 160 ms (e.g., paced from atrium or RA lead 18 paced) means A-RV is 180 ms and A-LV is 160 ms. In matrix 1010, the patient is using a second device type where VV −20 ms at atrial sensed AV delay (SAV) 100 ms (e.g., sensed from atrium, RA lead 18 sensed) means A-RV is 100 ms and A-LV is 80 ms. In other words, FIG. 29 shows a matrix 1000 with the x-axis 1002 indicating the A-LV delay and the y-axis 1004 indicating the delay from the A-RV delay. The A-LV delay may be a delay or timing difference between the native pulse (IMD 16 operating in an AS mode)/RA lead 22 generated pulse (IMD 16 operating in an AP mode) and the LV lead 20 generated pulse (e.g., an LV pulse). The A-RV delay may be a delay or timing difference between the native pulse (IMD 16 operating in an AS mode)/RA lead 22 generated pulse (IMD 16 operating in an AP mode) and the RV lead 18 generated pulse (e.g., an RV pulse). If the A-LV delay is the same as the A-RV delay (e.g., the bottom left entry showing that the A-LV delay is 140 ms and A-RV delay is 140 ms), then it is a simultaneous BiV delay described above (e.g., a BiV delay of 140 ms). If they are different, then it is BiV delay with a VV delay. For example, the entry shown with A-LV of 140 ms and A-RV of 160 ms means that there is a PAV delay of 140 ms and a VV delay of −20 ms. Similarly, the entry shown with A-LV of 200 ms and A-RV of 240 ms means that there is a PAV delay of 200 ms and a VV delay of −40 ms. The top entries show LV only delay characteristics (e.g., the entry showing A-LV of 200 ms is an LV only delay of 200 ms). The right entries show RV only delay characteristics (e.g., the entry showing A-RV of 200 ms is an RV only delay of 200 ms). FIG. 30 shows another matrix 1010 for a second patient 14 with the x-axis 1002 indicating the A-LV delays and the y-axis 1004 indicating A-RV delays.

In some examples, the information indicating the delays may include priority information such as always acquired, usually acquired, and/or sometimes acquired. The computing apparatus 140 may use the patient category, device type, and/or native measurements to determine the priority information.

In some variations, the computing apparatus 140 may determine the information indicating the delays for the data structure based on the patient category, IMD device type, and/or the native measurements. For example, the computing apparatus 140 may determine different A-LV delays and/or A-RV delays for the patient 14 based on the patient category, IMD device type, and/or first set of measurements. For instance, referring to FIG. 29, the computing apparatus 140 may determine the A-LV and/or A-RV delays and/or generate matrix 1000 based on determining the IMD 16 is a first 1 MB device type. Referring to FIG. 30, the computing apparatus 140 may determine the A-LV and/or A-RV delays and/or generate matrix 1010 based on determining the IMD 16 is a second IMD device type.

Additionally, and/or alternatively, the computing apparatus 140 may change the increments between each entry (e.g., 10 ms increments versus the 20 ms increments shown in FIGS. 29 and 30) based on the patient category, 1 MB device type, and/or the native measurements. Additionally, and/or alternatively, the computing apparatus 140 may determine the maximum delay (e.g., A-RV delay and/or A-LV delay) based on the PR interval of the patient 14. For example, referring to FIG. 29, if the computing apparatus 140 determines the PR interval of the patient 14 is 300 ms, then the computing apparatus 140 may determine the maximum A-RV delays and/or A-LV delays as 280 ms. The computing apparatus 140 may use the maximum delay and/or the increments between each entry to determine the different A-LV delays and/or A-RV delays for the patient 14.

Additionally, and/or alternatively, the computing apparatus 140 may determine the size of the data structure (e.g., a 9×9 matrix, an 8×8 matrix, a 7×7 matrix, and so on) based on the patient category, 1 MB device type, and/or the first set of measurements. Additionally, and/or alternatively, the computing apparatus 140 may determine the size of the data structure (e.g., a 9×9 matrix, an 8×8 matrix, a 7×7 matrix, and so on) based on the patient category, IMD device type, and/or the first set of measurements.

Additionally, and/or alternatively, if the input variables and/or the native measurements indicate AF and/or CHB, then the computing apparatus 140 may generate a first data structure type (e.g., first matrix). If the input variables and/or the native measurements indicate LBBB, IVCD, RVp, Narrow QRS, then the computing apparatus 140 may generate a second or different data structure type. Furthermore, if the input variables and/or the native measurements indicate RBBB, the computing apparatus 140 may generate a third data structure type that is different from the first or second data structures.

In some instances, the information for the different data structures including the delays and priorities may be stored in memory 152. For example, for each type of device, the memory 152 may store different information for each patient category. The different information may include the size of the data structure, the A-LV and A-RV delays, and the different priorities. For instance, the computing apparatus 140 may determine the IMD 16 is a first type of device and the patient category is LBBB. The computing apparatus 140 may retrieve the information from memory 152 for the first type of device and patient category LBBB, which may indicate the size of the data structure (e.g., an 8×8 matrix) and the entries with different priorities, such as the priorities always acquired 1020, usually acquired 1022, and sometimes acquired 1024 shown in FIG. 29. Then, based on the measured PR interval, the computing apparatus 140 may determine the maximum A-RV and A-LV delays (e.g., if the PR interval is 300 ms, then the maximum A-RV and A-LV delays are 280 ms). After, the computing apparatus 140 may use an interval, such as a pre-programmed, pre-defined, and/or user-defined interval, to fill in the rest of the A-RV and A-LV delays (e.g., reduce the 280 ms delays by 20 ms down to 140 ms).

Furthermore, if the computing apparatus 140 determines the IMD 16 is a first type of device and the patient category is RBBB, the computing apparatus 140 may retrieve different information from memory 152 for the first type of device and patient category. For example, the computing apparatus 140 may retrieve information corresponding to the data structure 1010 shown in FIG. 30 (e.g., the 7×7 matrix size and entries with the priorities always acquired 1020, usually acquired 1022, sometimes acquired 1024, and not available 1026). Then, based on the measured PR interval, the computing apparatus 140 may determine the maximum A-RV and A-LV delays (e.g., if the PR interval is 200 ms, then the maximum A-RV and A-LV delays are 180 ms). After, the computing apparatus 140 may use an interval, such as a pre-programmed, pre-defined, and/or user-defined interval, to fill in the rest of the A-RV and A-LV delays (e.g., reduce the 180 ms delays by 20 ms down to 60 ms).

At block 906, the computing apparatus 140 may determine individualized IMD characteristics based on filtering and/or prioritizing entries in the data structure indicating the delays. For example, entries from the generated data structure may have different priorities (e.g., a first, second, third, and so on ranking or priority). Based on the corresponding priorities, the computing apparatus 140 may determine individualized IMD characteristics to use. As mentioned previously and will be described in further detail below, the computing apparatus 140 provides (e.g., directly and/or displayed and provided via user input to the 1 MB 16) the individualized IMD characteristics to the 1 MB 16. Then, based on the individualized 1 MB characteristics, the computing apparatus 140 receives second sets of measurements, determines the CRI values based on the measurements, and determines an optimal CRT treatment.

Referring to FIG. 29, the data structure or matrix 1000 may have a first or high priority, such as always acquired 1020, a second priority, such as usually acquired 1022, and a third priority, such as sometimes acquired 1024. Referring to FIG. 30, the data structure or matrix 1010 may have a first or high priority, such as always acquired 1020, a second priority, such as usually acquired 1022, a third priority, such as sometimes acquired 1024, and a fourth priority, such as not available 1026.

In some examples, the computing apparatus 140 may receive user input indicating the priorities or selections to be used to filter the entries and determine the individualized IMD characteristics. For example, the computing apparatus 140 may cause display of a data structure on display 132. Then, the computing apparatus 140 may receive user input indicating a selection, such as always acquired 1020 and usually acquired 1022. The computing apparatus 140 may determine the entries within a data structure, such as data structure 1000 or 1010, that have a corresponding priority indicating always acquired 1020 and usually acquired 1022.

In some instances, the data structure may be pre-programmed and/or pre-defined to filter the entries. For example, the computing apparatus 140 may determine the individualized 1 MB characteristics as the entries that have a first priority, such as always acquired 1020. Additionally, and/or alternatively, the computing apparatus 140 may receive user input indicating, a second priority, such as usually acquired 1022. Based on the user input, the computing apparatus 140 may add the entries corresponding to usually acquired 1022 to the individualized IMD characteristics.

Additionally, and/or alternatively, the computing apparatus 140 may receive user input indicating additional entries to be selected and/or entries to be removed. For example, the computing apparatus 140 may receive user input indicating to add one or more entries corresponding to sometimes acquired 1024 (e.g., the entry for A-LV of 160 ms and A-RV of 140 ms) to the individualized 1 MB characteristics. The computing apparatus 140 may add the entry for A-LV of 160 ms and A-RV of 140 ms to the individualized IMD characteristics. Additionally, and/or alternatively, the computing apparatus 140 may receive user input indicating to remove one or more entries corresponding to usually acquired 1022 (e.g., the entry for A-LV of 140 ms and A-RV of 200 ms) from the individualized IMD characteristics.

At block 910, based on the individualized IMD characteristics determined from block 906, the computing apparatus 140 may receive, from the measurement electrodes 112 and/or 114, second sets of measurements (e.g., second measurements) corresponding to the determined IMD characteristics. Block 910 may function similarly to block 206 described above. For example, at block 908, the computing apparatus 140 may determine multiple different characteristics (e.g., multiple different delays from the data structure such as structure 1000). The 1 MB 16 may receive and/or apply the individualized 1 MB characteristics. In response to applying each individualized IMD characteristics, the computing apparatus 140 may receive a set of second measurements from the measurement electrodes 112 and/or 114 for the corresponding individualized IMD characteristic.

In some examples, the computing apparatus 140 may sort the individualized 1 MB characteristics to be applied to the IMD 16. For example, the computing apparatus 140 may initially apply the LV-only individualized IMD characteristics (e.g., the top row entries from data structure 1000). Then, the computing apparatus 140 may apply the entries with the same A-LV delays (e.g., moving column by column within the data structure 1000).

At block 912, the computing apparatus 140 may determine the CRI values of the measurements and/or populate the data structure using the CRI values and the information indicating the delays. Block 912 may function similarly to block 208 above. For example, the computing apparatus 140 may determine CRI values based on comparisons between the first (e.g., native measurements) and second measurements (e.g., measurements with corresponding individualized IMD characteristics). After determining the CRI values, the computing apparatus 140 may populate the CRI values for each corresponding entry in the data structure, such as structure 1000. For example, the computing apparatus 140 may use the second measurements corresponding to A-LV of 140 ms and A-RV of 140 ms and the native measurements to determine a CRI value as described above. Then, the computing apparatus 140 may populate the entry for A-LV of 140 ms and A-RV of 140 ms with the determined CRI value. For each of the determined 1 MB characteristics, the computing apparatus 140 may populate the corresponding entry of the data structure, such as structure 1000, with their CRI value.

At block 914, the computing apparatus 140 may generate and/or cause display of a graphical representation of the populated data structure, such as structure 1000, on a display device, such as display 132. The graphical representation may be any type of graphical representation, such as graphs, charts, heat maps, and so on. In some instances, the computing apparatus 140 may might not receive CRI values for each of the entries within the data structure, such data structure 1010. As such, the computing apparatus 140 may use a best fit calculation (e.g., best fit curve, best fit line, average, and so on) to populate the data structures and generate the graphical representations. For example, for the entries with not available 1026 priorities, the computing apparatus 140 might not receive CRI values for them. In such instances, the computing apparatus 140 uses a best fit calculation for these entries and generates a graphical representation based on the best fit calculation(s).

Figure 31:
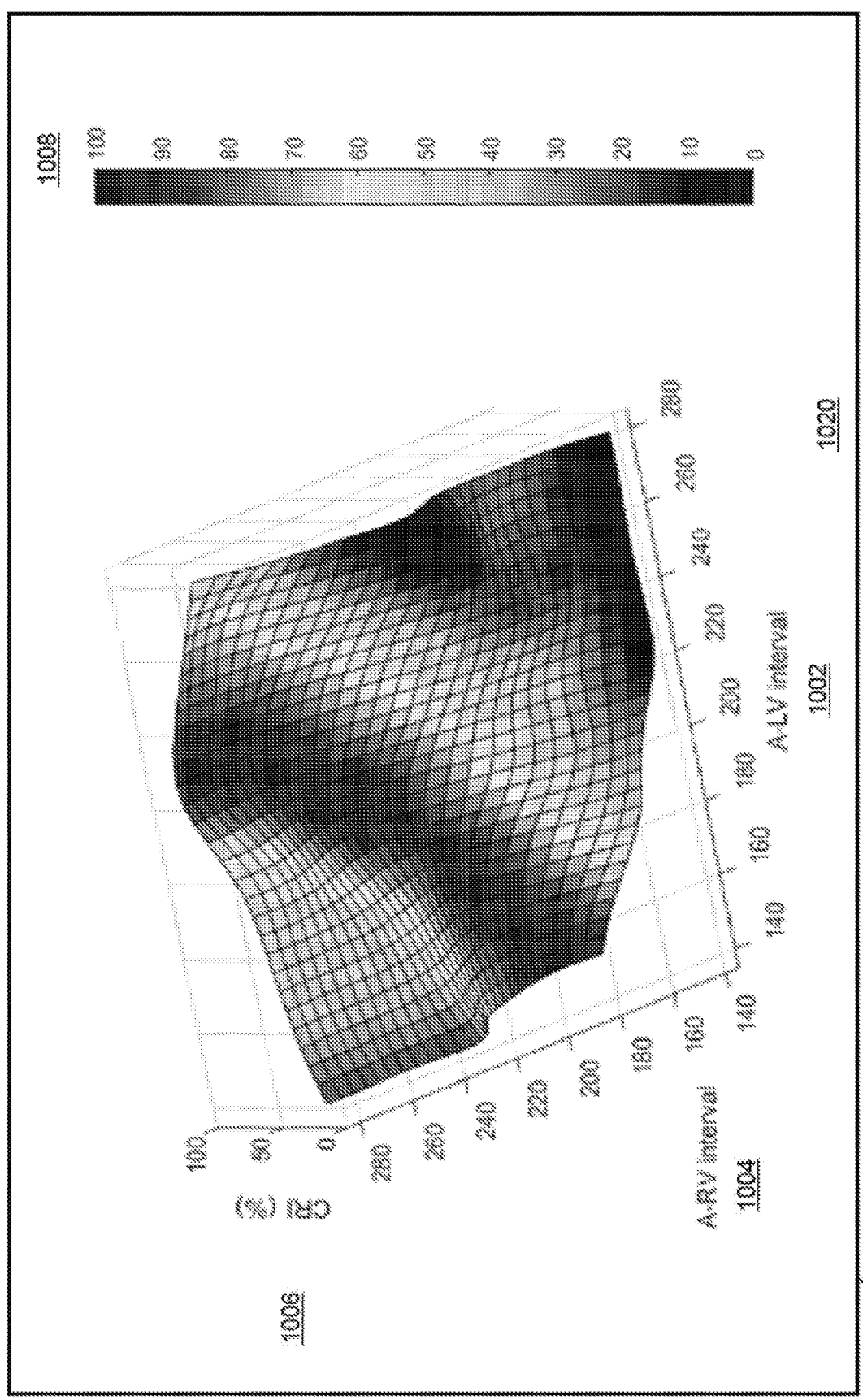
FIG. 31 is another exemplary graphical user interface depicting a graphical representation of the data structure used to determine optimal CRT treatments.
Figure 32:
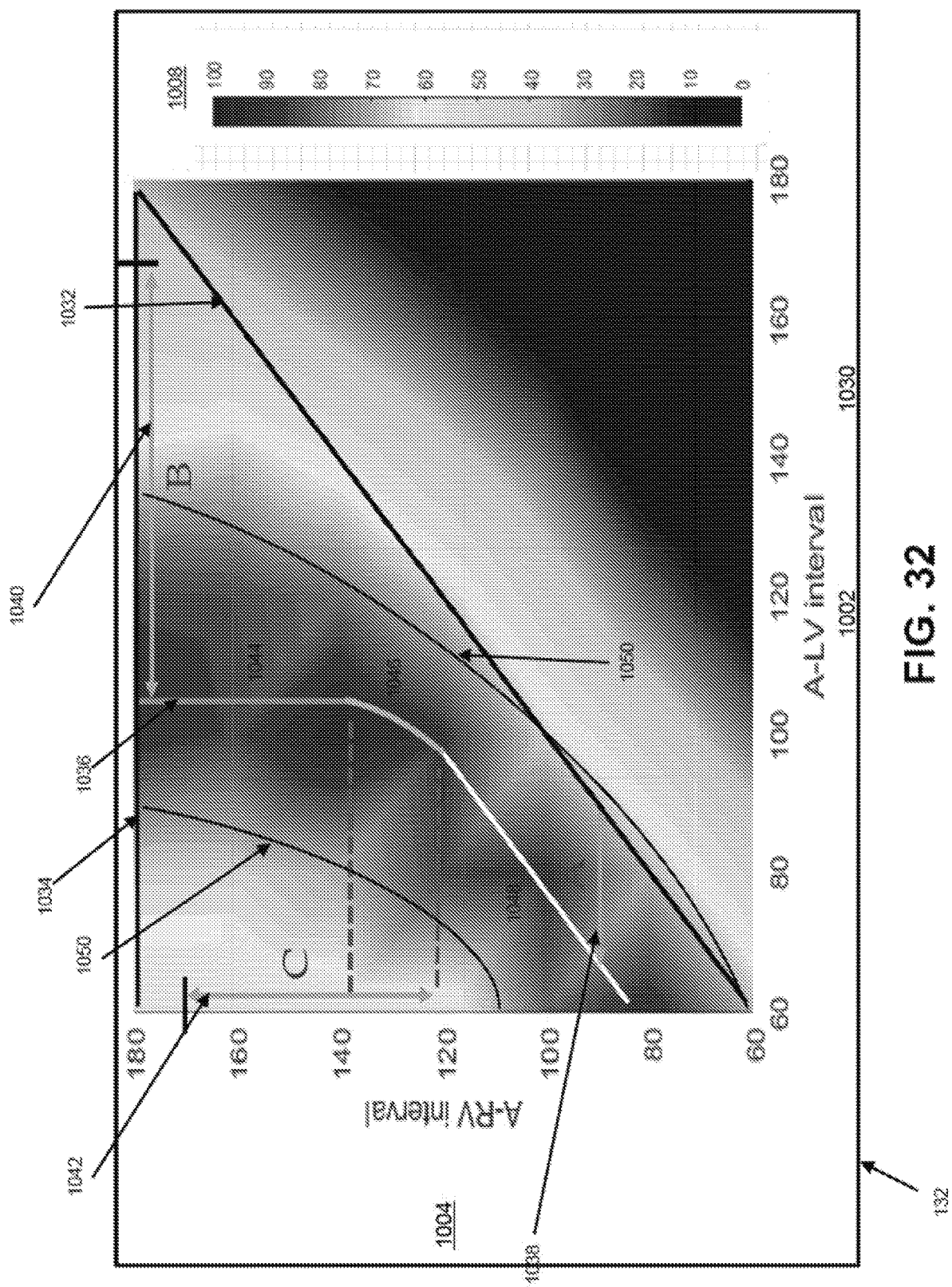
FIG. 32 is another exemplary graphical user interface depicting another graphical representation of the data structure used to determine optimal CRT treatments.
Figure 33:
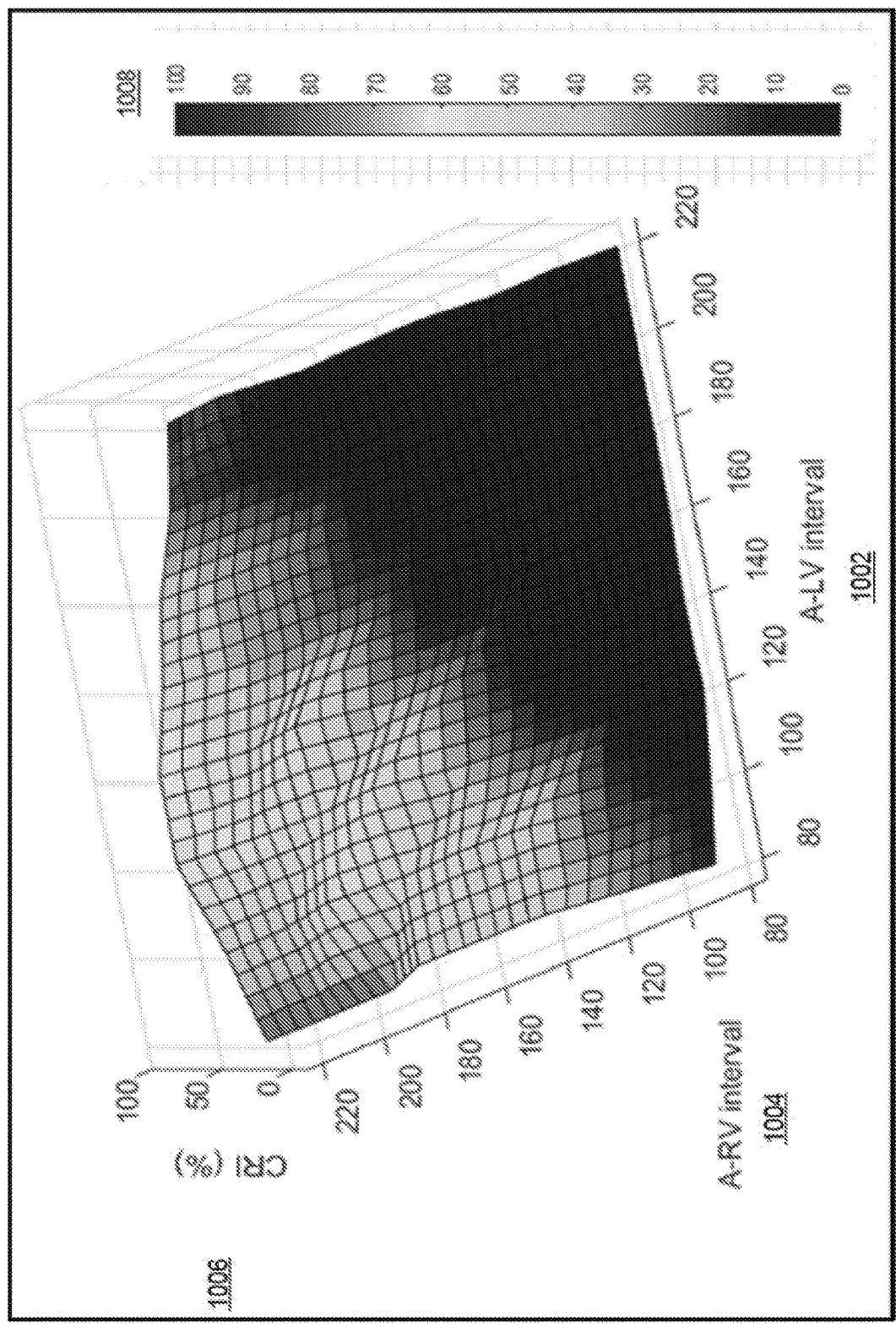
FIG. 33 is another exemplary graphical user interface depicting another graphical representation of the data structure used to determine optimal CRT treatments.
Figure 34:
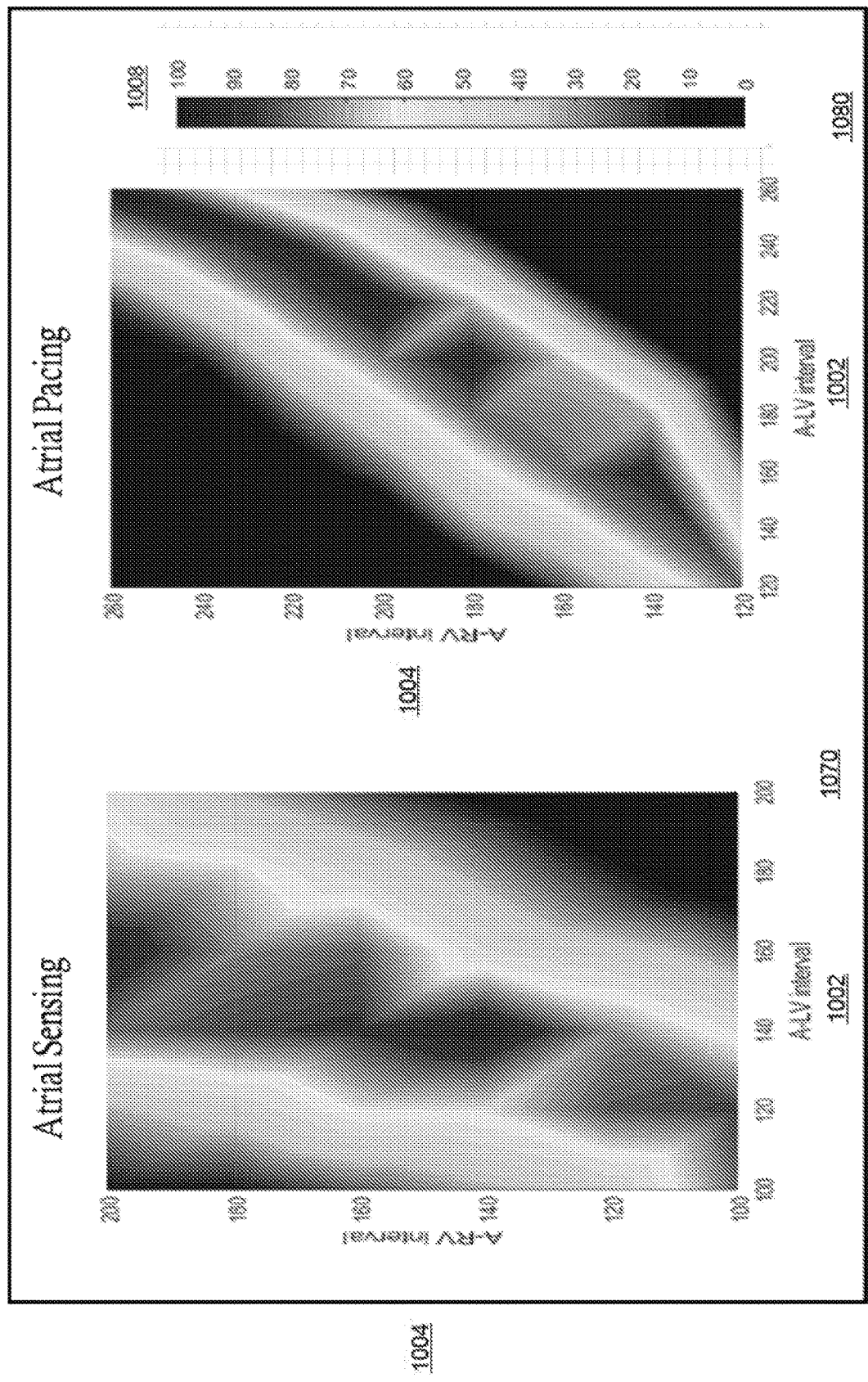
FIG. 34 is another exemplary graphical user interface depicting another graphical representation of the data structure used to determine optimal CRT treatments.

FIGS. 31-33 show exemplary graphical representations of the populated data structure. FIG. 31 shows a 3-D heat map 1020 for a populated data structure, such as structure 1000. For example, the computing apparatus 140 may cause display of the 3-D heat map 1020 on the display 132. The 3-D heat map 1020 includes on the x-axis the A-LV interval 1002, on the y-axis the A-RV interval 1004, and on the z-axis the CRI (%) 1006. Furthermore, the legend 1008 shows the corresponding CRI values for the different entries from the data structure 1000.

FIG. 32 shows another heat map 1030 for a populated data structure, such as structure 1000, that the computing apparatus 140 may cause displayed on the display 132. Furthermore, the computing apparatus 140 may generate and/or cause display of other various indicia on the display 132. For example, the computing apparatus 140 may cause display of indicia 1032 and 1034. Indicia 1032 may represent the BiV entries with no VV delay (e.g., the A-RV and A-LV delays being the same). Indicia 1034 may represent the LV only entries (e.g., the top row from the data structure 1000).

The computing apparatus 140 may also cause display of indicia 1036 (e.g., an CRI optimal curve) and indicia 1050. Indicia 1050 represent a programming window for the user/doctor to use in programming the IMD 16. In other words, indicia 1050 shows regions where the CRI values are above a certain CRI threshold (e.g., 80%). These regions may be used for the optimal CRT treatment settings to be programmed in the IMD 16. For example, from the data structure 1000, the computing apparatus 140 may determine the entries with CRI values exceeding a pre-defined, pre-determined, and/or user-defined threshold (e.g., 80%). Then, the computing apparatus 140 may generate and cause display of an indicia such as 1036 indicating the entries exceeding the threshold. In other words, the computing apparatus 140 may cause display of a curvilinear line that runs through the center of the portion of the graphical representation (e.g., heat map 1030) of the data structure. The indicia 1036 may include 3 different sections 1044, 1046, and 1048. Section 1044 represents an optimal fusion and/or cancellation between the native pulse and LV lead 20 pulse. Section 1046 represents an optimal fusion and/or cancellation between the native pulse, the LV lead 20 pulse, and the RV lead 18 pulse. Section 1048 represents an optimal fusion and/or cancellation between the RV lead 18 pulse and the LV lead 20 pulse.

Additionally, and/or alternatively, the computing apparatus 140 may cause display of indicia 1038, 1040, and 1042 (e.g., A, B, and C). Indicia 1038 represents the optimal 1 MB characteristic between the RV to LV delay (e.g., the optimal VV delay setting for the IMD 16). Indicia 1040 represents the optimal IMD characteristic between the native measurement to the optimal LV delay (during LV-only pacing). Indicia 1042 represents the optimal IMD characteristic between the native measurement to the optimal RV delay.

At block 916, the computing apparatus 140 may determine whether to generate a new data structure and/or graphical representation. In some variations, based on the CRI values from the data structure being below a threshold (e.g., below 80%), the computing apparatus 140 may determine to generate a new data structure and/or graphical representation. Then, the processing sequence 900 may move back to block 904. For example, if all the individualized 1 MB characteristics for the entries from the data structure are below a threshold, then the computing apparatus 140 may determine to generate a new data structure. Otherwise, the processing sequence may move to block 918.

Additionally, and/or alternatively, based on received user input indicating a new data structure and/or graphical representation is needed, the computing apparatus 140 may determine to generate a new data structure and/or graphical representation. Furthermore, as discussed below, the user input may indicate new types of information such as different IMD 16 configurations (e.g., atrial sensed, atrial paced, different cathode/anode pairs). Then, the processing sequence 900 may move back to block 904.

At block 918, the computing apparatus 140 may determine one or more optimal CRT treatments based on the generated graphical representation and/or populated data structure and/or provide information to administer the CRT treatment. Block 918 may function similarly to block 210 described above and is further described in FIG. 11. For instance, the computing apparatus 140 may cause display of the generated graphical representation of the data structure on the display device 132. Based on the generated graphical representation, the computing apparatus 140 may receive user input indicating the optimal CRT treatment. The computing apparatus 140 may provide information to the IMD 16 indicating the optimal CRT treatment. In other words, the computing apparatus 140 may set the IMD 16 to the determined optimal CRT treatment (e.g., delays between the RA lead 22, LV lead 20, and RV lead 18). Then, the processing sequence 900 may end.

If the processing sequence 900 moves back to block 904, the computing apparatus 140 may determine new information related to the data structure and indicating delays corresponding to the RA lead 22, LV lead 20, and/or RV lead 18. For example, the new information may include operating the IMD 16 in a different mode (e.g., change the electrode vector used for the CRI values and/or change the mode from AS to AP or vice versa) and/or determining new delays (e.g., A-RV and/or A-LV delays). The computing apparatus 140 may determine the new information automatically and/or based on user input. For example, the computing apparatus 140 may retrieve instructions from memory, such as memory 152, and/or indicating the new information. Additionally, and/or alternatively, the computing apparatus 140 may receive user input indicating the new information.

In some instances, the new information may include operating the IMD 16 in a different mode. For example, if the IMD 16 was operating in a first mode (e.g., AS mode) in the previous iteration, the computing apparatus 140 may provide instructions (e.g., directly and/or via display 132 and user input to the IMD 16) to the IMD 16 to operate in a new or second mode (e.g., AP mode). The computing apparatus 140 may apply the individualized IMD characteristics and receive second sets of measurements based on the 1 MB 16 operating in the new mode.

In other words, if initially, the individualized IMD characteristics applied to the 1 MB 16 to acquire the second set of measurements for the CRI values was performed when the 1 MB 16 was in AS mode (e.g., the RA lead 22 is sensing the native signal for the wavefront), then for the next iteration (e.g., moving back to block 904), the computing apparatus 140 may apply the individualized IMD characteristics in the AP mode (e.g., the RA lead 22 is providing the signal for the wavefront). If the original second set of measurements was when the 1 MB 16 was in AP mode, then the computing apparatus 140 may apply the individualized IMD characteristics in the AS mode. Additionally, and/or alternatively, the computing apparatus 140 may determine new A-LV and/or A-RV delays, intervals, size, and so on for the IMD 16 for the second iteration.

In some instances, if the IMD 16 was using a first electrode vector in the previous iteration, the computing apparatus 140 may provide instructions (e.g., directly and/or via display 132 and user input to the IMD 16) to the IMD 16 to use a second electrode vector. The computing apparatus 140 may apply the individualized IMD characteristics and receive second sets of measurements based on the IMD 16 using the second electrode vector.

In other words, in the first iteration, the computing apparatus 140 determines a first vector (e.g., one or more pacing electrodes such as electrodes 40, 42, 44, 45, 46, 47, 48, 50 from a lead, such as the LV lead 20) to apply the individualized 1 MB characteristics from the data structure. For example, for the first iteration, the computing apparatus 140 may determine to turn on the electrode 44 of the LV lead 20 to apply the pacing pulses. For the second iteration, the computing apparatus 140 may determine a new or second vector (e.g., the electrode 47 from the LV lead 20) to apply the pacing pulses. The processing sequence 900 may continuously repeat and apply different vectors to the 1 MB 16 to determine different CRI values for the individualized 1 MB characteristics. 140 may generate a new data structure (e.g., a new matrix including new A-LV and/or A-RV delays, intervals, size, and so on) for the IMD 16 operating in the second mode.

In some instances, the computing apparatus 140 may provide instructions (e.g., directly and/or via display 132 and user input to the IMD 16) to the 1 MB 16 to apply a different multi-point pacing configuration. With multi-point pacing, 2 different LV electrodes (e.g., 44, 45, 46, 47) serve as cathodes with variable timing delays between the pacing stimulus with each electrode. For example, the computing apparatus 140 may adjust the timing of two or more cathodes from the LV leads 20 such as electrodes 44 and 46 and indicate when those 2 leads fire off their LV pulse to meet up with RV lead/native. The computing apparatus 140 may use data structures and/or information for the data structures for multi-point pacing compared to single point pacing (e.g., using 1 LV lead electrode).

FIG. 33 shows a 3-D heat map 1060 for a populated data structure, such as structure 1010. For example, the computing apparatus 140 may cause display of the 3-D heat map 1060 on the display 132. The 3-D heat map 1060 includes on the x-axis the A-LV interval 1002, on the y-axis the A-RV interval 1004, and on the z-axis the CRI (%) 1006. As shown, graphical representation 1060 does not include any CRI values above 60%. This may be due to the electrode leads (LV lead 20) being in a suboptimal (usually anterior) position such that an adequate wavefront fusion and cancellation cannot be achieved. For example, referring back to FIG. 13, if the LV lead 20 is located closer to the bottom or anterior position, the LV lead 20 pulse would begin closer to the center line 653. As such, the pulse from the lead 20 may never optimally cancel with the pulse from the RV lead 18 and/or the native pulse at the center 653 of the left ventricle.

If similar data structures are acquired when pacing from different LV electrodes such as electrodes 44-48 and still no CRI values are above a certain threshold (e.g., 60%), then the LV lead 20 is likely to be positioned poorly and consideration is needed to be given to possible LV lead replacement. In other words, the computing apparatus 140 may move through several iterations of processing sequence 900 and generate new information for new data structures and new graphical representations. If the computing apparatus 140 determines there are no optimal CRT treatment settings able to be used (e.g., the CRI values are below a threshold such as 60%), the computing apparatus 140 may determine the LV lead 20 is positioned poorly. After, the computing apparatus 140 may cause display of a prompt indicating that the LV lead 20 is positioned poorly. By displaying the prompt, a doctor may move the LV lead 20 of the patient to a more optimal position and acquire better CRI values/ optimal CRT treatment settings.

The techniques described in this disclosure, including those attributed to the 1 MB 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by processing circuitry and/or one or more processors to support one or more aspects of the functionality described in this disclosure.

As described herein, the exemplary systems, methods, and interfaces may be used to provide noninvasive assistance to a user in the evaluation of a patient's cardiac health or status, and/or the valuation of cardiac therapy (e.g., cardiac therapy being presently-delivered to a patient during implantation or after implantation). Further, the exemplary systems, methods, and interfaces may be used to assist a user in the configuration of the cardiac therapy being delivered to a patient. For instance, the exemplary systems, methods, and interfaces may be used to test a plurality of various cardiac therapy settings and present the results of the various cardiac therapy settings to a user via the graphical user interface. Further, for instance, the exemplary systems, methods, and interfaces may test a plurality of various cardiac therapy settings and present one or more effective cardiac therapy settings to the user. In at least one embodiment, the exemplary systems, methods, and interfaces may automatically program the cardiac therapy apparatus to use the effective cardiac therapy settings.

The above detailed description of the present disclosure and the examples described therein have been presented for the purposes of illustration and description only and not by limitation. It is therefore contemplated that the present disclosure covers any and all modifications, variations or equivalents that fall within the spirit and scope of the basic underlying principles disclosed above and claimed herein.

What is claimed is:

1. A system for cardiac resynchronization of a patient, the system comprising:

one or more processors configured to be in communication with a plurality of measurement electrodes operatively coupled to the patient; and a tangible, non-transitory storage medium comprising instructions that, when executed by the one or more processors, cause the one or more processors to:

receive, from the plurality of measurement electrodes, a first set of electrical measurements indicating first electrical signals applied to the patient's heart;

receive one or more input variables;

based on the one or more input variables, determine information corresponding to a data structure and indicating delays associated with an atrium lead, a left ventricle (LV) lead, and a right ventricle (RV) lead;

determine a plurality of individualized medical device characteristics based on the information corresponding to the data structure;

based on the plurality of individualized medical device characteristics, receive, from the plurality of measurement electrodes, a plurality of second sets of electrical measurements indicating second electrical signals applied to the patient's heart, the plurality of second sets of electrical measurements indicating a response of the patient's heart to therapy delivery by a medical device according to the plurality of individualized medical device characteristics;

determine cardiac resynchronization index (CRI) values using the first set of electrical measurements and the plurality of second sets of electrical measurements;

populate the data structure based on the CRI values and the information indicating the delays;

generate a graphical representation based on the populated data structure; and cause display of the graphical representation corresponding to the populated data structure on a display device.

2. The system of claim 1, wherein the information corresponding to the data structure indicates a plurality of entries, wherein each entry of the plurality of entries is associated with a first delay characteristic of a right atrium (RA) lead of the medical device to a left ventricle (LV) lead of the medical device and a second delay characteristic of the RA lead of the medical device to a right ventricle (RV) lead of the medical device.

3. The system of claim 2, wherein a first subset of the plurality of entries is associated with a plurality of LV lead only delay characteristics, and wherein a second subset of the plurality of entries is associated with a plurality of bi-ventricular (BiV) lead characteristics without ventricular-ventricular (VV) delay characteristic.

4. The system of claim 2, wherein a first subset of the plurality of entries is associated with a first priority, and wherein the determining the plurality of individualized medical device characteristics comprises filtering the plurality of entries based on the first priority.

5. The system of claim 4, wherein a second subset of the plurality of entries is associated with a second priority, and wherein the determining the plurality of individualized medical device characteristics further comprises:
receiving user input indicating the second priority; and
including the second subset of the plurality of entries corresponding to the second priority to the plurality of individualized medical device characteristics.

6. The system of claim 4, wherein the determining the plurality of individualized medical device characteristics further comprises:
receiving user input indicating one or more entries from the plurality of entries; and
including the one or more entries from the plurality of entries to the plurality of individualized medical device characteristics.

7. The system of claim 2, wherein the generating the graphical representation based on the populated data structure comprises generating a heat map based on the determined CRI values, the first delay characteristic, and the second delay characteristic.

8. The system of claim 7, wherein the causing display of the graphical representation comprises causing display of the heat map and one or more visual indicia, wherein the one or more visual indicia indicates at least one optimal cardiac resynchronization therapy (CRT) treatment corresponding to an individualized medical device characteristic from the plurality of individualized medical device characteristics.

9. The system of claim 1, wherein the one or more input variables indicate a patient category corresponding to a condition of the patient's heart, and wherein the determining the information corresponding to the data structure and indicating the delays is based on the patient category.

10. The system of claim 1, wherein the one or more input variables indicate a device type of the medical device, and wherein the determining the information corresponding to the data structure and indicating the delays is based on the device type of the medical device.

11. The system of claim 1, wherein the tangible, non-transitory storage medium further comprises instructions that, when executed by the one or more processors, cause the one or more processors to:
determine new information corresponding to the data structure and indicating the delays, wherein the new information indicates to operate the medical device in a different mode;
receive, from the plurality of measurement electrodes and based on the new information indicating to operate the medical device in the different mode, a plurality of third sets of electrical measurements indicating third electrical signals applied to the patient's heart;
determine new CRI values using the first set of electrical measurements and the plurality of third sets of electrical measurements;
populate the data structure based on the new CRI values and the new information;
generate a new graphical representation based on the populated data structure; and
cause display of the new graphical representation on the display device.

12. The system of claim 11, wherein new information indicates new delays corresponding to the atrium lead, the LV lead, and the RV lead.

13. The system of claim 11, wherein the new information indicating to operate the medical device in the different mode comprises switching the medical device from an atrial sensing mode to an atrial pacing mode.

14. The system of claim 11, wherein the new information indicating to operate the medical device in the different mode comprises switching the medical device from an atrial pacing mode to an atrial sensing mode.

15. The system of claim 11, wherein the new information indicating to operate the medical device in the different mode comprises switching the medical device from a first electrode vector corresponding to a first electrode of a left ventricle (LV) lead to a second electrode vector corresponding to a second electrode of the LV lead.

16. The system of claim 11, wherein the tangible, non-transitory storage medium further comprises instructions that, when executed by the one or more processors, cause the one or more processors to:
determine the CRI values and the new CRI values are below a threshold; and
based on the CRI values and the new CRI values being below the threshold, cause display of a prompt indicating the LV lead is in a sub-optimal position.

17. The system of claim 1, wherein the one or more processors are configured to send instructions or commands to the medical device to cause the medical device to apply the therapy according to the plurality of individualized medical device characteristics.

18. A method for cardiac resynchronization of a patient, comprising:
receiving, from a plurality of measurement electrodes, a first set of electrical measurements indicating first electrical signals applied to the patient's heart;
receiving one or more input variables;
based on the one or more input variables, determining information corresponding to a data structure and indicating delays associated with an atrium lead, a left ventricle (LV) lead, and a right ventricle (RV) lead;
determining a plurality of individualized medical device characteristics based on the information corresponding to the data structure;
based on the plurality of individualized medical device characteristics, receiving, from the plurality of measurement electrodes, a plurality of second sets of electrical measurements indicating second electrical signals applied to the patient's heart, the plurality of second sets of electrical measurements indicating a response of the patient's heart to therapy delivery by a medical device according to the plurality of individualized medical device characteristics;
determining cardiac resynchronization index (CRI) values using the first set of electrical measurements and the plurality of second sets of electrical measurements;
populating the data structure based on the CRI values and the information indicating the delays;
generating a graphical representation based on the populated data structure; and
causing display of the graphical representation corresponding to the populated data structure on a display device.

19. The method of claim 18, wherein the information corresponding to the data structure indicates a plurality of entries, wherein each entry of the plurality of entries is associated with a first delay characteristic of a right atrium (RA) lead of the medical device to a left ventricle (LV) lead of the medical device and a second delay characteristic of the RA lead of the medical device to a right ventricle (RV) lead of the medical device.

20. The method of claim 18, further comprising sending instructions or commands to the medical device to cause the medical device to apply the therapy according to the plurality of individualized medical device characteristics.

21. A non-transitory computer readable medium storing instructions for execution by one or more processors incorporated into a system, wherein execution of the instructions by the one or more processors cause the one or more processors to:
receive, from a plurality of measurement electrodes, a first set of electrical measurements indicating first electrical signals applied to the patient's heart;
receive one or more input variables;
based on the one or more input variables, determine information corresponding to a data structure and indicating delays associated with an atrium lead, a left ventricle (LV) lead, and a right ventricle (RV) lead;
determine a plurality of individualized medical device characteristics based on the information corresponding to the data structure;
based on the plurality of individualized medical device characteristics, receive, from the plurality of measurement electrodes, a plurality of second sets of electrical measurements indicating second electrical signals applied to the patient's heart, the plurality of second sets of electrical measurements indicating a response of the patient's heart to therapy delivery by a medical device according to the plurality of individualized medical device characteristics;
determine cardiac resynchronization index (CRI) values using the first set of electrical measurements and the plurality of second sets of electrical measurements;
populate the data structure based on the CRI values and the information indicating the delays;
generate a graphical representation based on the populated data structure; and
cause display of the graphical representation corresponding to the populated data structure on a display device.

22. The non-transitory computer readable medium of claim 21, wherein the information corresponding to the data structure indicates a plurality of entries, wherein each entry of the plurality of entries is associated with a first delay characteristic of a right atrium (RA) lead of the medical device to a left ventricle (LV) lead of the medical device and a second delay characteristic of the RA lead of the medical device to a right ventricle (RV) lead of the medical device.

* * * * *